United States Patent [19]

Ogihara et al.

[11] Patent Number: 5,665,271
[45] Date of Patent: Sep. 9, 1997

[54] SILACYCLOHEXANE COMPOUNDS, PREPARATION THEREOF, LIQUID CRYSTAL COMPOSITIONS COMPRISING THE SAME, AND LIQUID CRYSTAL DEVICES COMPRISING THE COMPOSITIONS

[75] Inventors: Tsutomu Ogihara; Takaaki Shimizu; Takeshi Kinsho; Tatsushi Kaneko; Kazuyuki Asakura; Mutsuo Nakashima, all of Niigata-ken, Japan

[73] Assignee: Shin-Etsu Chemical Co., Ltd., Tokyo, Japan

[21] Appl. No.: 598,595

[22] Filed: Feb. 12, 1996

[30] Foreign Application Priority Data

Feb. 13, 1995 [JP] Japan .................................. 7-047798
May 12, 1995 [JP] Japan .................................. 7-138459

[51] Int. Cl.$^6$ .............................. C09K 19/34; C07F 7/08
[52] U.S. Cl. .............................. 252/299.61; 556/406
[58] Field of Search .................... 252/299.01, 299.63; 359/103; 556/406

[56] References Cited

U.S. PATENT DOCUMENTS

| | | | |
|---|---|---|---|
| 5,454,977 | 10/1995 | Shimizu et al. | 252/299.61 |
| 5,496,501 | 3/1996 | Shimizu et al. | 252/299.61 |
| 5,498,737 | 3/1996 | Ogihara et al. | 556/406 |
| 5,514,824 | 5/1996 | Kingho et al. | 556/406 |
| 5,519,156 | 5/1996 | Kingho et al. | 556/406 |
| 5,523,439 | 6/1996 | Ogihara et al. | 556/406 |
| 5,523,440 | 6/1996 | Nakashima et al. | 556/406 |
| 5,527,490 | 6/1996 | Kingho et al. | 252/299.61 |
| 5,543,539 | 8/1996 | Shimizu et al. | 556/406 |
| 5,547,606 | 8/1996 | Kingho et al. | 252/299.61 |
| 5,560,866 | 10/1996 | Ogihara et al. | 252/299.61 |
| 5,567,350 | 10/1996 | Shimizu et al. | 252/299.61 |
| 5,573,705 | 11/1996 | Kaneko et al. | 252/299.61 |
| 5,578,244 | 11/1996 | Shimizu et al. | 252/299.61 |
| 5,582,764 | 12/1996 | Nakashima et al. | 252/299.61 |
| 5,582,765 | 12/1996 | Kingho et al. | 252/299.61 |

FOREIGN PATENT DOCUMENTS

| | | |
|---|---|---|
| 0568040 | 11/1993 | European Pat. Off. . |
| 0630903 | 12/1994 | European Pat. Off. . |
| 0648773 | 4/1995 | European Pat. Off. . |
| 0665232 | 8/1995 | European Pat. Off. . |

Primary Examiner—Shean C. Wu
Attorney, Agent, or Firm—Lowe, Price, LeBlanc & Becker

[57] ABSTRACT

Silacyclohexane compounds of the following formula (I) or (II) along with intermediate compounds therefor are described

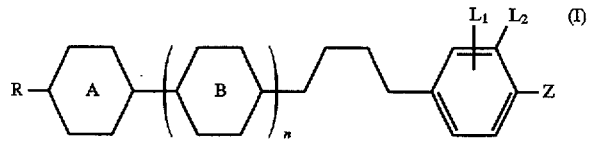

wherein R is an organic residue, one of

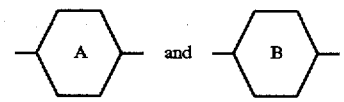

represents a trans-1-sila-1,4-cyclohexylene group or trans-4-sila-1,4-cyclohexylene group having a substituent of H, F, Cl or $CH_3$, and the other represents a trans-1,4-cyclohexylene group, or such a trans-1-sila-1,4-cyclohexylene group or trans-4-sila-1,4-cyclohexylene group as defined above, n is 0 or 1, $L_1$ represents H or F, $L_2$ represents H, F or Cl, and Z represents CN, F, Cl or an organic residue, and

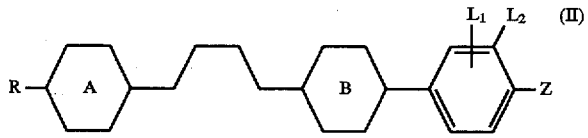

The processes for preparing the compounds (I) and (II) are also described along with liquid crystal compositions comprising the compounds and the liquid crystal devices comprising the compositions.

29 Claims, No Drawings

SILACYCLOHEXANE COMPOUNDS, PREPARATION THEREOF, LIQUID CRYSTAL COMPOSITIONS COMPRISING THE SAME, AND LIQUID CRYSTAL DEVICES COMPRISING THE COMPOSITIONS

BACKGROUND OF THE INVENTION

1. Field of The Invention

This invention relates to novel silacyclohexane compounds and the preparation thereof. The invention also relates to intermediate compounds for the silacyclohexane compounds, to liquid crystal compositions comprising the silacyclohexane compound or compounds, and to devices comprising the compositions.

2. Description of the Prior Art

The liquid crystal display devices utilize optical anisotropy and dielectric anisotropy of liquid crystal substances. Depending on the mode of display, different types of display systems are known including those of a twisted nematic type (TN type), a supertwisted nematic type (STN type), a super birefringence type (SBE type), a dynamic scattering type (DS type), a guest/host type, a type of deformation of aligned phase (DAP type), a polymer dispersion type (PD type), and an optical mode interference type (OMI type). The most popular display device is one which is based on the Schadt-Helfrich effect and has a twisted nematic structure.

Although the properties of the liquid crystal substances used in these liquid crystal devices depend, more or less, on the type of display, it is commonly required that the liquid crystal substances have a wide range of temperatures working as a liquid crystal and that they be stable against moisture, air, light, heat, electric field and the like. Moreover, the liquid crystal substances should desirably be low in viscosity and should ensure a short address time, a low threshold voltage and a high contrast in cells.

Liquid substances which can satisfy all the requirements have never been known when used singly. In practice, several to ten and several liquid compounds and/or latent liquid crystal compounds are used in the form of a mixture. To this end, it is important that constituent components be readily compatible with one another.

Existing liquid crystal compounds usable as these constituent components include those compounds which have a cyclohexyl ring-butylene-phenyl ring (QPCH) structure or a cyclohexyl ring-cyclohexyl ring-butylene-phenyl ring (QPCC) structure.

As liquid crystal display devices have wider utility in various fields, the characteristic properties required for liquid crystal materials become severer. In fact, liquid crystal materials now demanded should have an improved low temperature performance, a wider working temperature satisfying on-vehicle needs and a lower drive voltage on comparison with existing liquid crystal materials or compositions.

SUMMARY OF THE INVENTION

It is accordingly an object of the invention to provide novel compounds which have an Si-containing silacyclohexane ring structure in the molecule, unlike known liquid crystal compounds having a cyclohexyl ring-butylene-phenyl ring structure or a cyclohexyl ring-cyclohexyl ring-butylene-phenyl ring structure and which serve as a liquid crystal substance whereby characteristic properties as a liquid crystal are improved.

It is another object of the invention to provide intermediate compounds which are useful for preparing the novel silacyclohexane compounds but do not exhibit any liquid crystal properties.

It is a further object of the invention to provide processes for preparing the novel compounds and the intermediate compounds as mentioned above.

It is a still further object of the invention to provide a liquid crystal composition which comprise at least a compound of the type as set out above and also a liquid crystal display device comprising the composition.

The above objects can be achieved, according to one embodiment of the invention, by a silacyclohexane compound selected from the group consisting of compounds of the following formulas (I) and (II)

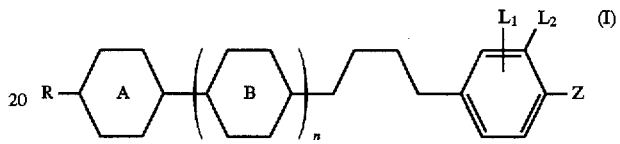

wherein R represents a linear alkyl group having from 1 to 10 carbon atoms, a mono or difluoroalkyl group having from 1 to 10 carbon atoms, a branched alkyl group having from 3 to 8 carbon atoms, an alkoxyalkyl group having from 2 to 7 carbon atoms, or an alkenyl group having from 2 to 8 carbon atoms;

one of

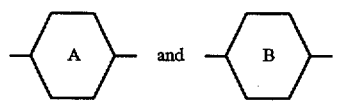

represents a trans-1-sila-1,4-cyclohexylene group or trans-4-sila-1,4-cyclohexylene group in which the silicon atom at the 1 or 4 position has a substituent of H, F, Cl or $CH_3$, and the other represents a trans-1,4-cyclohexylene group, or such a trans-1-sila-1,4-cyclohexylene group or trans-4-sila-1,4-cyclohexylene group as defined above, n is 0 or 1, $L_1$ represents H or F, $L_2$ represents H, F or Cl, and Z represents CN, F, Cl, $CF_3$, $CClF_2$, $CHClF$, $OCF_3$, $OClCF_2$, $OCHF_2$, $OCHClF$, $(O)_m CY=CX_1 X_2$ wherein m is 0 or 1, Y and $X_1$ independently represent H, F or Cl, $X_2$ represents F or Cl, $O(CH_2)_r(CF_2)_s X_3$ wherein r and s are respectively, 0, 1 or 2 provided that r+s is 2, 3 or 4, and $X_3$ represents H, F or Cl, or R or OR wherein R is as defined above, i.e. a linear alkyl group having from 1 to 10 carbon atoms, a linear alkoxy group having from 1 to 10 carbon atoms, an alkoxyalkyl group having from 2 to 7 carbon atoms, a mono or difluoroalkyl group having from 1 to 10 carbon atoms, an alkenyl group having from 2 to 8 carbon atoms, and

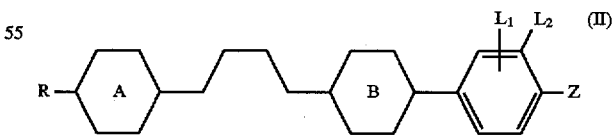

R, $L_1$, $L_2$, Z,

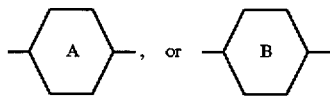

are, respectively, as defined in the formula (I).

As will be apparent from the definition of

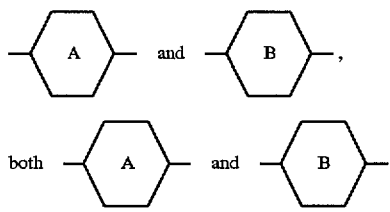

in the formulas (I) and (II) may independently be the trans-1-sila-1,4-cyclohexylene group or the trans-4-sila-1,4-cyclohexylene group as defined above, or one of them may be the trans-1-sila-1,4-cyclohexylene group or the trans-4-sila-1,4-cyclohexylene group and the other may be a trans-1,4-cyclohexylene group.

According to another embodiment of the invention, there are also provided intermediate compounds useful for conversion into the silacyclohexane compounds of the general formulas (I) and (II) wherein one of

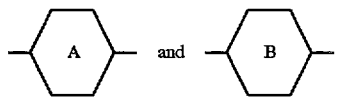

represents a trans-1-sila-1,4-cyclohexylene group or trans-4-sila-1,4-cyclohexylene group in which the silicon atom at the 1 or 4 position has a substituent of H, F, Cl or $CH_3$, and the other represents a trans-1,4-cyclohexylene group, or such a trans-1-sila-1,4-cyclohexylene group or trans-4-sila-1,4-cyclohexylene group as defined just above, wherein the intermediate compounds are of the general formulas (III) and (IV)

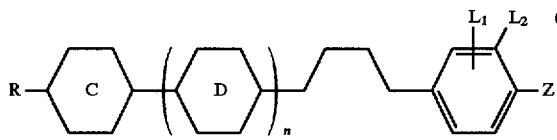

wherein R, $L_1$, $L_2$, Z and n are, respectively, as defined in the formula (I) and one of

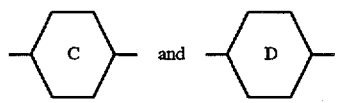

represents a trans-1-sila-1,4-cyclohexylene group or trans-4-sila-1,4-cyclohexylene group in which the silicon atom at the 1 or 4 position has a substituent of phenyl or tolyl, and the other represents a trans-1,4-cyclohexylene group, or such a trans-1-sila-1,4-cyclohexylene group or trans-4-sila-1,4-cyclohexylene group as having phenyl or tolyl, and

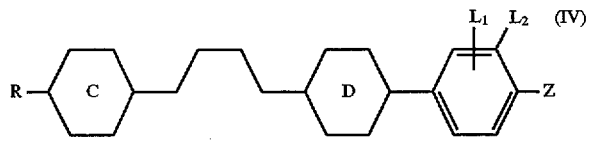

R, $L_1$, $L_2$, Z,

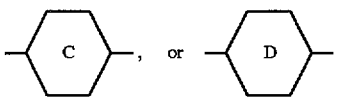

are, respectively, as defined in the formula (III).

The compounds of the formulas (III) and (IV) do not serve as a liquid crystal substance but can be readily converted into those compounds of the general formulas (I) and (II) wherein the silacyclohexane ring or rings have a substituent of F, Cl, H or methyl.

The compound of the formula (I) can be prepared by several processes (a) to (e) directly or through the formation of the compounds of the formulas (III) and (IV).

In the following processes (a) to (e), a substituent is joined to the silicon atom at the 1 or 4 position of the silacyclohexane ring in the following manner

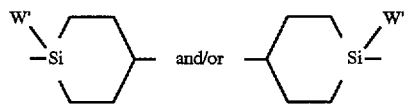

wherein W' is H, methyl or Ar in which Ar represents phenyl or tolyl. In order to obtain the compound of the formula (I) where the substituent joined to the silicon atom at the 1 or 4 position is F or Cl, the phenyl or tolyl is converted to F or Cl as will be described hereinafter. Of course, the phenyl or tolyl may be converted not only to F or Cl, but also to H or methyl.

(a) One of the processes comprises:

reacting an organometallic compound of the general formula, R-M, wherein R, is as defined in the formula (I) and M represents Li, MgP or ZnP wherein P represents a halogen atom, preferably Cl, Br or I, with a compound of the following general formula (1)

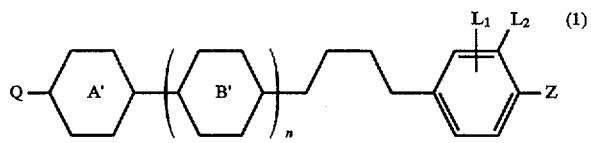

wherein one of

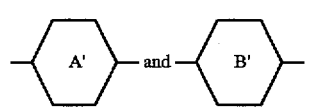

represents

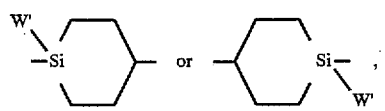

in which W' represents H, methyl, phenyl or tolyl, and, if present, the other represents

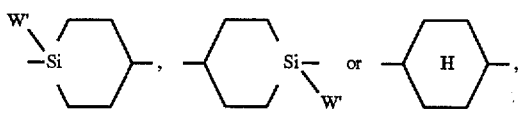

$L_1$, $L_2$ and n are, respectively, as defined in the formula (I), and Q represents a halogen atom, an alkoxy group preferably having from 1 to 4 carbon atoms, a methanesulfonyloxy group, a benzenesulfonyloxy group, a p-toluenesulfonyloxy group or a trifluoromethanesulfonyloxy group, whereby R in the organometallic compound is bonded to the carbon or silicon atom of the compound of the formula (1) to obtain the compound of the general formula (I).

It should be noted that R, $L_1$, $L_2$, Z, n,

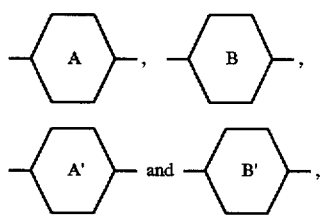

respectively, defined in the formulas (I), (II) and (1) may not be sometimes defined again in formulas appearing hereinafter.

(b) Another process for preparing the compound of the formula (I) comprises:

reacting an organometallic compound of the following formula (2)

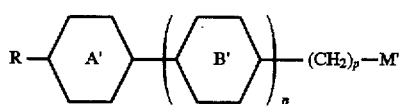

wherein

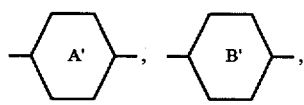

R and n are, respectively, as defined in the foregoing formulas, and M' represents MgP or ZnP wherein P represents a halogen, preferably Cl, Br or I, or $B(OY_1)_2$ wherein $Y_1$ represents H or an alkyl group having from 1 to 6 carbon atoms, with a compound of the following general formula (3)

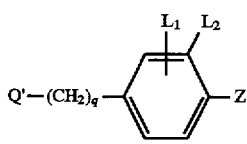

wherein $L_1$, $L_2$ and Z are, respectively, as defined with respect to the formula (I), Q' represents a halogen atom, a methanesulfonyloxy group, a benzenesulfonyloxy group, a p-toluenesulfonyloxy group or a trifluoromethanesulfonyloxy group, p in the formula (2) and q are, respectively, a value of 0, 1, 2, 3 or 4 provided that (p+q) is 4.

(c) A further process comprises:

reacting an organometallic compound of the following formula (4)

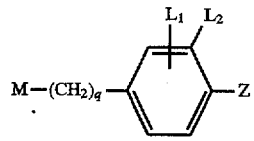

wherein $L_1$, $L_2$, and Z are, respectively, as defined in the formula (I), and M represents Li, MgP or ZnP wherein P is a halogen as defined hereinabove, with a compound of the following general formula (5)

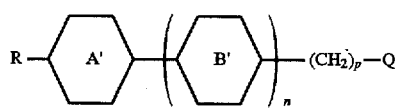

wherein

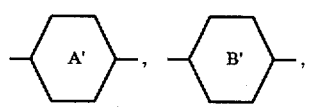

R and n are, respectively, as defined in the foregoing formulas, Q is as defined in the formula (1), and p and q are, respectively, a value of 0, 1, 2, 3, or 4 provided that (p+q) is 4.

(d) A still further process comprises:

reacting an organometallic compound of the following general formula (6)

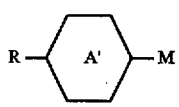

wherein

R and M are, respectively, as defined above, with a compound of the following general formula (7)

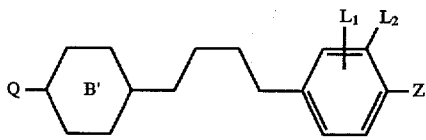

wherein $L_1$, $L_2$ and Z are, respectively, as defined with respect to the formula (I), Q is as defined in the formula (1) and represents a halogen atom, an alkoxy group preferably having from 1 to 4 carbon atoms, a methanesulfonyloxy group, a benzenesulfonyloxy group, a p-toluenesulfonyloxy group or a trifluoromethanesulfonyloxy group.

(e) Another process for preparing the compound of the formula (I) comprises:

reacting an organometallic compound of the following formula (8)

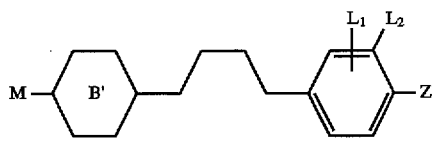

wherein M represents Li, MgP or ZnP wherein P is a halogen such as Cl, Br or I, with a compound of the following general formula (9)

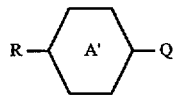

wherein Q represents a halogen atom, an alkoxy group preferably having from 1 to 4 carbon atoms, a methanesulfonyloxy group, a benzenesulfonyloxy group, a p-toluenesulfonyloxy group or a trifluoromethanesulfonyloxy group as defined hereinbefore.

Likewise, the compound of the general formula (II) can be prepared according to the following processes (a') to (e') wherein R, $L_1$, $L_2$, Z, n, M, Q,

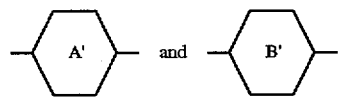

defined in the foregoing formulas may not be defined again.

(a') The compound of the formula (II) is prepared by a process which comprises:

reacting an organometallic compound of the general formula, R-M, with a compound of the following general formula (10)

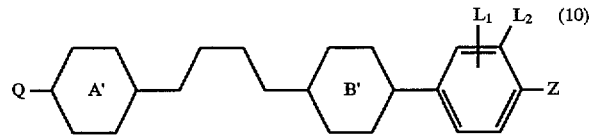

(b') Another process comprises:

reacting an organometallic compound of the following formula (11)

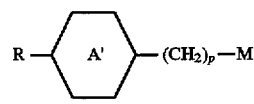

wherein M represents Li, MgP or ZnP in which P represents a halogen, with a compound of the following general formula (12)

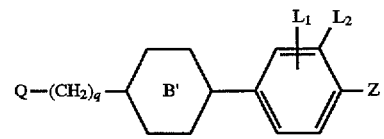

wherein p and q are, respectively, a value of 0, 1, 2, 3 or 4 provided that (p+q) is 4.

(c') A further process comprises:

reacting an organometallic compound of the following formula (13)

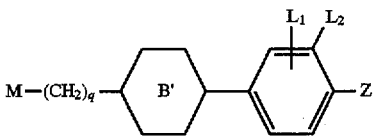

with a compound of the following general formula (14)

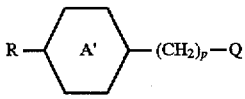

wherein p and q are, respectively, a value of 0, 1, 2, 3, or 4 provided that (p+q) is 4.

(d') A still further process comprises:

reacting an organometallic compound of the following formula (15)

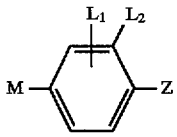

with a compound of the following general formula (16)

(e') Another process comprises:

reacting an organometallic compound of the following formula (17)

wherein M' represents MgP or ZnP in which P represents a halogen atom, preferably Cl, Br or I, or $B(OY_1)_2$ in which $Y_1$ represents hydrogen or an alkyl group having from 1 to 6 carbon atoms, with a compound of the following formula (18)

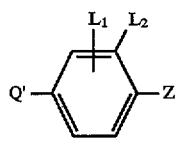

If the silacyclohexane compounds obtained by these processes (a) to (e) and (a') to (e') have a moiety or moieties having the following a structural formula, i.e. a phenyl or tolyl group is attached to the silicon atom at the 1 or 4 position,

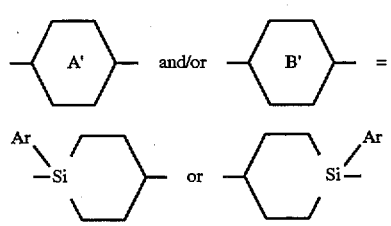

the compound is de-silylated with an electrophilic reagent, such as iodine monochloride, to provide a moiety of the following formula

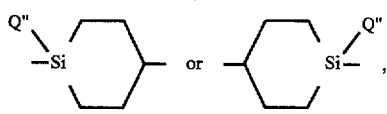

wherein Q" represents Cl, Br or I, for conversion into the moieties of the following formulas

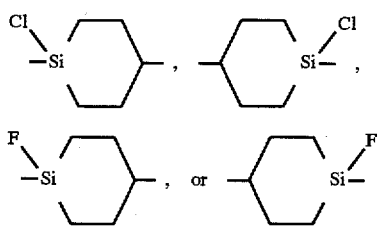

Moreover, these moieties may be further converted into ones of the following formulas

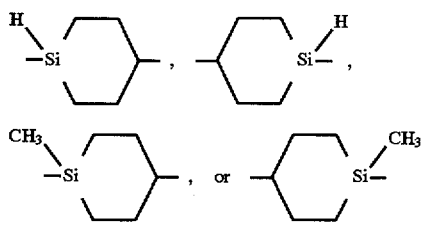

Thus, hydrosilacyclohexane, fluorosilacyclohexane, chlorosilacyclohexane and methylated silacyclohexane compounds of the general formula (I) or (II).

The invention also provides a liquid crystal composition which comprises the silacyclohexane compound of the formula (I) and/or (II). Preferably, the silacyclohexane compound (I) and/or (II) is present in amounts of from 1 to 50 mole %, preferably 5 to 30 mole % of the composition. Moreover, the invention provides a liquid crystal display device comprising a cell structure which comprises the liquid crystal composition mentioned above. The cell structure may be one which is known in the art.

The compounds of both formulas (I) and (II) have the ring structure having an Si atom therein. On comparison with known liquid crystal compounds which have a cyclohexyl ring-cyclohexyl ring-butylene-phenyl ring (QCCP) structure or a cyclohexyl ring-butylene-phenyl ring (QPCH) structure, the compounds of the invention exhibit a nematic liquid crystal phase which is extended to a lower temperature, thus with the following improvements in characteristic properties.

(1) The compounds of the invention can effectively reduce the viscosity of the resultant composition, and can improve a response speed in a low temperature range.

(2) The compounds of the invention contribute to improving the miscibility with other constituents at low temperatures.

Moreover, with the compounds of the fore, as (I) and (II) wherein Z is a substituent other than R or OR, they function to lower a threshold voltage because of the great dielectric anisotropy thereof, along with the characteristic properties mentioned above.

The liquid crystal compounds of the formulas (I) and (II) can be widely employed as a base material which constitutes a main constituent for liquid crystal phase, like the known QCCP structure or QPCH structure having similar hydrocarbon rings. The compounds of the general formulas (I) and (II), wherein Z represents R or OR, exhibit a dielectric anisotropy close to zero. Hence, it is preferred that these compounds are employed as a liquid crystal phase of display devices based on the dynamic scattering (DS) type or the type of deformation of aligned phase (DAP type). On the other hand, the compounds of the formulas (I) and (II) wherein Z is a substituent other than R or OR are preferably used to prepare a liquid crystal phase having a great positive dielectric anisotropy which is appropriately employed in twisted nematic cells or in display devices based on the cholesteric-nematic phase transition.

DETAILED DESCRIPTION OF THE INVENTION

The novel compounds of the invention serving as a liquid crystal are those of the formulas (I) and (II) indicated hereinbefore. More specifically, the compounds have novel ring structures including a trans-1-silacyclohexane ring and/or a trans-4-silacyclohexane ring and include, for example, the compounds of the following formulas (Ia) to (Ij) and (IIa) to (IIh):

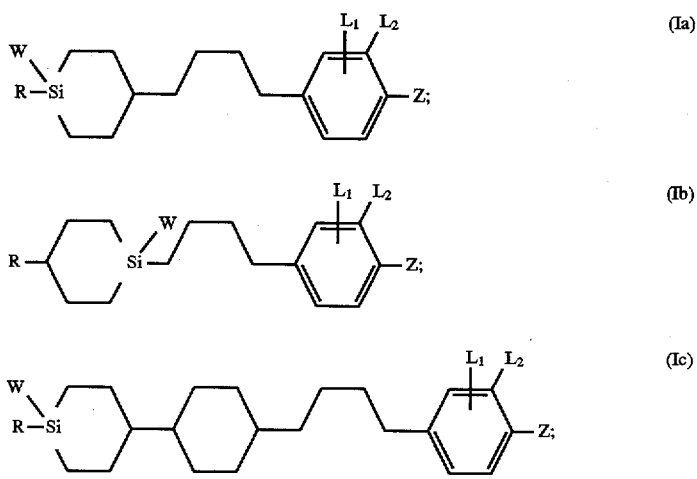

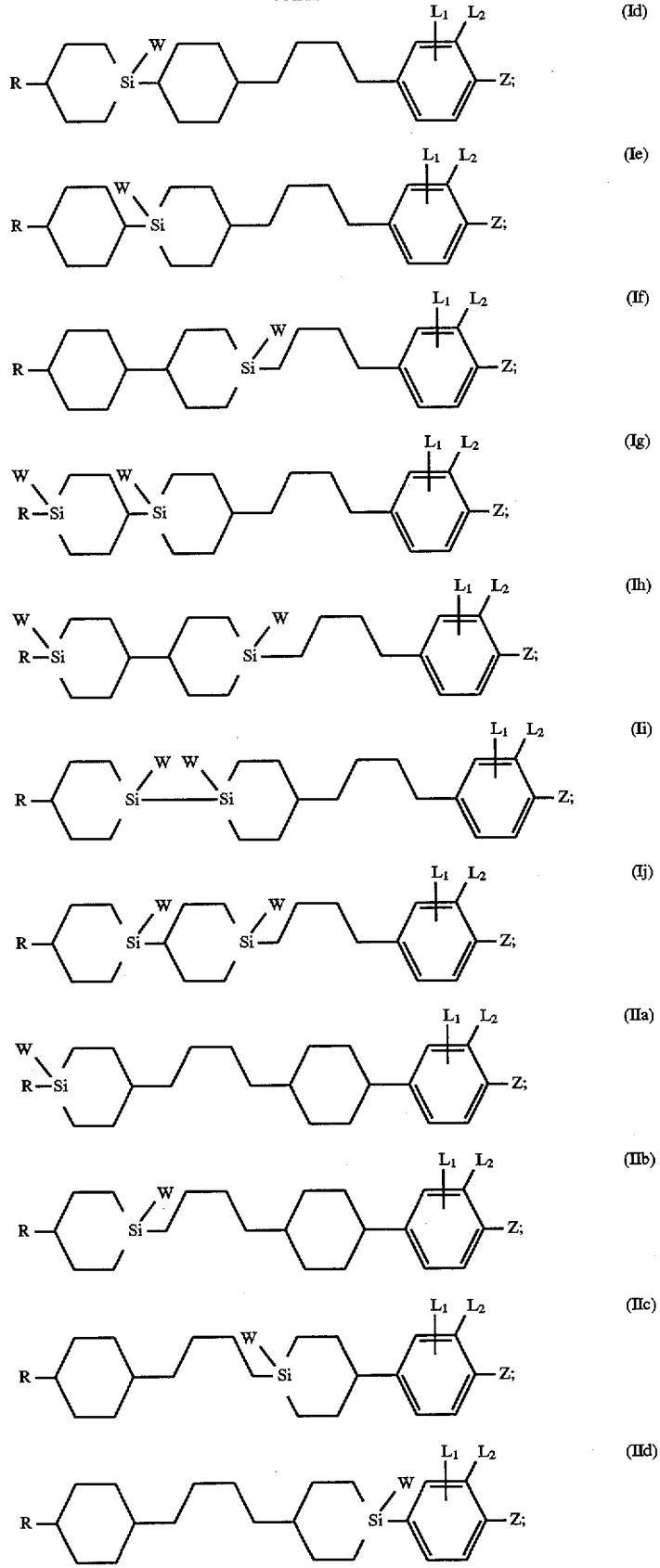

-continued

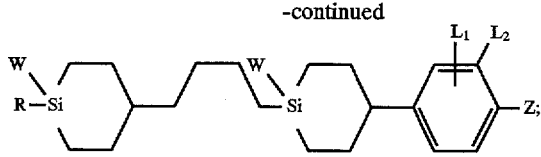 (IIe)

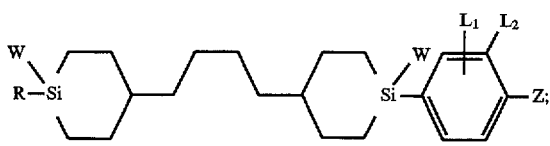 (IIf)

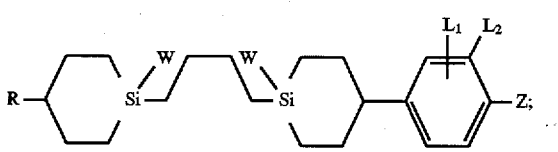 (IIg)

and

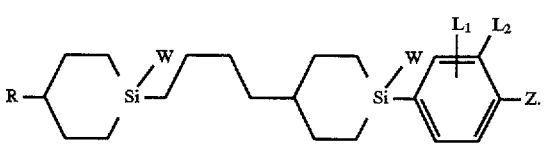 (IIh)

In the formulas (Ia) to (Ij) and (IIa) to (IIh), R represents a linear alkyl group having from 1 to 10 carbon atoms, a branched alkyl group having from 3 to 8 carbon atoms, a mono or difluoroalkyl group having from 1 to 10 carbon atoms, an alkoxyalkyl group having from 2 to 7 carbon atoms or an alkenyl group having from 2 to 8 carbon atoms, Z represents R or OR, in which R is as defined above, CN, F, Cl, $CF_3$, $CClF_2$, $CHClF$, $OCF_3$, $OCClF_2$, $OCHClF$, $OCHF_2$, $(O)_m CY=CX_1X_2$ wherein m is 0 or 1, Y and $X_1$ independently represent H, F or Cl, $X_2$ represents F or Cl, or $O(CH_2)_r(CF_2)_s X_3$ wherein r and s are, respectively, 0, 1 or 2 provided that (r+s)=2, 3 or 4, and $X_3$ represents H, F or Cl, each W represents H, F, Cl or $CH_3$, and $L_1$ represents H or F, and $L_2$ represents H, F or Cl.

It should be noted that the intermediate compounds as represented by the formulas (Ia) to (Ij) and (IIa) to (IIh) wherein W is phenyl or tolyl are not liquid crystal compounds but within a scope of the invention as species of the compounds of the formulas (III) and (IV).

Specific examples of the linear alkyl group having from 1 to 10 carbon and represented by R include methyl, ethyl, n-propyl, n-butyl, n-pentyl, n-hexyl, n-heptyl, n-octyl, n-nonyl and n-decyl.

Specific examples of the mono or difluoroalkyl group having from 1 to 10 carbon atoms and represented by R include fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorooctyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl, and 10,10-difluorodecyl.

Specific examples of the branched alkyl group having 3 to 8 carbon atoms and represented by R include isopropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl and 3-methylheptyl.

Specific examples of the alkoxyalkyl group having from 2 to 7 carbon atoms and represented by R include methoxymethyl, ethoxymethyl, propoxymethyl, butoxymethyl, pentoxymethyl, hexyloxymethyl, methoxyethyl, ethoxyethyl, propoxyethyl, butoxyethyl, methoxypropyl, ethoxypropyl, propoxypropyl, butoxypropyl, methoxybutyl, ethoxybutyl, propoxybutyl, methoxypentyl, ethoxypentyl, and methoxyhexyl.

Specific examples of the alkenyl group having from 2 to 8 carbon atoms and represented by R include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl.

The silacyclohexane compounds of the formulas (I) and (II) essentially have the moiety of the following formula (19)

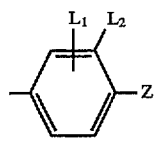
(19)
Specific examples of the moiety include residues of the following formulas
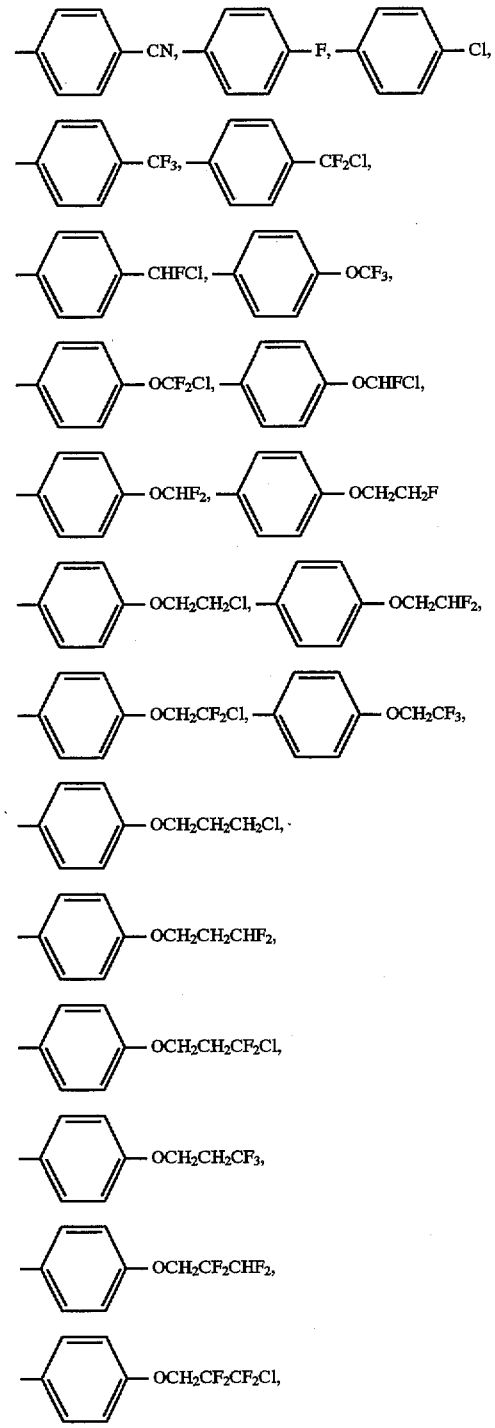

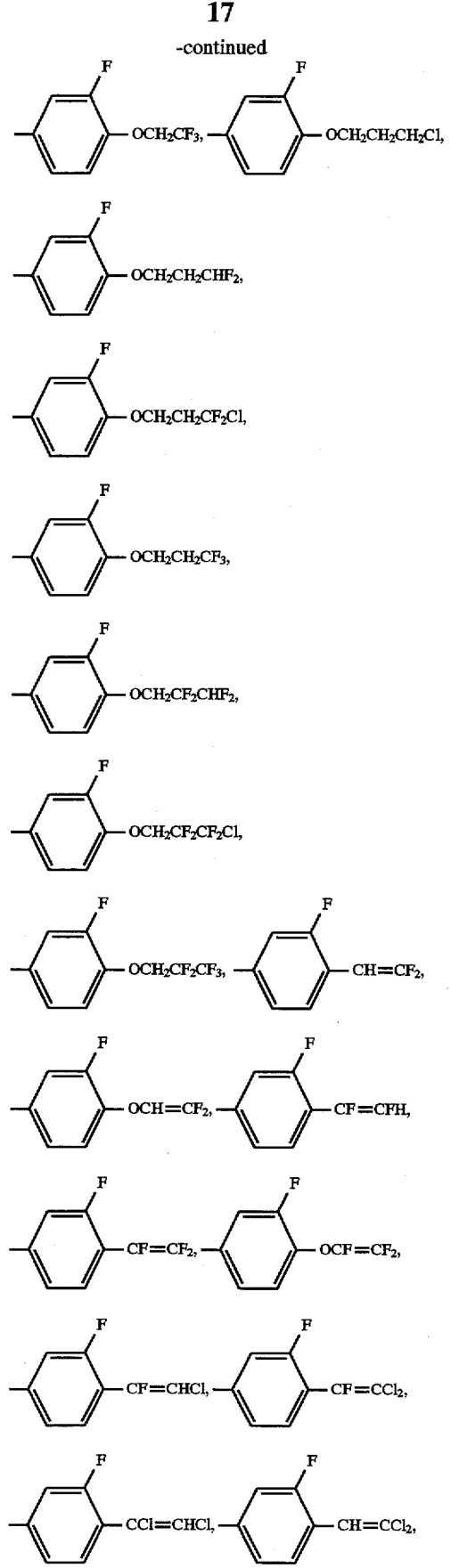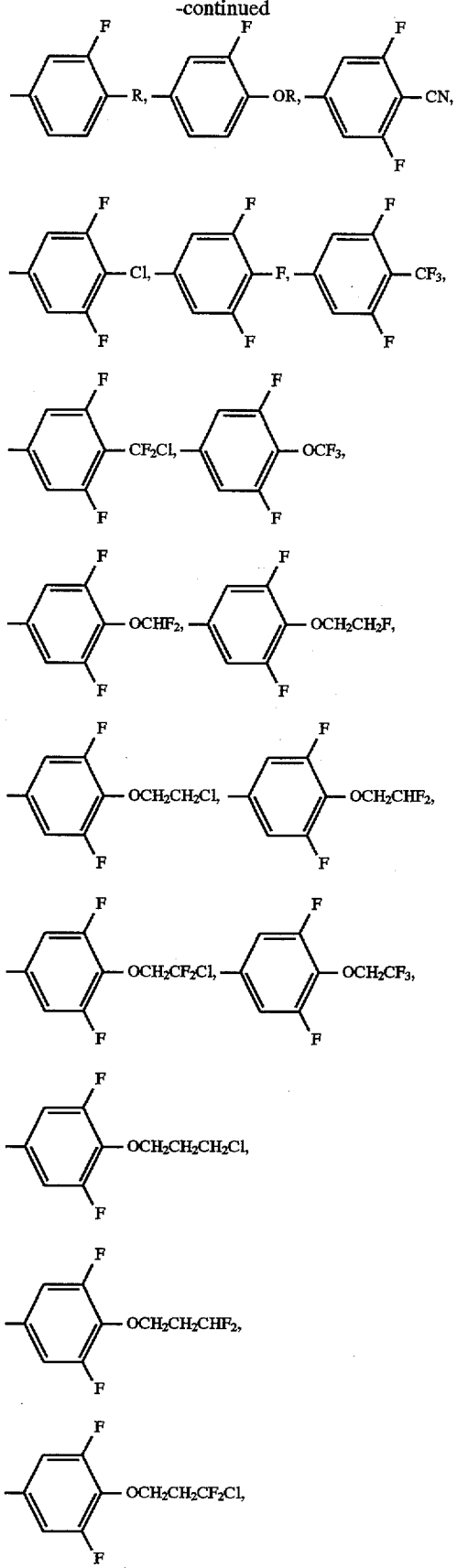

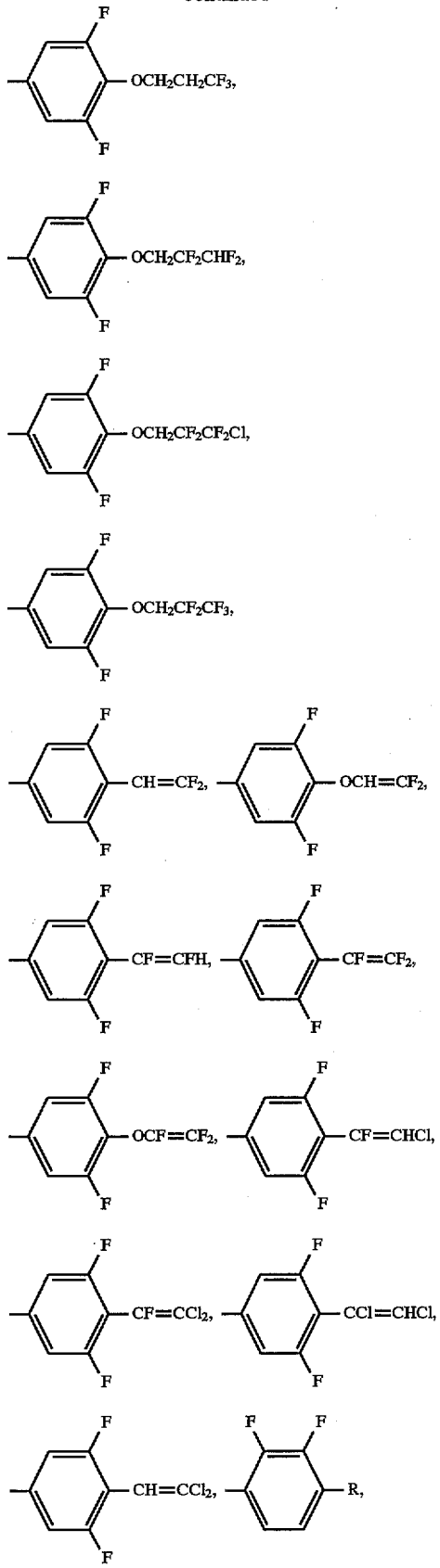

-continued

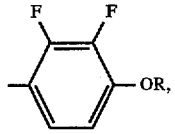

Preferred silacyclohexane compounds include those of the aforeindicated formulas (Ia), (Ic), (Ie), (Ig), (IIa), (IIc) and (IIe) shown below:

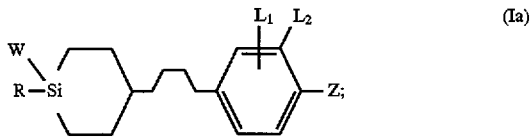

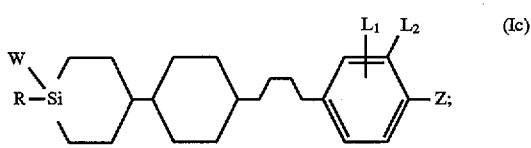

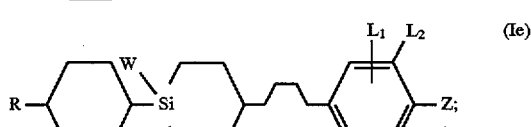

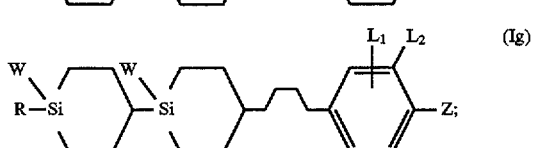

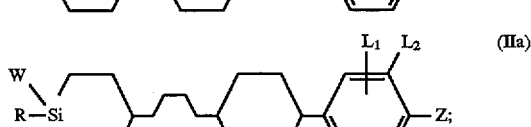

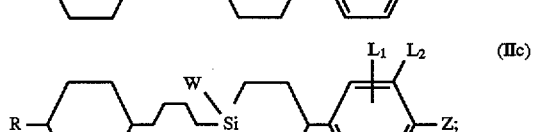

and

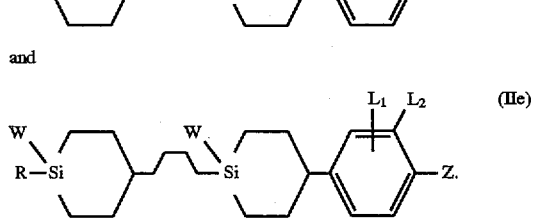

Preferred groups represented by R include: linear alkyl groups having from 2 to 7 carbon atoms, e.g. ethyl, n-propyl, n-butyl, n-pentyl, n-hexyl and n-heptyl; mono or difluoroalkyl groups having from 2 to 7 carbon atoms, such as 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoropentyl, 5-fluorohexyl, 5-fluoroheptyl, 6-fluorohexyl, 6-fluoroheptyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl and 7,7-difluoroheptyl; branched alkyl groups having from 3 to 8 carbon atoms, such as isopropyl, 1-methylpropyl, 2-methylpropyl, 1-methylbutyl, 2-methylbutyl, 3-methylbutyl, 1-methylpentyl, 2-methylpentyl and 2-ethylhexyl; alkoxyalkyl groups having from 2 to 6 carbon atoms, such as methoxymethyl, methoxyethyl, methoxypropyl, methoxypentyl, ethoxymethyl, ethoxyethyl, propoxymethyl and pentoxymethyl; and alkenyl groups having from 2 to 8 carbon atoms, such as vinyl group, 1-propenyl group, 3-butenyl group, 1-pentenyl group, 3-pentenyl group, 4-pentenyl group, 1-hexenyl group, 5-hexenyl group, 6-heptenyl group and 7-octenyl group.

Preferred atoms or groups represented by W include H, F or $CH_3$.

Preferred moieties represented by the formula (19)

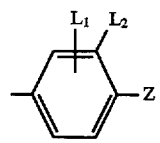

are those indicated below

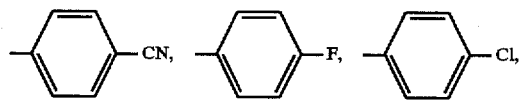

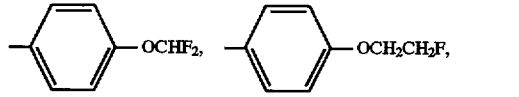

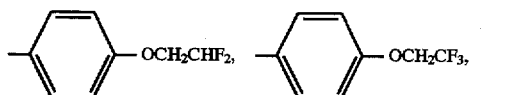

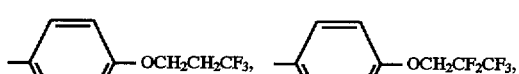

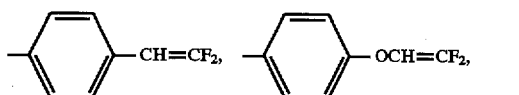

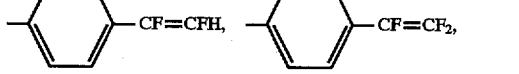

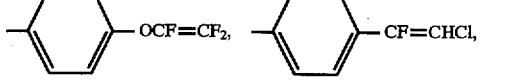

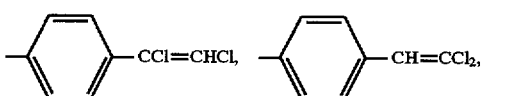

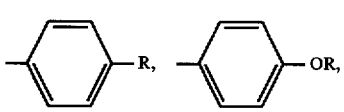

-continued

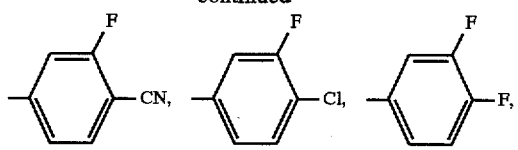

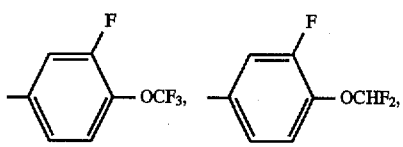

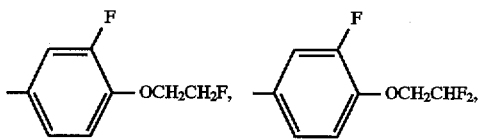

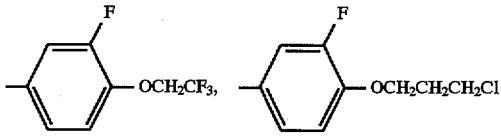

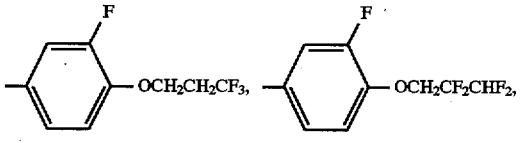

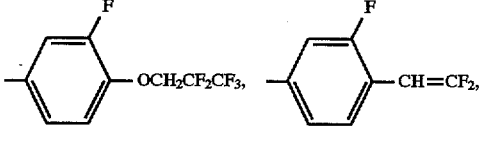

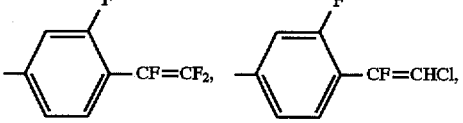

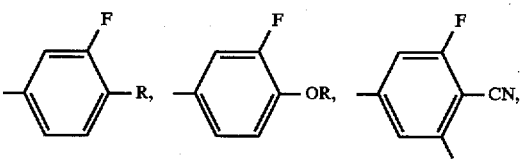

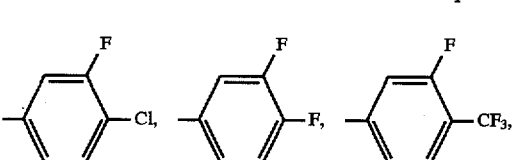

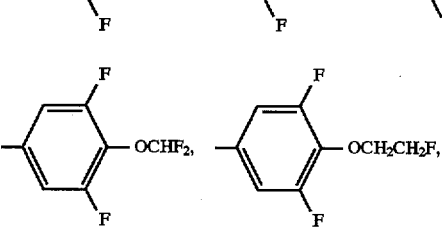

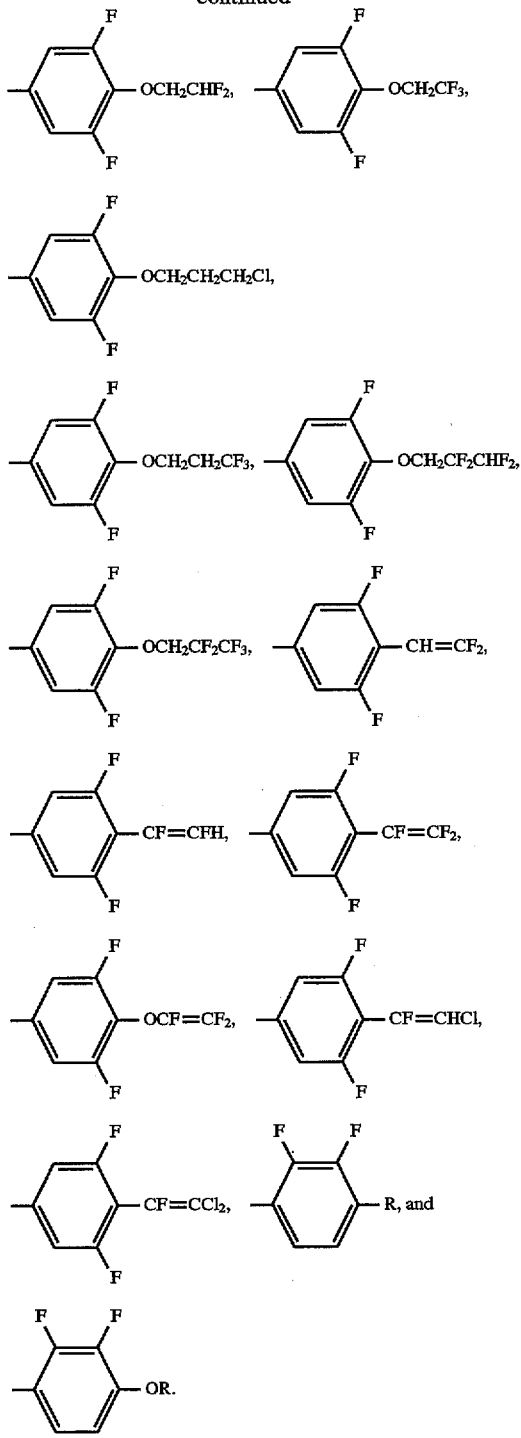

The silacyclohexane compounds of the general formulas (I) and (II) are prepared through carbon—carbon bonding or carbon—silicon bonding reaction between organometallic compounds or reagents and compounds having an eliminable group such as a halogen atom, a lower alkoxy group, a methanesulfonyloxy group, a benzenesulfonyloxy group, a p-toluenesulfonyloxy group or a trifluoromethanesulfonyloxy group.

The preparation of the silacyclohexane compounds of the formula (I) according to the invention is first described.

(a) An organometallic reagent or compound of the formula, R-M, wherein M represents Li, MgP or ZnP wherein P is a halogen atom, preferably Cl, Br or I, and R is as defined hereinbefore, is reacted with a compound of the following general formula (1)

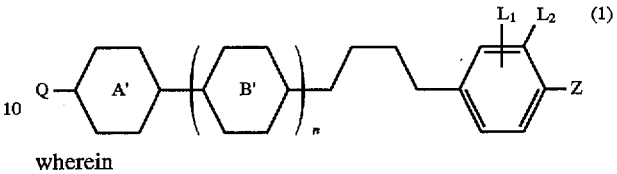

wherein

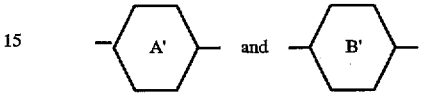

independently represent

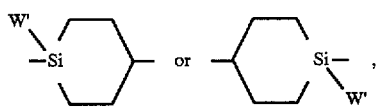

in which W' represents H, methyl, phenyl or tolyl, $L_1$, $L_2$, Z and n are, respectively, ad efined in the formula (I) or (II), and Q represents a halogen atom, an alkoxy group preferably having from 1 to 4 carbon atoms, a methanesulfonyloxy group, a benzenesulfonyloxy group, a p-toluenesulfonyloxy group or a trifluoromethanesulfonyloxy group. Especially, when

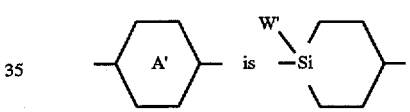

in which W' represents F, Cl, phenyl or tolyl, and Q is a halogen atom or an alkoxy group having from 1 to 4 carbon atoms, e.g. Cl, Br, $OCH_3$ or $OCH_2CH_3$, the carbon—silicon bonding reaction proceeds readily. Thus, an intended product can be obtained in high yield. Thus, such a combination as set out above is preferred. The reaction of (a) is conducted under conditions of a temperature preferably ranging from 0° to 150° C. for a time of from 1 to 5 hours. On the other hand,

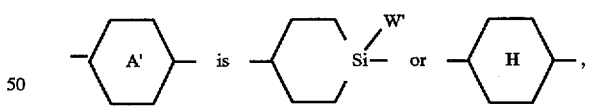

the carbon—carbon bonding reaction is caused to proceed in the presence of a copper salt. Examples of the copper salt include copper (I) salts such as copper (I) chloride, copper (I) bromide, copper (I) iodide, copper (I) cyanide and the like, and copper (II) salts such as copper (II) chloride, copper (II) bromide, copper (II) iodide, copper (II) acetate and the like. Besides, copper complexes such as dilithium tetrachlorocuprate may also be used. In the case, Q in the formula (1) should preferably be a halogen atom, or a methanesulfonyloxy group, a benzenesulfonyloxy group, a p-toluenesulfonyloxy group or a trifluoromethanesulfonyloxy group. More preferably, Q is Br or I. By this, a higher yield of an intended product is expected.

This reaction is usually carried out in a solvent such as ethyl ether, tetrahydrofuran, dimethoxyethane, diglyme or the like.

The preparation of the starting compound of the formula (1) is described for different types of compounds.

(1a)
Preparation of

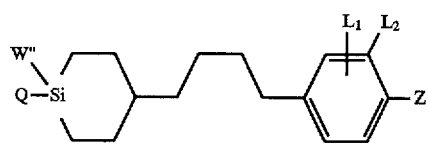

wherein W'" is H or methyl.

The above compound can be prepared from an aldehyde according to the following reaction sequence.

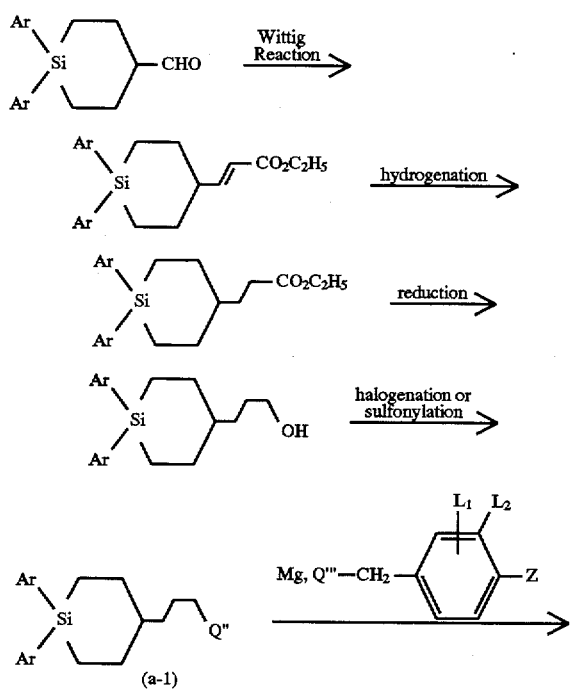

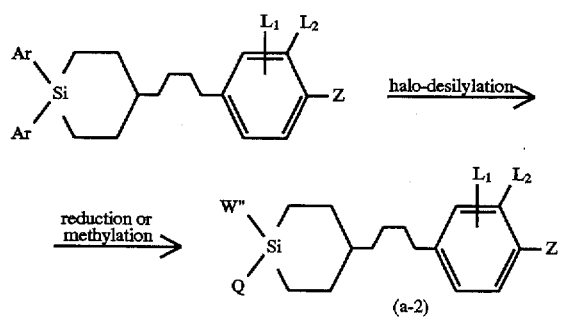

The starting aldehyde compound is set out, for example, in Japanese Patent Application No. 6-123208, filed May 11, 1994, now U.S. Pat. No. 5,527,490. The series of the reactions are not specific and may be conducted in a manner known in the art. It will be noted that in the above reaction sequence, Ar is phenyl or tolyl, Q, Q" and Q'" are, respectively, bromine or iodine, W'" is H or methyl, and Z, $L_1$ and $L_2$ are, respectively, as defined hereinbefore.

(1b)

Preparation of

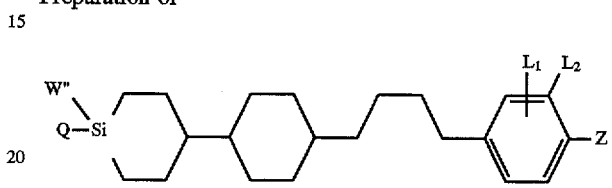

wherein W'" is H or methyl.

This compound is prepared in the same manner as in (a) using a starting aldehyde of the following formula

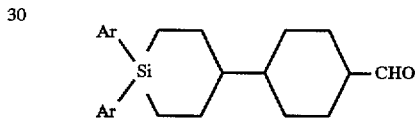

The aldehyde compound is set out, for example, in Japanese Patent Application No. 6-182904, filed Jul. 12, 1994, now U.S. Pat. No. 5,519,156.

(1c)

Preparation of

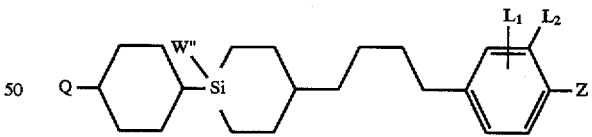

wherein W'" is H or methyl.

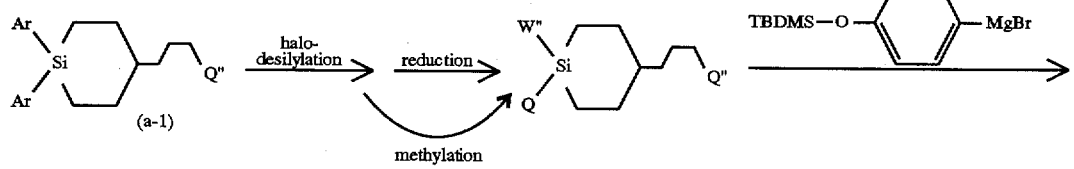

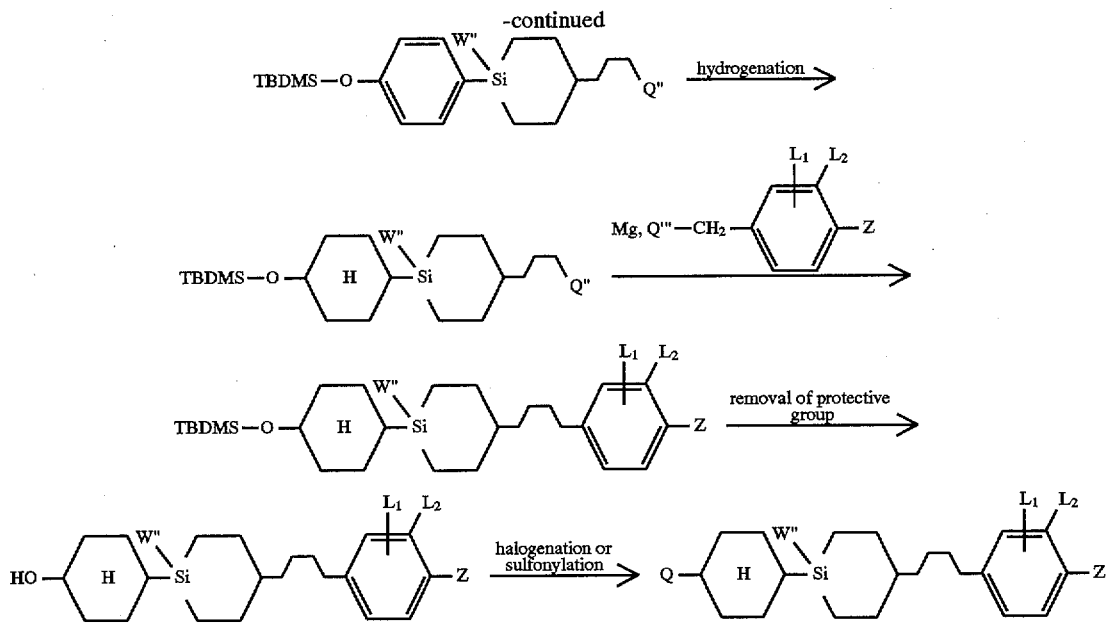
In the above reaction sequence, TBDMS is a t-butyldimethylsilyl protective group represented by t-$(C_4H_9)(CH_3)_2$Si—. The compound (a-1) is prepared in the same manner as in (1a).
(1d) Preparation of
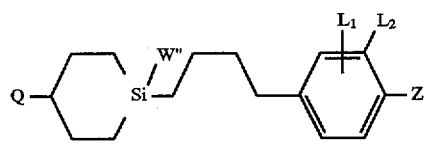
This compound is prepared from a ketone according to the following reaction sequence.
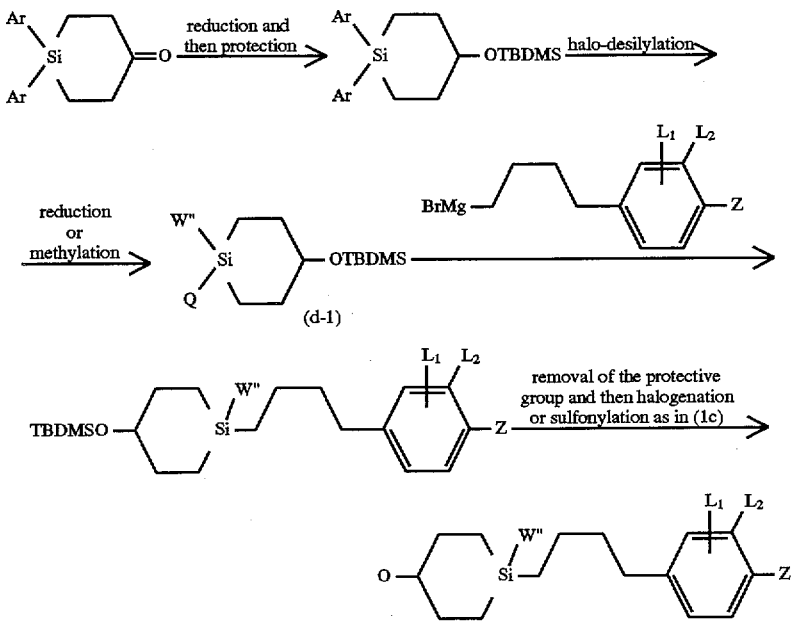

The starting ketone compound is set out, for example, in Japanese Patent Application No. 6-78125, filed Mar. 24, 1994 (corresponding to U.S. patent application Ser. No. 08/408961, filed Mar. 23, 1995).

(1e) Preparation of

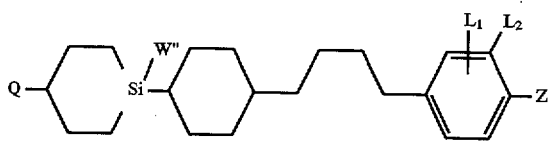

This compound is prepared using the compound (d-1) above according to the following reaction sequence.

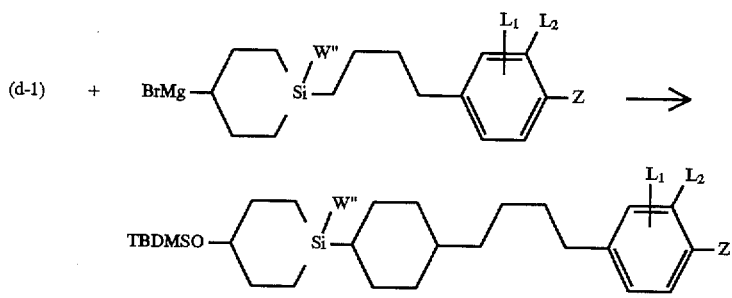

Thereafter, the above compound is subjected to the removal of the protective group and halogenated or sulfonylated in the same manner as in (d) to obtain the captioned compound.

(1f) Preparation of

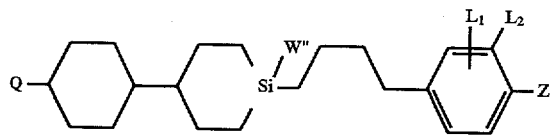

This compound is prepared from a ketone according to the following reaction sequence.

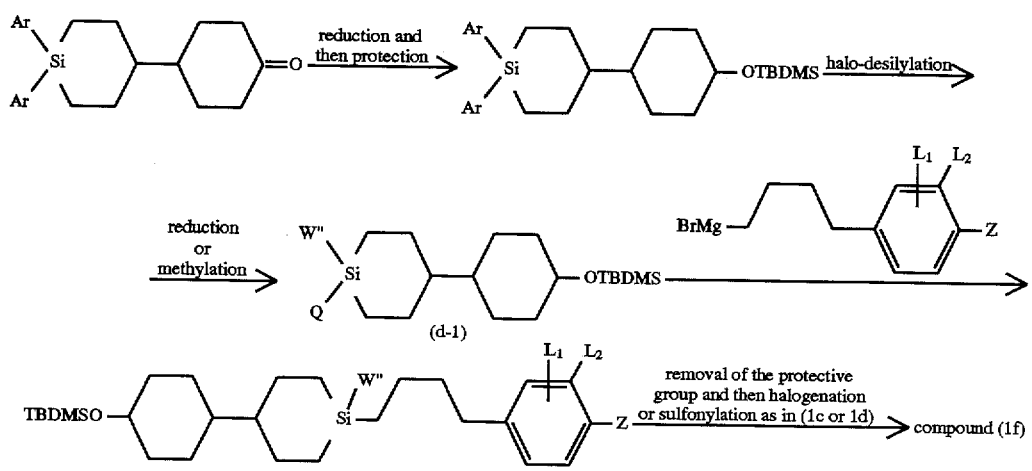

The starting ketone compound is set out, for example, in Japanese Patent Application No. 6-154219, filed Jun. 13, 1994 (corresponding to U.S. patent application Ser. No. 08/483034, filed Jun. 7, 1995).

(b) Alternatively, the compound (I) may be prepared by reaction between an organometallic compound of the following general formula (2)

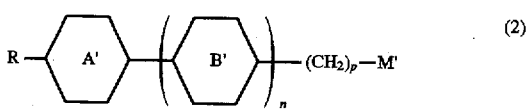

wherein

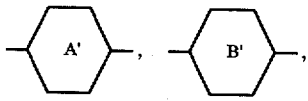

R and n are, respectively, as defined in the foregoing formulas, and M' represents MgP or ZnP wherein P represents a halogen, preferably Cl, Br or I, or $B(OY_1)_2$ wherein $Y_1$ represents H or an alkyl group preferably having from 1 to 4 carbon atoms, with a compound of the following general formula (3)

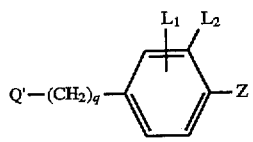 (3)

wherein $L_1$, $L_2$ and Z are, respectively, as defined with respect to the formula (I), Q' is as defined in the formula (1) and represents a halogen atom, a methanesulfonyloxy group, a benzenesulfonyloxy group, a p-toluenesulfonyloxy group or a trifluoromethanesulfonyloxy group, p in the formula (2) and q are, respectively, a value of 0, 1, 2, 3 or 4 provided that (p+q) is 4.

In the reaction, when q=0 and p=4, the reaction is carried out in the presence of a transition metal catalyst. Preferably, palladium compounds or nickel compounds are used as the catalyst. Examples of the tetrakis(triphenylphosphine) palladium (0), di(1,2-bis(diphenylphosphino)ethane) palladium (0), bis(dibenzylideneacetone) palladium (0), [1,1'-bis(diphenylphosphino)ferrocene] palladium (II) chloride, and the like. Examples of the nickel catalyst include (1,3-bis(diphenylphosphino)propane) nickel (II) chloride, (1,2-bis(diphenylphosphino)ethane) nickel (II) chloride, bis(triphenylphosphine) nickel (II) chloride and the like.

Q is preferably Br or I because an intended product is obtained in higher yield. The reaction is preferably conducted under conditions of a temperature of 0° to 150° C. for a time of 1 to 5 hours in a solvent as used in (a).

The starting compound of the formula (2) may be prepared in the following manner for different types of compounds. It should be noted that in this preparation, a halogen is attached to as P and the conversion of P to M' in the formula (2) can be readily conducted by any of ordinary procedures known in the art.

(2a)
Preparation of

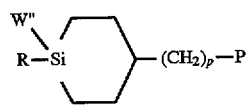

wherein P=Cl, Br or I.

p = 0

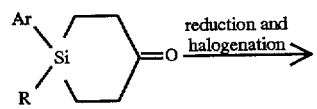

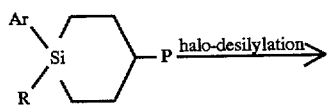

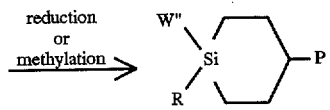

p = 1

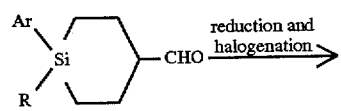

p = 2

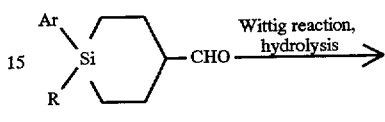

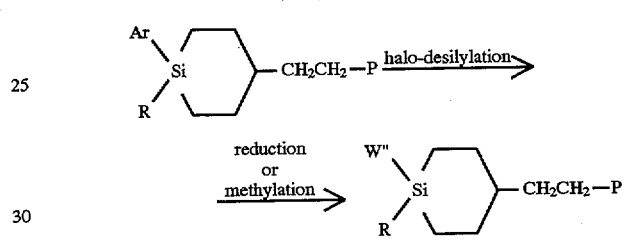

(2a-1)

p = 3

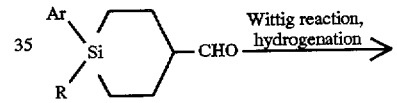

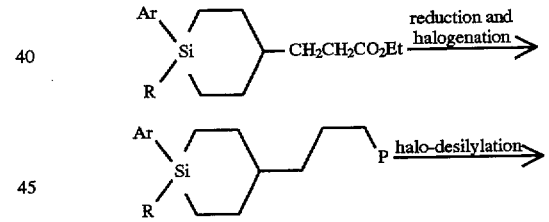

p = 4 compound of (2a-1) Wittig reaction, hydrogenation →

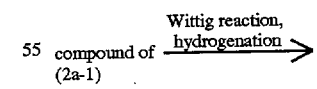

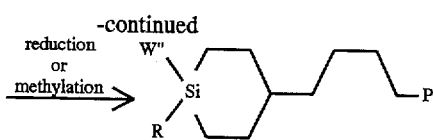

(2b)

Preparation of

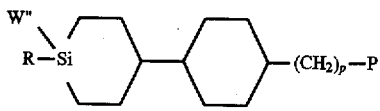

These types of compounds are prepared from ketone and aldehyde compounds in the same manner as in (2a) using

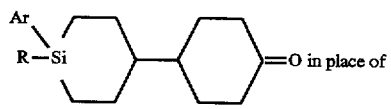 in place of

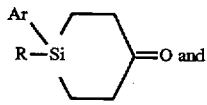  and

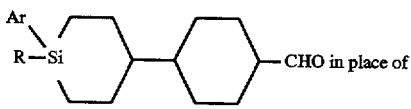 CHO in place of

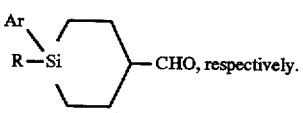 CHO, respectively.

(2c)

Preparation of

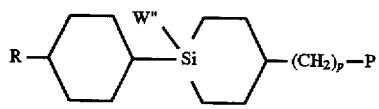

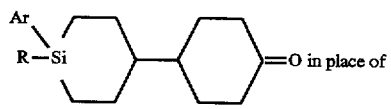=O is reacted in a manner similar to (2a) to obtain 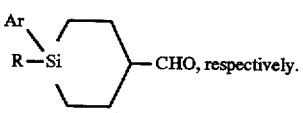—(CH$_2$)$_p$—P, followed by halo-desilylation, reaction with R—⬡—MgBr and then reduction or methylation to obtain the captioned compound.

(2d)

Preparation of

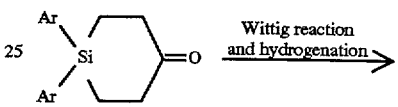

p = 0

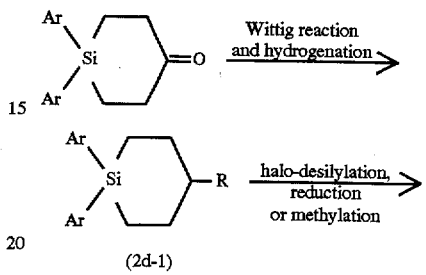

$p \neq 0$

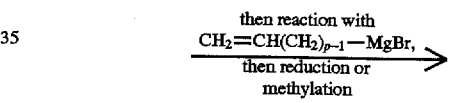

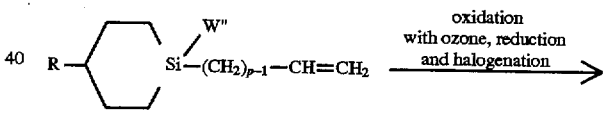

then reaction with
CH$_2$=CH(CH$_2$)$_{p-1}$—MgBr,
then reduction or methylation

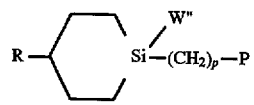

oxidation with ozone, reduction and halogenation

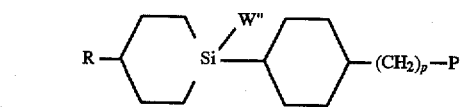

(2e)

Preparation of

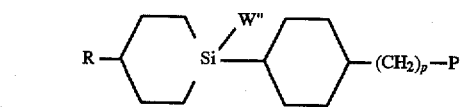

Compound of (2d-1) — halo-desilylation then reaction with →

BrMg—⬡—(CH$_2$)$_p$-OTBDMS reduction or methylation →

-continued

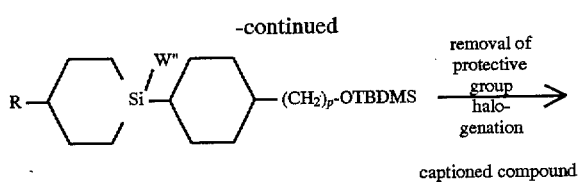

(2f)
Preparation of

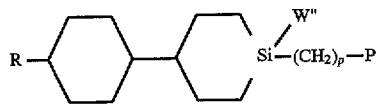

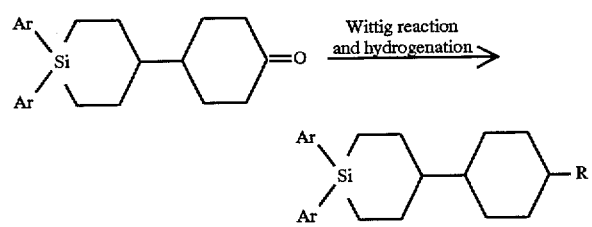

Then, the hydrogenated product is halo-desilylated, followed by the procedure of (2d) to obtain the captioned compound.

(c) The compound (I) may also be prepared by reaction between the organometallic compound of the following general formula (4)

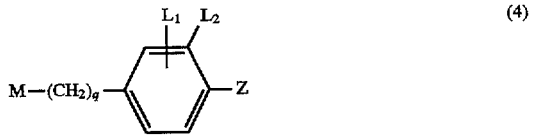

wherein $L_1$, $L_2$, and Z are, respectively, as defined in the formula (I), and M represents Li, MgP or ZnP wherein P is a halogen as defined hereinabove, with a compound of the following general formula (5)

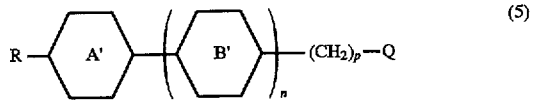

wherein

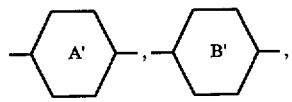

R and n are, respectively, as defined in the foregoing formulas, Q is as defined in the formula (2), and p and q are, respectively, a value of 0, 1, 2, 3, or 4 provided that (p+q) is 4. This carbon—carbon bonding reaction is carried out in a manner as set out in (a), i.e. the reaction proceeds in the presence of a catalytic amount of copper salts. Such copper salts are those set out in (a) and include, for example, copper (I) salts such as copper (I) chloride, copper (I) bromide, copper (I) iodide, copper (I) cyanide and the like, copper (II) salts such as copper (II) chloride, copper (II) bromide, copper (II) iodide, copper (II) acetate and the like, and copper complexes such as dilithium tetrachlorocuprate. In the case, Q in the formula (5) should preferably be Br, I or a p-toluenesulfonyloxy group, by which a high yield is expected.

The reaction of (c) is conducted under conditions similar to those of (a) above.

The starting compound of the formula (5) may be prepared in a manner similar to (2a) to (2f) directed to the preparation of the compounds of the formula (2).

(d) A still further process for preparing the compound of the formula (I) comprises the reaction between an organometallic compound of the following general formula (6)

with a compound of the following general formula (7)

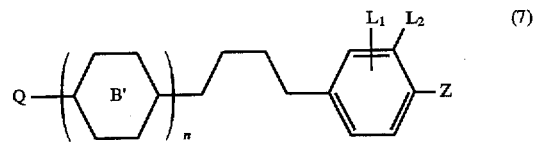

wherein n, $L_1$, $L_2$ and Z are, respectively, as defined with respect to the formula (I), Q is as defined in the formula (1) and represents a halogen atom, an alkoxy group preferably having from 1 to 4 carbon atoms, a methanesulfonyloxy group, a benzenesulfonyloxy group, a p-toluenesulfonyloxy group or a trifluoromethanesulfonyloxy group. In the above reaction, when

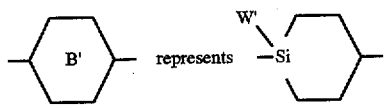

in which W represents H, $CH_3$, phenyl or tolyl, Q should preferably be a halogen atom such as Cl, Br or the like, or an alkoxy group such as $OCH_3$, $OCH_2CH_3$ or the like. By this, the carbon—silicon bonding reaction is caused to proceed readily, resulting in a high yield of intended product. The reaction is preferably conducted under conditions a temperature of from 0° to 150° C. for a time of 1 to 5 hours.

On the other hand, when

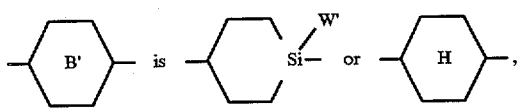

the carbon—carbon bonding reaction is caused to proceed in the presence of a copper salt. Examples of the copper salt include copper (I) salts and copper (II) salts having set out hereinbefore. In the case, Q in the formula (7) should preferably be a halogen atom, or a methanesulfonyloxy group, a benzenesulfonyloxy group, a p-toluenesulfonyloxy group or a trifluoromethanesulfonyloxy group. More preferably, Q is Br, I or a p-toluenesulfonyloxy group. By this, a higher yield of an intended product is expected. This reaction is usually carried out in ethers such as ether, tetrahydrofuran, dioxane and the like, hydrocarbons such as iso-octane, benzene, toluene, xylene and the like, and mixtures thereof.

The starting compound of the formula (7) is prepared in the same manner as in (a-1) for the compound of the following formula

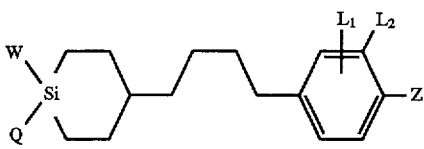

and in the same manner as in (a-4) for the compound of the following formula

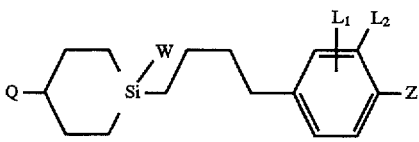

(d) Another process for preparing the compound of the formula (I) comprises the reaction between an organometallic compound of the following formula (8)

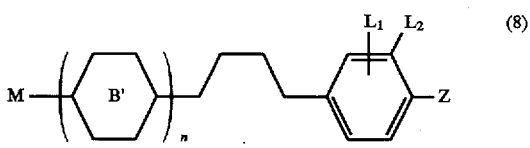

(8)

wherein M represents Li, MgP or ZnP wherein P is a halogen such as Cl, Br or I, with a compound of the following general formula (9)

(9)

wherein R and Q are, respectively, as defined before. In the above reaction, when

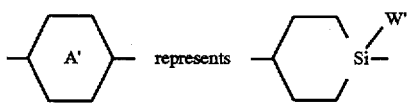

in which W represents H, CH₃, phenyl or tolyl, Q should preferably be a halogen atom such as Cl, Br or the like, or an alkoxy group such as OCH₃, OCH₂CH₃ or the like. By this, the carbon—silicon bonding reaction is caused to proceed readily, resulting in a high yield of intended product. In this case, the reaction is preferably conducted under conditions a temperature of from 0° to 150° C. for a time of 1 to 5 hours.

On the other hand, when

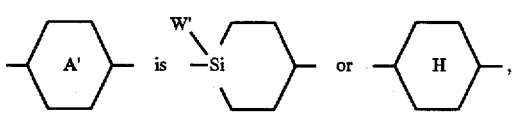

the carbon—carbon bonding reaction is caused to proceed in the presence of a copper salt. Examples of the copper salt include copper (I) salts and copper (II) salts having set out hereinbefore. In the case, Q in the formula (9) should preferably be a halogen atom, or a methanesulfonyloxy group, a benzenesulfonyloxy group, a p-toluenesulfonyloxy group or a trifluoromethanesulfonyloxy group. More preferably, Q is Br or I. By this, a higher yield of an intended product is expected. This reaction is usually carried out in ethers such as ether, tetrahydrofuran, dioxane and the like, hydrocarbons such as iso-octane, benzene, toluene, xylene and the like, and mixtures thereof.

For instance, the starting compound of the formula (8) is prepared in the same manner as in (a-4) set out hereinabove wherein a metal such as Mg is further reacted to provide a compound of the following formula

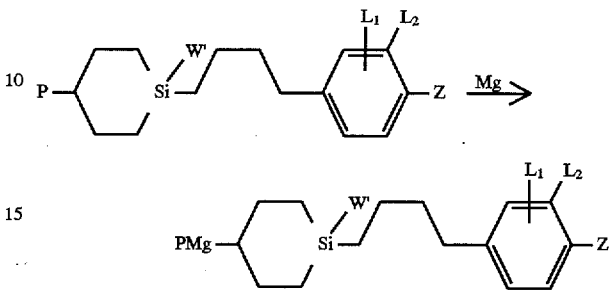

Next, the preparation of the silacyclohexane compound of the general formula (II) is described.

(a') Like the preparation of the compound (I), an organometallic reagent of the formula, R-M, wherein M represents Li, MgP or ZnP wherein P is a halogen atom, preferably Cl, Br, or I, and R is as defined hereinbefore, is reacted with a compound of the general formula (10)

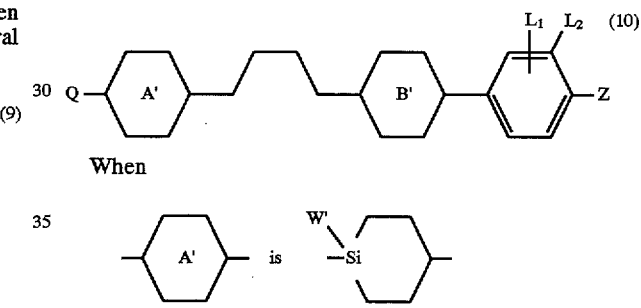

When

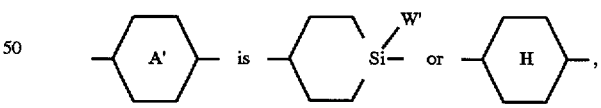

wherein W' is H, CH₃, phenyl or tolyl, Q should preferably be a halogen atom or an alkoxy group. More preferably, Q is Cl, Br, OCH₃ or OCH₂CH₃, by which the carbon—silicon bonding reaction with R-M readily proceeds in high yield. The reaction favorably proceeds under conditions of a temperature preferably ranging from 0° to 150° C. for a time of from 1 to 5 hours.

On the other hand, when the carbon—carbon bonding reaction is caused to proceed in the presence of a copper salt, as defined with respect to the compounds of the formula (I). Q in the formula (10) should preferably be a halogen atom, a methanesulfonyloxy group, a benzenesulfonyloxy group, a p-toluenesulfonyloxy group or a trifluoromethanesulfonyloxy group. More preferably, Q is Br or I. By this, a high yield of an intended product is expected.

This reaction is usually carried out in ethers such as ether, tetrahydrofuran, dioxane and the like, hydrocarbons such as iso-octane, benzene, toluene, xylene and the like, and mixtures thereof.

The starting compounds of the formula (10) may be prepared in the following manner.

(3-a)
Preparation of
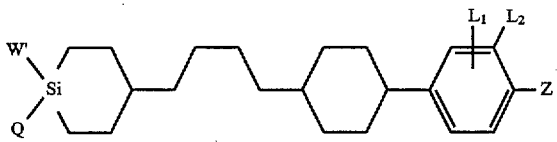
(3-b)
Preparation of
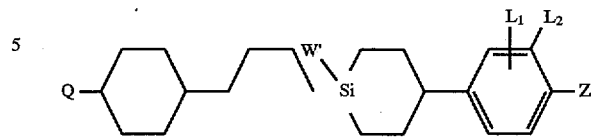
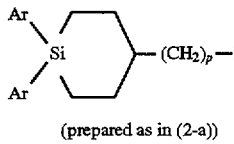
(prepared as in (2-a))
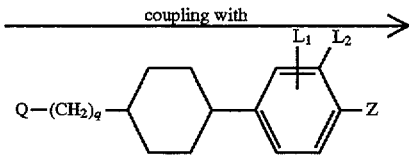
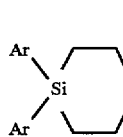
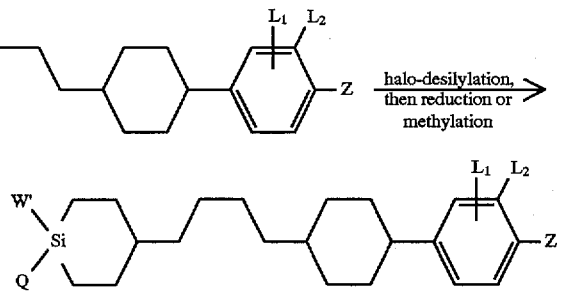
The starting compound in the above reaction sequence is prepared in the same manner as in (2-a) having set out hereinbefore, followed by the procedure as set out above.
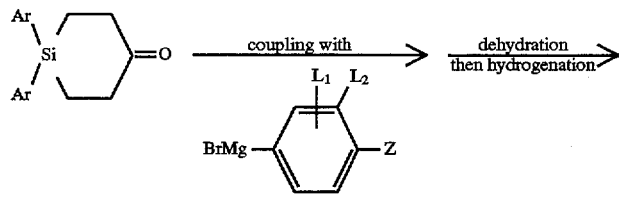
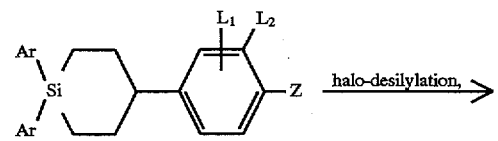
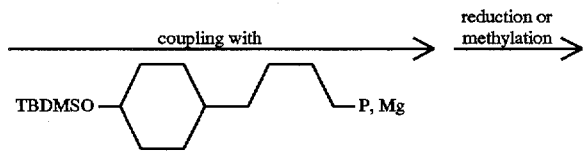
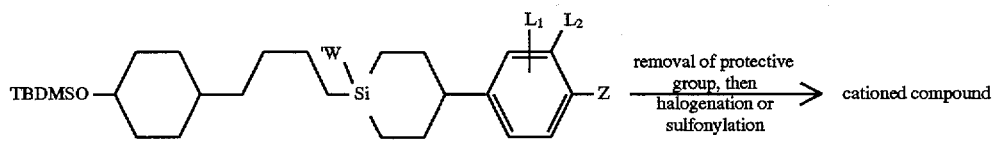

(3-c)
Preparation of
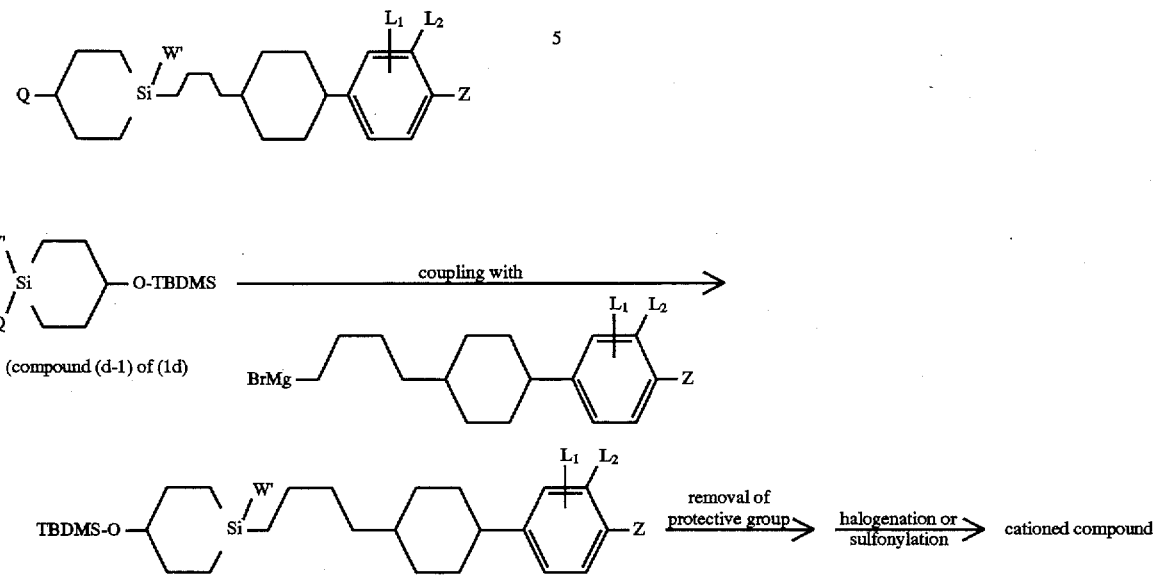
(3-d)
Preparation of
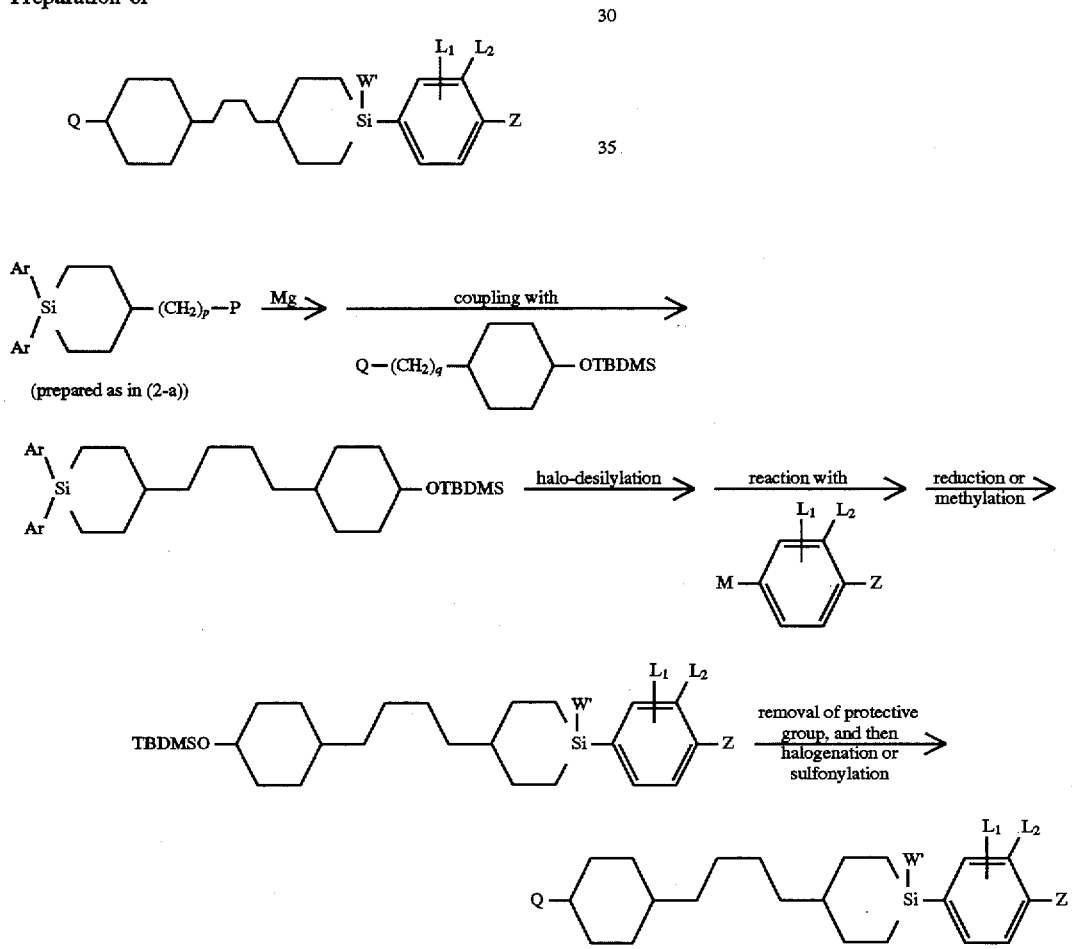

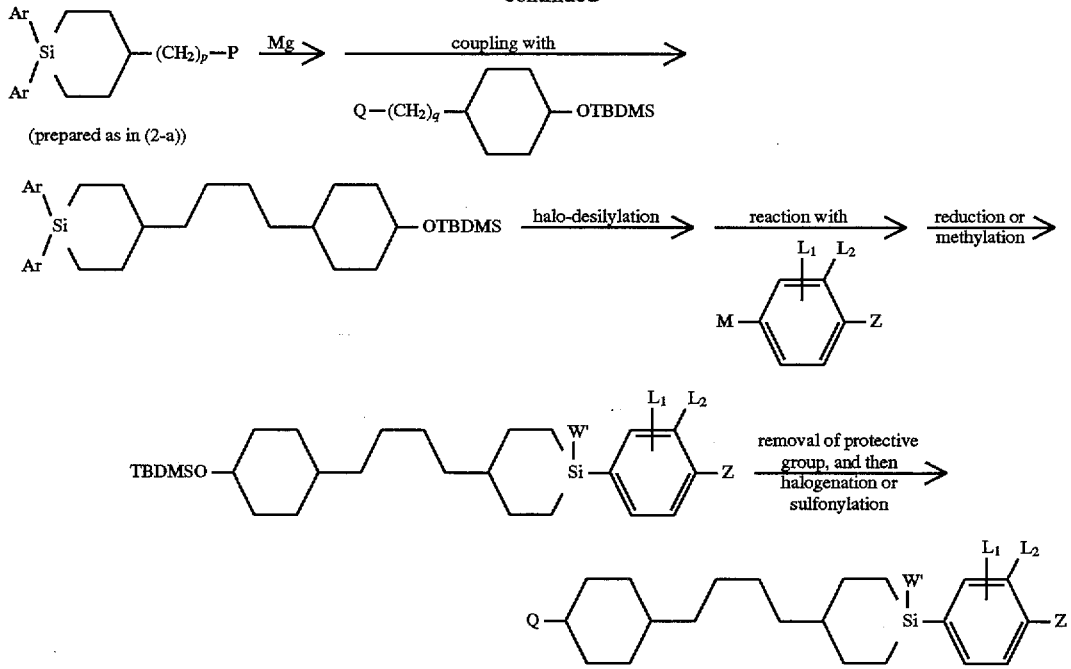

(b') The compound (II) may also be prepared by a process which comprises subjecting the carbon—carbon bonding reaction between an organometallic reagent of the following general formula (11)

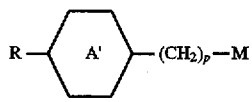

wherein M represents Li, MgP or ZnP as defined before, with a compound of the following general formula (12)

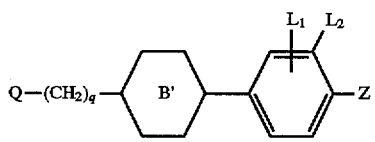

wherein p and q are, respectively, a value of 0, 1, 2, 3 or 4 provided that (p+q) is 4, thereby obtaining a silacyclohexane compound of the general formula (II). This reaction is usually conducted in the presence of a catalytic amount of a copper salt as set out with respect to the compounds (I). Q in the formula (12) is preferably a halogen atom, a methanesulfonyloxy, benzenesulfonyloxy, p-toluenesulfonyloxy, or trifluoromethanesulfonyloxy. More preferably, Br, I or p-toluenesulfonyloxy is used by which a higher yield of an intended product is attained. The reaction conditions may be those for the carbon—carbon bonding reaction for the preparation of the compound (I).

The compound of the formula (12) may be prepared in the following manner.

(4-a)

Preparation of

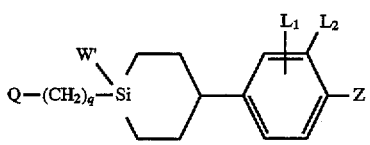

q = 0

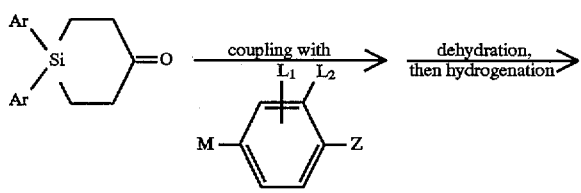

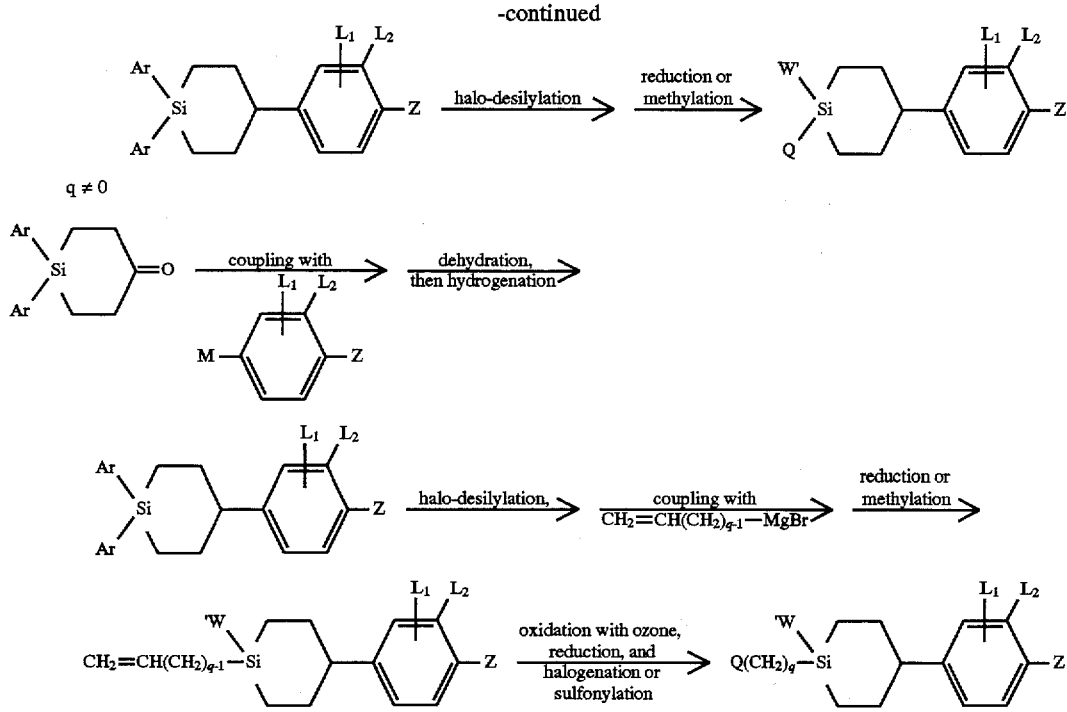

(4-b)
Preparation of

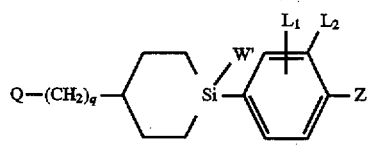

In the same manner as in (2-a) where R=Ar and the compound may be halogenated or sulfonylated, a starting compound of the following formula is prepared

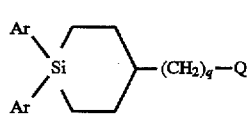

This compound is reacted in the following manner to obtain the intended compound.

(c') Like the procedure (b'), the compound (II) is prepared through carbon—carbon reaction between an organometallic compound of the following formula (13)

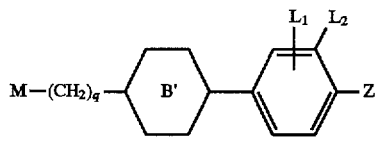

and a compound of the following general formula (14)

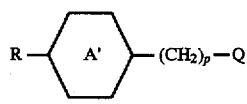

wherein p and q are, respectively, a value of 0, 1, 2, 3, or 4 provided that (p+q) is 4. This reaction may be caused to proceed substantially in the same manner as in (b').

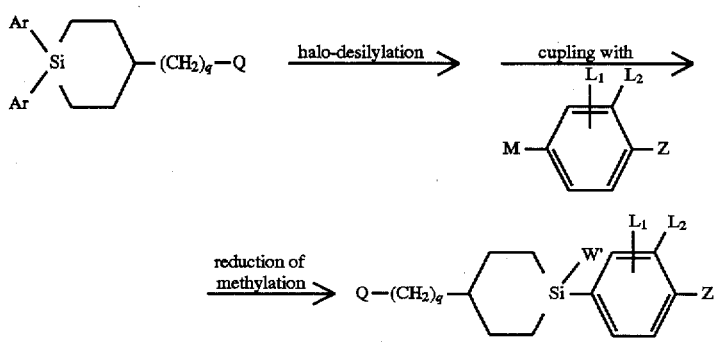

The compound of the formula (12) may be prepared in the same manner as in (4-a) and (4-b) having set out hereinabove.

(d') The compound (II) may further be prepared by reaction between an organometallic compound of the following formula (15)

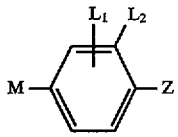
(15)

and a compound of the following general formula (16)

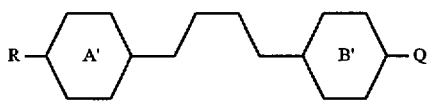
(16)

When

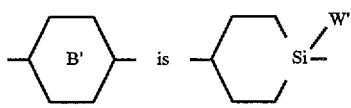

wherein W' is H, CH₃phenyl or tolyl, Q should preferably be a halogen atom or an alkoxy group. More preferably, Q is Cl, Br, OCH₃ or OCH₂CH₃, by which the carbon—silicon bonding reaction with R-M readily proceeds in high yield. The reaction favorably proceeds under conditions of a temperature preferably ranging from 0° to 150° C. for a time of from 1 to 5 hours.

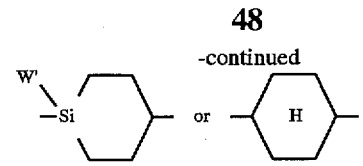

the carbon—carbon bonding reaction is caused to proceed in the presence of a copper salt as defined with respect to the compounds of the formula (I). Q in the formula (10) should preferably be a halogen atom, a methanesulfonyloxy group, a benzenesulfonyloxy group, a p-toluenesulfonyloxy group or a trifluoromethanesulfonyloxy group. More preferably, Q is Br or I. By this, a high yield of an intended product is expected.

This reaction is usually carried out in ethers such as ether, tetrahydrofuran, dioxane and the like, hydrocarbons such as iso-octane, benzene, toluene, xylene and the like, and mixtures thereof.

The starting compound of the formula (16) may be prepared in the following manner.

(5-a)
Preparation of

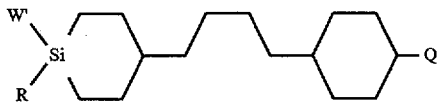

In the same manner as in (2-a), a starting compound of the following formula is prepared

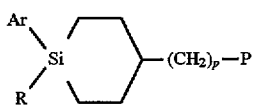

This compound is reacted according to the following reaction sequence to obtain the intended compound

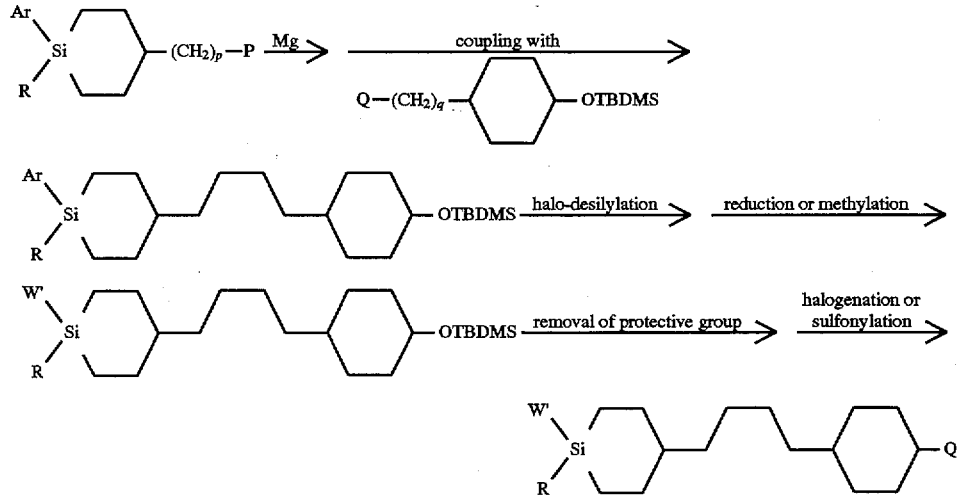

On the other hand, when

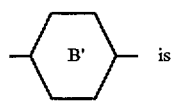 is (5-b)
Preparation of

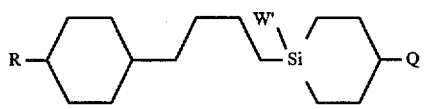

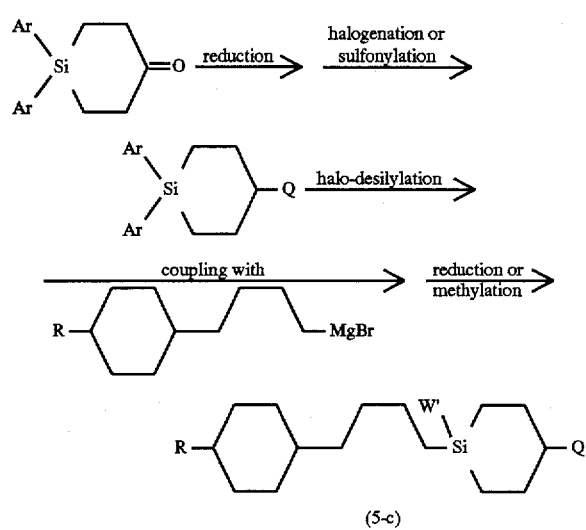

(5-c)

Preparation of

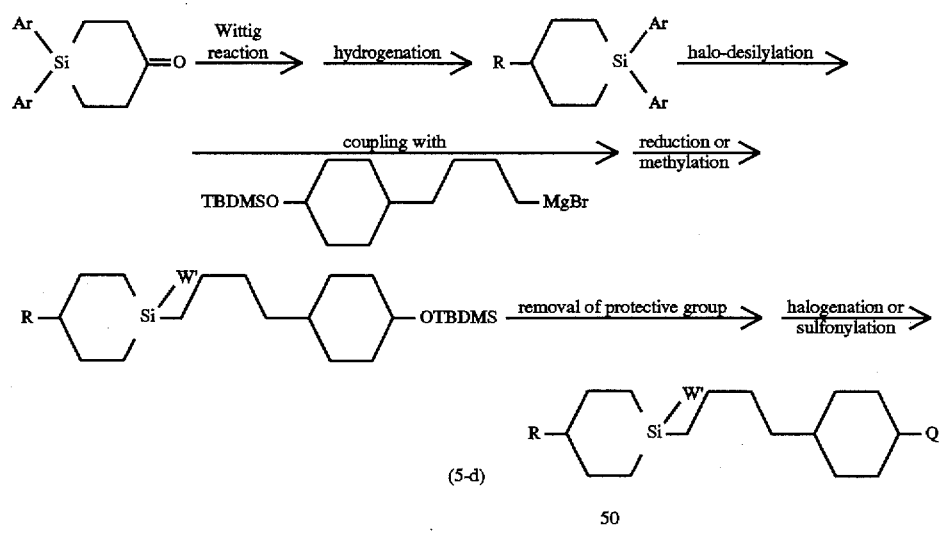

(5-d)

Preparation of

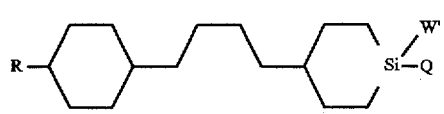

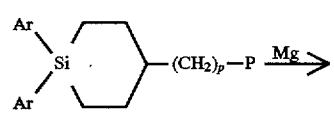

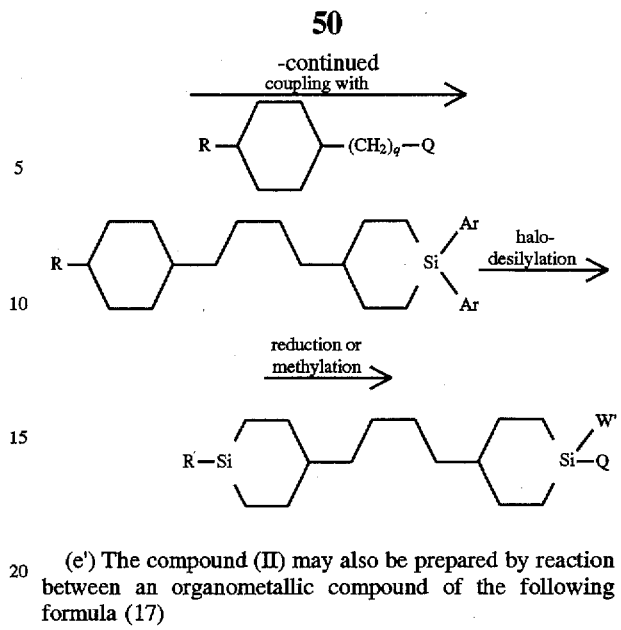

(e') The compound (II) may also be prepared by reaction between an organometallic compound of the following formula (17)

(17)

wherein M' represents MgP or ZnP in which P represents a halogen atom, preferably Cl, Br or I, or $B(OY_1)_2$ in which

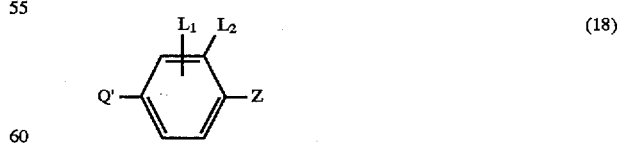

$Y_1$ represents hydrogen or an alkyl group having from 1 to 6 carbon atoms, with a compound of the following formula (18)

(18)

This reaction is conducted in the presence of a transition metal catalyst as in (b) for the preparation of the compound (I). Accordingly, nickel and palladium compounds are preferably used as the catalyst. Preferably, Q' represents Br or I, by which a high yield is expected.

The starting compound (17) may be prepared in the same manner as in (5-a) to (5-c) set out above wherein Q is converted to M' through reaction with a metal such as Mg, Zn or the like.

Those compounds of the formulas (III) and (IV) wherein phenyl or tolyl is attached to the silicon atom at the 1 and/or 3 position of the silacyclohexane ring, i.e. arylsilacyclohexane compounds, can be converted to chlorosilacyclohexanes, fluorosilacyclohexanes, hydrosilacyclohexanes or methyl-substituted silacydohexanes. It will be noted that the compounds of the formulas (III) and (IV) can be prepared in the same manner as having set out hereinbefore with respect to the case where W' is H or $CH_3$. More particularly, chlorosilacylohexanes, fluorosilacyclohexanes, and hydrosilacyclohexanes of the general formulas (I) and (II) can be readily obtained from those compounds of the formulas (III) and (IV) wherein at least one of

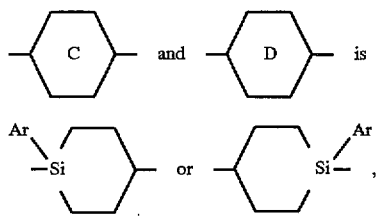

wherein Ar is phenyl or tolyl.

For example, the conversion may be conducted according to the following reaction sequence using a moiety taking part in the conversion reaction hydride under mild conditions, a hydrosilacyclohexane compound of (Ia) to (Ij) and (IIa) to (IIh) where W is hydrogen. Examples of such hydrides include sodium hydride, calcium hydride, trialkylsilanes, boranes, dialkylaluminiums and the like. Examples of the complex hydrides include lithium aluminium hydride, sodium boron hydride, lithium boron hydride, potassium boron hydride, tributylammonium boron hydride and the like. This reaction proceeds in a solvent including an ether such as diethyl ether, tetrahydrofuran or the like, and an aromatic hydrocarbon such as benzene, toluene or the like, at a temperature preferably ranging from $-50°$ to $100°$ C., more preferably from $-20°$ C. to $70°$ C.

Moreover, the silacyclohexane compounds of the general formulas (III) to (IV) wherein two aryl groups are attached to the silicon atom of a silacyclohexane ring can be partially or wholly converted to methyl, chloro, fluoro and hydrosilacyclohexane compounds according to the following reaction sequence (19) in which only a moiety taking part in the conversion reaction is shown.

More particularly, after formation of the fundamental skeletal structure of the silacyclohexane compound, the aryl groups represented by W and R, for example, in the general formulas (Ia) to (Ij) and (IIa) to (IIh), such as phenyl or tolyl, can be converted to H, Cl, F or $CH_3$ according to the following reaction sequence

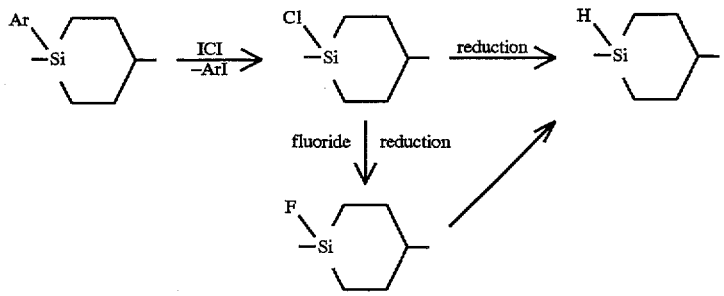

When the arylsilacyclohexane compound of the general formulas (III) and (IV) is reacted with iodine monochloride, a halo-desilylation reaction takes place to provide a chlorosilacyclohexane compound of the formulas (Ia) to (Ij) and (IIa) to (IIh) whore W is Cl. This conversion reaction can be conducted in a halogenated hydrocarbon such as chloromethylene, chloroform, carbon tetrachloride or the like at a temperature of from $0°$ to a refluxing temperature, e.g. $80°$ C., preferably from $10°$ to $40°$ C.

The thus obtained chlorosilacyclohexane compound may be further reacted with fluorides such as cesium fluoride, copper (I) fluoride, antimony fluoride, calcium fluoride, tetra-n-butylammonium fluoride and the like, thereby obtaining a fluorosilacyclohexane compound of the formulas (Ia) to (Ij) and (IIa) to (IIh) wherein W is fluorine. This reaction proceeds in a hydrocarbon solvent such as hexane, heptane, benzene, toluene or the like at a temperature from $0°$ to a refluxing temperature of the reaction system.

If the chlorosilacyclohexane or fluorosilacyclohexane compound is reacted with a metal hydride or a complex (19)

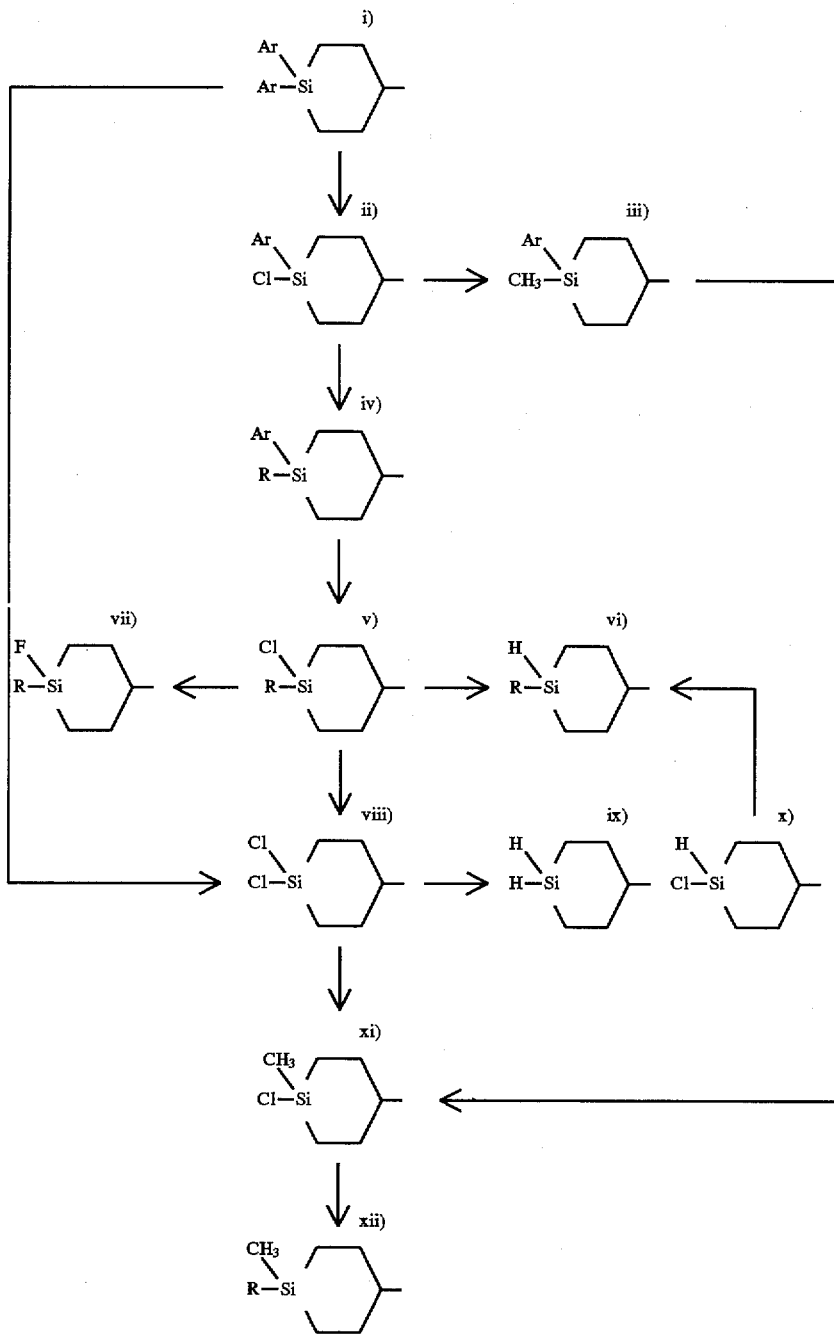

The substitution in the above reaction sequence is described in detail.

First, the diarylsilacyclohexane compound (i) is subjected to de-silylation reaction with an electrophilic compound or reagent to obtain a halosilacyclohexane compound, typical of which is a chlorosilacyclohexane compound (ii). A further de-silylation reaction of the compound (ii) results in a dihalo compound (viii).

The electrophilic reagents used in the above reaction include metal halides, sulfonic acid derivatives, acid halides an dialkyl halides and the like. Preferred reagents include iodine, bromine, chlorine, iodine monochloride, hydrogen chloride, hydrogen bromide, hydrogen iodide, mercury (II) halide, trimethylsilyl chlorosulfonate, acetyl chloride, acetyl bromide, benzoyl chloride, t-butyl chloride and the like. In order to increase the reaction velocity, Lewis acids such as aluminium chloride, zinc chloride, titanium tetrachloride, boron trifluoride are added. Alternatively, the reaction system may be irradiated with actinic light.

If the compound (ii) is further reacted with an organometallic compound such as $CH_3M$ or R-M wherein R is as defined hereinbefore and M is Li, a magnesium halide or a zinc halide, thereby obtaining the compound (iii) or (iv).

In the same manner as in the conversion of the compound (i) to (ii), the compound (iv) can be converted to a compound (v).

Moreover, the reduction of the compound (v) results in compound (iv).

The reagents or compounds used to reduce the halosilacyclohexane compound include metal hydrides such as sodium hydride, calcium hydride, trialkylsilanes, boranes, dialkylaluminiums and the like, complex hydrides such as lithium aluminium hydride, sodium boron hydride, lithium boron hydride, potassium boron hydride, tributylammonium boron hydride and the like, and substituted hydrides of these hydrides, e.g. lithium trialkoxyaluminium hydrides, sodium di(methoxyethoxy)aluminium hydride, lithium triethylborohydride, sodium cyanoborohydride and the like.

The compound (vi) may be obtained from compound (x) in the same manner as in the conversion of (ii) to (iv).

When the compound (v) is reacted with a fluorinating agent such as antimony fluoride, copper fluoride or the like, the chlorine can be substituted with fluorine to obtain compound (vii).

In the same manner as in the conversion of (ii) to (iii) or (iv), the compound (viii) can be converted to compound (xi) or (v). The compound (ix) may be obtained from the compound (iii) in the same manner as in the conversion of the compound (i) to the compound (ii).

In the same manner as in the conversion of the compound (v) to the compound (vi), the compound (ix) is obtained from (viii).

Moreover, if the compound (ix) is reacted with a halogen or halide such as chlorine, bromine, iodine, iodine monochloride or the like or a halogenating agent such as copper chloride+copper iodide, compound (x) is obtained.

The compound (xii) can be obtained from (xi) in the same manner as in the conversion of (ii) to (iv).

However, where R in the above formula (19) is a fluoroalkyl group which is introduced at the silicon atom of the moiety, a substituent, R', which has a silyl ether such as a dimethyl t-butyl ether group is initially introduced, followed by reaction with a reagent such as TBAF (tetrabutylammonium fluoride) for elimination of the protective group, thereby providing an alcohol. Thereafter, the alcohol is fluorinated with a fluorinating agent such as DAST (diethylaminosulfur trifluoride). This is shown below

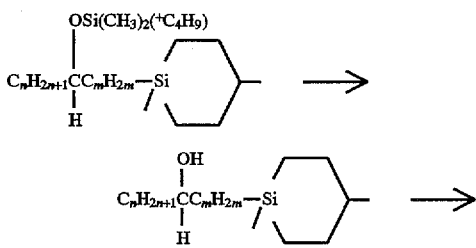

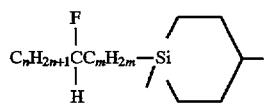

Further, if R represents a difluoroalkyl group having two fluorine atoms joined to a carbon atom, R is introduced at the silicon atom as follows: a carbonyl group-bearing substituent protected with an acetal or a ketal is first introduced, followed by elimination of the protective group and difluorination with a fluorinating agent such as DAST mentioned above. This is shown below

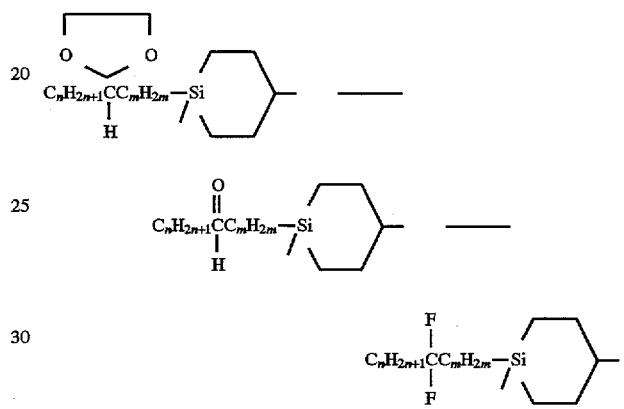

In the general formula (Ia) to (Ij) and (IIa) to (IIh), if Z is CN or a functional group having a —CHF— unit, these groups can be introduced as Z in the following manner.

(1) Introduction of the CN group as Z

A compound having a moiety which has been substituted with a halogen such as Br at a position, at which the cyano group is to be introduced. Thereafter, the compound is converted to a Grignard reagent in a solvent such as tetrahydrofuran. Then, this reagent is reacted with a cyanogen chloride (N≡C—Cl), cyanogen bromide (N≡C—Br), and cyanogen (CN)$_2$, to introduce a cyano group. Alternatively, a cyanogen agent is reacted with the halogenated compound in a solvent such as dimethylformamide to directly introduce the cyano group as Z. These reactions are particularly shown in the following reaction sequence

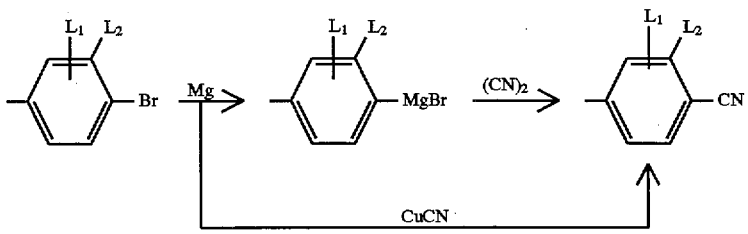

The introduction of the cyano group may be conducted prior to or subsequent to the introduction of substituent or substituents at the silicon atom or atoms.

(2) Introduction of a hydrofluoroalkoxy group as Z

This group is introduced as follows. After formation of a skeletal structure of a silacyclohexane compound wherein a dimethyl-t-butylsilyl group has been substituted, for example, in place of a hydrofluoroalkyl group, the protective group is eliminated and converted to a phenol. Then, the thus converted phenols reacted, for example, with NaH in DMEU (1,3-dimethyl-2-imidazolidinone) to obtain a Na salt of the phenol. This salt is subsequently reacted with a hydrofluoroalkyl bromide to introduce a hydrofluoroalkoxy group. This is shown below

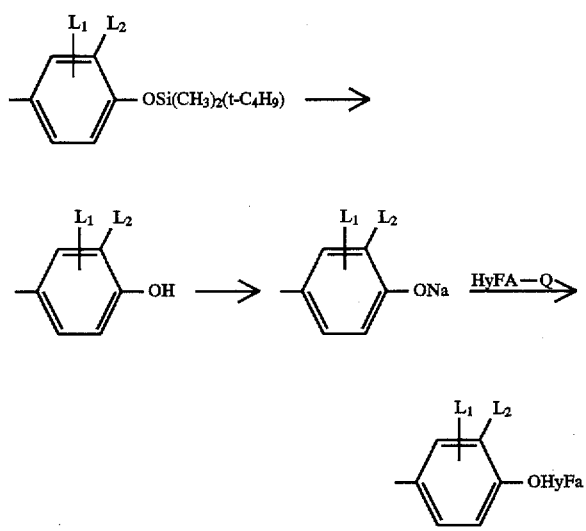

wherein HyFA represents a hydrofluoroalkyl group and Q is as defined before.

The hydrofluoroalkyl group is introduced prior to or subsequent to the introduction of substituent or substituents at the silicon atom or atoms.

(3) Introduction of A hydrofluoroalkenyl group as Z

Further, the introduction of a hydrofluoroalkenyl group as Z is described.

i) A compound having a moiety which has been substituted, for example, with a trimethylsilyl group in place of a hydrofluoroalkenyl group is provided. This compound is brominated with $Br_2$ or iodized with ICl, followed by reaction with metallic magnesium to obtain a Grignard reagent, followed by exchange with zinc to obtain an organozinc compound. Thereafter, the organozinc compound is reacted with a hydrofluoroalkenyl bromide in the presence of a catalyst such as Pd to introduce a hydrofluoroalkenyl group. This is shown below

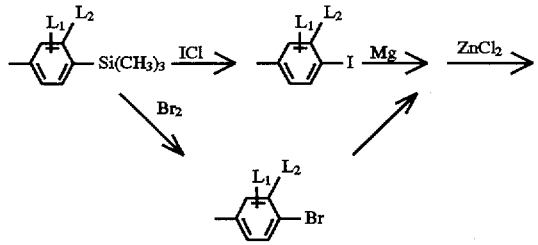

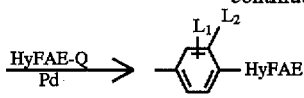

in which HyFAE represents a hydrofluoroalkenyl group, Q is as defined before. The final step is conducted in the presence of a catalyst such as Pd.

ii) Alternatively, after the introduction of a hydrofluoroalkyl group as in (2) above, the group is dehydrofluorinated with a base such as $t-C_4H_9OK$ to form a hydrofluoroalkenyl group as shown below

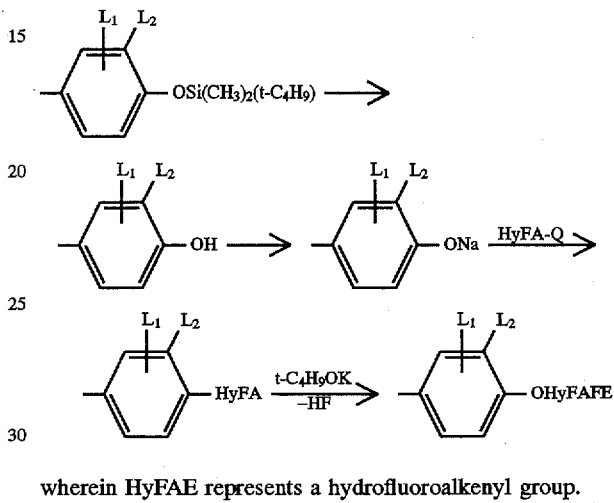

wherein HyFAE represents a hydrofluoroalkenyl group.

The introduction of the hydrofluoroalkenyl group may be effected prior to or subsequent to the introduction of any substituent at the silicon atom.

If the thus obtained silacyclohexane products are in the form of steric trans and cis isomers, a trans isomer can be isolated and purified through known purification procedures such as recrystallization, chromatography and the like.

The silacyclohexane compounds of the formulas (I) and (II) of the invention are conveniently used in combination with known liquid crystal compounds to provide liquid crystal compositions. Such known liquid crystal compounds suitable for this purpose include those compounds of the general formulas (20) and (21)

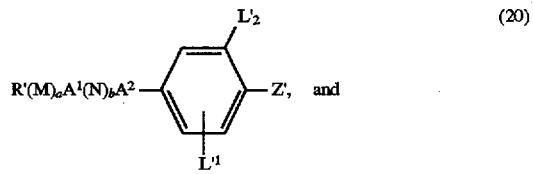

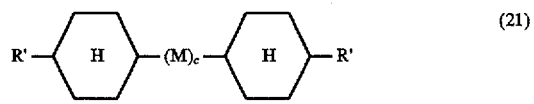

In the above formula (20) and (21), each R' represents a linear alkyl group having from 1 to 10 carbon atoms, a mono or difluoroalkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms; Z' represents CN, F, Cl, $CF_3$, $CF_2Cl$, $CHFCl$, $OCF_3$, $OCF_2Cl$, $OCHFCl$, $OCHF_2$, $(O)_m \cdot CY=CX_1X_2$, in which m is 0 or 1, Y and $X_1$ independently represent H, F or Cl, $X_2$ represents F or Cl, $O(CH_2)_r(CF_2)_sX_3$, in which r and s are, respectively, 0, 1 or 2 provided that (r+s) is 2, 3 or 4, and $X_3$ H, F or Cl, R' or OR' wherein R' is as defined above, $L'_1$ is H or F, $L'_2$ is H, F or Cl; M and N independently represent (1) an unsubstituted or substituted trans-1,4-cyclohexylene group which has, if substituted, one or more substituents such as F, Cl, Br, CN and an alkyl group having from 1 to 3 carbon atoms, (2) a trans-1,4-cyclohexylene group wherein one $CH_2$ unit or two $CH_2$ units, not adjacent each other, of the cyclohexane ring are replaced by O or S, (3) a 1,4-cyclohexenylene group, (4) an unsubstituted or substituted 1,4-phenylene group having, if substituted, one or two F, Cl, $CH_3$ and/or CN groups and (5) a 1,4-phenylene group in which one or two CH units of the phenylene group are replaced by nitrogen atom; a and b are, respectively, 0, 1 or 2 provided that a+b=1, 2 or 3, and c is 0, 1 or 2; and $A^1$ and $A^2$ are, respectively, —$CH_2CH_2$—, —CH=CH—, —C≡C—, —$CO_2$—, —OCO—, —$CH_2O$—, —$OCH_2$— or single bond.

In the above formulas (20) and (21), if a, b and/or c is 2, M's and/or N's may be the same or different and are independently selected from the groups (1) to (5) set forth above.

The silacyclohexane compounds which may be used singly or in combination should preferably be present in a liquid crystal phase or composition in an amount of from 1 to 50 mole %, preferably from 5 to 30 mole %. As a matter of course, the liquid crystal composition may further comprise polychromatic dyes capable of forming colored guest-host systems, and additives capable of imparting dielectric anisotropy, viscosity modifiers, additives for changing the direction of alignment of a nematic phase.

The polychromatic dyes may, respectively, be azo dyes and anthaquinone dyes of the following formulas (22) and (23)

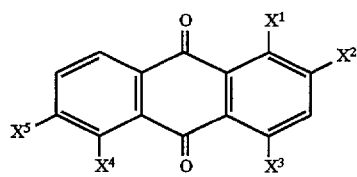

wherein $X^1$ to $X^5$ independently represent H, OH, a halogen, CN, an unsubstituted or substituted amino group, an unsubstituted or substituted carboxylate group, an unsubstituted or substituted phenyloxy group, an unsubstituted or substituted benzyl group, an unsubstituted or substituted phenylthio group, an unsubstituted or substituted phenyl group, an unsubstituted or substituted cyclohexyloxxycarbonyl group, or an unsubstituted or substituted pyridyl or pyrimidyl group.

In practice, the liquid crystal phase or composition comprising at least one compound of the invention is used in liquid crystal display devices. In the devices, the composition is hermetically sealed between transparent substrates each having an electrode of a desired shape. If necessary, the device may have various types of undercoatings, overcoatings for controlling the alignment, a polarizer, a filter and a reflective layer as is known in the art. Alternatively, a multi-layer cell may be used to incorporate the compounds of the invention. The liquid crystal display device may be used in combination with other types of display devices, semiconductor substrates, and light sources.

The liquid crystal devices comprising the compounds of the invention may be driven by any known systems including a dynamic scattering (DSM) system, a twisted nematic (TN) system, a super twisted nematic (STN) system, a polymer dispersion liquid crystal (PDLC) system, a guest-host (GH) system and the like.

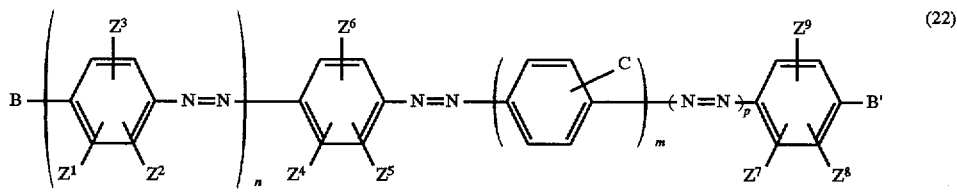

wherein B and B' independently represent an unsubstituted or substituted alkyl group or dialkylamino group in which when B and B' are independently, the substituted group, the group is substituted with a plurality of fluorine aroma or is substituted at —$CH_2$— units not adjacent to each other in the chain of the group with O, S, NH, $SO_2$, $O_2C$,

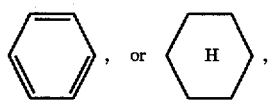

$Z^1$ to $Z^9$ independently represent hydrogen, an alkyl group or alkoxy group having preferably from 1 to 4 carbon atoms such as methyl or methoxy, or a halogen provided that $Z^1$ and $Z^2$, $Z^4$ and $Z^5$, and $Z^7$ and $Z^8$ are, respectively, able to join together thereby forming an alicyclic ring, an aromatic ring or a nitrogen-containing aromatic ring, C represents a fluoroalkyl group, and n is 0, 1 or 2, m is 0, 1 or 2 and p is 0 or 1 provided that when m is 0, p is 0, or The invention is more particularly described by way of examples. The examples were carried out at room temperature.

EXAMPLE 1
Preparation of trans-4-(trans-4-(4-(4-cyanophenyl) butyl)cyclohexyl)-1-propyl-1-silacyclohexane 50 ml (0.18 moles) of a tetrahydrofuran (hereinafter referred to simply as THF) solution of 2.5M of propylmagnesium chloride was dropped in a mixed solution of 37.4 g (0.1 mol) of 1-chloro-4-(trans-4-(4-(4-cyanophenyl)butyl) cyclohexyl)-1-silacyclohexane and 300 ml of THF. The resultant product was found to be a mixture of trans and cis isomers with respect to the silacyclohexane ring. The product was subjected to ordinary aftertreatments such as removal of the solvent and salts, followed by isolation through chromatography to obtain 30.2 g (yield: 79%) of the intended trans isomer product.

EXAMPLE 2
Preparation of trans-4-(trans-4-(4-(4-difluoromethoxyphenyl)butyl)cyclohexyl)-1-butyl-1-silacyclohexane 80 ml (0.13 moles) of a hexane solution of 1.6M of butyl lithium was dropped in a mixed solution of 41.5 g (0.1 mol)

of 1-chloro-4-(4-(trans-4-(4-difluoromethoxyphenyl)butyl) cyclohexyl)-1-silacyclohexane and 30 ml of THF. The resultant product was found to be a mixture of trans and cis isomers with respect to the silacyclohexane ring. The product was subjected to ordinary aftertreatments, followed by isolation through chromatography to obtain 35.9 g (yield: 82.0%) of the intended trans isomer product.

EXAMPLE 3

Preparation of trans-4-(trans-4-(4-(3-fluoro-4-difluoromethoxyphenyl)butyl)cyclohexyl)-1-ethyl-1-silacyclohexane 130 ml (0.13 moles) of a THF solution of 1M of ethylmagnesium bromide was dropped in a mixed solution of 42.9 g (10 mmols) of 1-methoxy-4-(trans-4-(4-(3-fluoro-4-difluoromethoxyphenyl)butyl)cyclohexyl)-1-silacyclohexane and 30 ml of THF. The resultant product was found to be a mixture of trans and cis isomers with respect to the silacyclohexane ring. The product was subjected to ordinary aftertreatments such as removal of solvent and salts, followed by isolation through chromatography to obtain 37.8 g (yield: 88.6%) of the intended trans isomer product.

EXAMPLE 4

Preparation of trans-4-(trans-4-(4-(4-cyanophenyl) butyl)cyclohexyl)-1-(4-pentenyl)-1-silacyclohexane A solution of 200 ml of THF and 14.0 g of zinc chloride was dropped in 130 ml (0.13 mols) of a THF solution of 1M of 4-pentenylmagnesium bromide to obtain an organozinc reagent. The resultant mixture was added to a solution of 300 ml of THF and 37.4 g (0.1 mol) of 1-chloro-4-(trans-4-(4-(4-cyanophenyl)butyl)cyclohexyl)-1-silacyclohexane. The resultant product was found to be a mixture of trans and cis isomers with respect to the silacyclohexane ring. The product was subjected to ordinary aftertreatments such as removal of solvent and salts, followed by isolation through chromatography to obtain 30.9 g (yield: 76%) of the intended trans isomer product.

EXAMPLE 5

Preparation of trans-4-(trans-4-(4-(3,5-difluoro-4-cyanophenyl)butyl)cyclohexyl)-1-pentyl-1-silacyclohexane 50 ml (0.13 mols) of a THF solution of 2.5M of pentenylmagnesium chloride was dropped in a mixed solution of 41.0 g (0.1 mol) of 1-chloro-4-(trans-4-(4-(3,5-difluoro-4-cyanophenyl)butyl)cyclohexyl)-1-silacyclohexane and 300 ml of THF. The resultant product was found to be a mixture of trans and cis isomers with respect to the silacyclohexane ring. The product was subjected to ordinary aftertreatments such as removal of solvent and salts, followed by isolation through chromatography to obtain 40.1 g (yield: 90%) of the intended trans isomer product.

EXAMPLE 6

Preparation of trans-4-(4-(3,5-difluoro-4-difluoromethoxyphenyl)butyl)-1-propyl-1-silacyclohexane 50 ml (0.13 mols) of a THF solution of 2.5M of propylmagnesium bromide was dropped in a mixed solution of 36.9 g (0.1 mol) of 1-chloro-4-(4-(3,5-difluoro-4-difluoromethoxyphenyl)butyl)-1-silacyclohexane and 300 ml of THF. The resultant product was found to be a mixture of trans and cis isomers with respect to the silacyclohexane ring. The product was subjected to ordinary aftertreatments such as removal of solvent and salts, followed by isolation through chromatography to obtain 32.1 g (yield: 85%) of the intended trans isomer product.

EXAMPLE 7

Preparation of trans-4-(trans-4-(4-(4-trifluoromethylphenyl)butyl)cyclohexyl)-1-propyl-1-silacyclohexane 22.1 g (0.1 mol) of 1-bromo-4-propyl-4-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 36.3 g (0.1 mol) of 4-(4-(4-trifluoromethylphenyl)butyl)cyclohexyl bromide. The resultant product was subjected to ordinary aftertreatments to obtain trans-4-(trans-4-(4-(4-trifluoromethylphenyl) butyl)cyclohexyl)-1-propyl-1-silacyclohexane. After ordinary aftertreatments, the product was purified through chromatography to obtain 12.2 g (yield: 29%) of the intended trans isomer product.

EXAMPLE 8

Preparation of trans-4-(trans-4-(4-(3-fluoro-4-cyanophenyl)butyl)cyclohexyl)-1-ethyl-1-silacyclohexane 20.7 g (0.1 mol) of 1-bromo-4-ethyl-4-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 33.8 g (0.1 mol) of 4-(4-(3-fluoro-4-cyanophenyl)butyl)cyclohexyl bromide. The resultant product was subjected to ordinary aftertreatments to obtain trans-4-(trans-4-(4-(3-fluoro-4-cyanophenyl)butyl) cyclohexyl)-1-ethyl-1-silacyclohexane. After ordinary aftertreatments, the product was purified through chromatography to obtain 11.0 g (yield: 29%) of the intended trans isomer product.

EXAMPLE 9

Preparation of trans-4-(trans-4-(4-(3,5-difluoro-4-cyanophenyl)butyl)cyclohexyl)-1-propyl-1-silacyclohexane 22.1 g (0.1 mol) of 1-bromo-4-propyl-4-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 35.6 g (0.1 mol) of 4-(4-(3,5-difluoro-4-cyanophenyl)butyl)cyclohexyl bromide. The resultant product was subjected to ordinary aftertreatments to obtain trans-4-(trans-4-(4-(3,5-difluoro-4-cyanophenyl)butyl) cyclohexyl)-1-propyl-1-silacyclohexane. After ordinary aftertreatments, the product was purified through chromatography to obtain 10.7 g (yield: 26%) of the intended trans isomer product.

EXAMPLE 10

Preparation of trans-4-(trans-4-(4-(4-trifluoromethylphenyl)butyl)cyclohexyl)-1-(3-methylbutyl)-1-silacyclohexane 24.9 g (0.1 mol) of 1-bromo-4-(3-methylbutyl)-4-silacyclohexane was dropped in a mixture of 2.5 g (0.11 mols) of magnesium and 300 ml of THF to obtain a Grignard reagent. The resultant solution was further dropped in a solution, in 500 ml of THF, of 1 g of dilithium tetrachlorocuprate (Li$_2$CuCl$_4$) and 43.9 g (0.1 mol) of 4-(4-(4-trifluoromethylphenyl)butyl)cyclohexyl tosylate. The resultant product was subjected to ordinary aftertreatments to obtain trans-4-(trans-4-(4-(4-trifluoromethylphenyl)butyl)cyclohexyl)-1-(3-methylbutyl)-1-silacyclohexane. After ordinary aftertreatments, the product was purified through chromatography to obtain 10.0 g (yield: 22%) of the intended trans isomer product.

EXAMPLE 11

Preparation of trans-4-(trans-4-(4-(3,5-difluoro-4-trifluoromethoxyphenyl)butyl)cyclohexyl)-1-(4-fluorobutyl)-1-silacyclohexane 25.3 g (0.1 mol) of 1-bromo-4-(4-fluorobutyl)-4-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 41.5 g (0.1 mol) of 4-(4-(3,5-difluoro-4-trifluoromethoxyphenyl)butyl)cyclohexyl bromide. The resultant product was subjected to ordinary aftertreatments to obtain trans-4-(trans-4-(4-(3,5-difluoro-4-trifluoromethoxyphenyl)butyl)cyclohexyl)-1-(4-fluorobutyl)-1-silacyclohexane. After ordinary aftertreatments, the product was purified through chromatography to obtain 14.9 g (yield: 29%) of the intended trans isomer product.

EXAMPLE 12

Preparation of trans-4-(trans-4-(4-(4-fluorophenyl)butyl)-1-pentyl-1-silacyclohexane 24.9 g (0.1 mol) of 1-bromo-4-pentyl-4-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 23.1 g (0.1 mol) of 4-(4-bromobutyl)-1-fluorobenzene. The resultant product was subjected to ordinary aftertreatments to obtain trans-4-(4-(4-fluorophenyl)butyl)-1-pentyl-1-silacyclohexane. After ordinary aftertreatments, the product was purified through chromatography to obtain 9.2 g (yield: 29%) of the intended trans isomer product.

EXAMPLE 13

Preparation of trans-4-(trans-4-(4-(4-fluorophenyl)butyl)cyclohexyl)-1-propyl-1-silacyclohexane 31.3 g (0.1 mol) of 4-(4-(4-bromocyclohexyl)butyl)-1-fluorobenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 22.1 g (0.1 mol) of 1-bromo-4-propyl-4-silacyclohexane. The resultant product was subjected to ordinary aftertreatments to obtain trans-4-(trans-4-(4-(4-fluorophenyl)butyl)cyclohexyl)-1-propyl-1-silacyclohexane. After ordinary aftertreatments, the product was purified through chromatography to obtain 11.2 g (yield: 30%) of the intended trans isomer product.

EXAMPLE 14

Preparation of trans-4-(trans-4-(4-(3-fluoro-4-propylphenyl)butyl)-4-silacyclohexyl)-1-ethylcyclohexane 7.1 g (0.1 mol) of 4-bromo-1-(4-(3-fluoro-4-propylphenyl)butyl)-1-silacyclohexyl was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 20.7 g (0.1 mol) of 1-bromo-4-ethylcyclohexane. The resultant product was subjected to ordinary aftertreatments to obtain trans-4-(trans-4-(4-(3-fluoro-4-propylphenyl)butyl)-4-silacyclohexyl)-1-ethylcyclohexane. After ordinary aftertreatments, the product was purified through chromatography to obtain 11.7 g (yield: 29%) of the intended trans isomer product.

EXAMPLE 15

Preparation of trans-4-(trans-4-(4-(4-chlorophenyl)butyl)cyclohexyl)-1-propyl-1-silacyclohexane 33.0 g (0.1 mol) of 4-(4-(4-bromocyclohexyl)butyl)-1-chlorobenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 22.1 g (0.1 mol) of 1-bromo-4-propyl-4-silacyclohexane. The resultant product was subjected to ordinary aftertreatments to obtain trans-4-(trans-4-(4-(4-chlorophenyl)butyl)cyclohexyl)-1-propyl-1-silacyclohexane. After ordinary aftertreatments, the product was purified through chromatography to obtain 12.1 g (yield: 29%) of the intended trans isomer product.

EXAMPLE 16

Preparation of trans-4-(trans-4-(4-(3-fluoro-4-ethylphenyl)butyl)cyclohexyl)-1-butyl-1-silacyclohexane 34.1 g (0.1 mol) of 4-(4-(4-bromocyclohexyl)butyl)-2-fluoro-1-ethylbenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 23.5 g (0.1 mol) of 1-bromo-4-butyl-4-silacyclohexane. The resultant product was subjected to ordinary aftertreatments to obtain trans-4-(trans-4-(4-(3-fluoro-4-ethylphenyl)butyl)cyclohexyl)-1-butyl-1-silacyclohexane. After ordinary aftertreatments, the product was purified through chromatography to obtain 12.1 g (yield: 29%) of the intended trans isomer product.

EXAMPLE 17

Preparation of trans-4-(trans-4-(4-(3,4,5-trifluorophenyl)butyl)cyclohexyl)-1-ethyl-1-silacyclohexane 34.9 g (0.1 mol) of 1-(4-(4-bromocyclohexyl)butyl)-3,4,5-trifluorobenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 20.7 g (0.1 mol) of 1-bromo-4-ethyl-4-silacyclohexane. The resultant product was subjected to ordinary aftertreatments to obtain trans-4-(trans-4-(4-(3,4,5-trifluorophenyl)butyl)cyclohexyl)-1-ethyl-1-silacyclohexane. After ordinary aftertreatments, the product was purified through chromatography to obtain 8.2 g (yield: 21%) of the intended trans isomer product.

EXAMPLE 18

Preparation of trans-4-(4-(4-methoxyphenyl)butyl)-1-heptyl-1-silacyclohexane 24.3 g (0.1 mol) of 4-(4-(4-bromocyclohexyl)butyl) anisole was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 27.7 g (0.1 mol) of 1-bromo-4-heptyl-4-silacyclohexane. The resultant product was subjected to ordinary aftertreatments to obtain trans-4-(4-(4-methoxyphenyl)butyl)-1-heptyl-1-silacyclohexane. After ordinary aftertreatments, the product was purified through chromatography to obtain 10.6 g (yield: 29%) of the intended trans isomer product.

EXAMPLE 19

Preparation of trans-4-(trans-4-(4-(4-chlorodifluoromethylphenyl)butyl)cyclohexyl)-1-pentyl-1-silacyclohexane 33.1 g (0.1 mol) of trans-4-(4-bromocyclohexyl)-1-pentyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 29.8 g (0.1 mol) of 4-(4-bromobutyl)-1-chlorodifluoromethylbenzene. The resultant product was subjected to ordinary aftertreatments to obtain trans-4-(trans-4-(4-(4-chlorodifluoromethylphenyl)butyl)cyclohexyl)-1-pentyl-1-silacyclohexane. After ordinary aftertreatments, the product was purified through chromatography to obtain 14.8 g (yield: 32%) of the trans isomer product.

EXAMPLE 20

Preparation of trans-4-(trans-4-(4-(3-fluoro-4-trifloromethylphenyl)butyl)cyclohexyl)-1-pentyl-1-silacyclohexane 33.1 g (0.1 mol) of trans-4-(4-bromocyclohexyl)-1-pentyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of dilithium tetrachlorocuprate and 37.5 g (0.1 mol) of 4-(3-fluoro-4-trifluoromethylphenyl)butyl tosylate. The resultant product was subjected to ordinary aftertreatments to obtain trans-4-(trans-4-(4-(3-fluoro-4-trifluoromethylphenyl)butyl) cyclohexyl)-1-pentyl-1-silacyclohexane. After ordinary aftertreatments, the product was purified through chromatography to obtain 18.8 g (yield: 40%) of the trans isomer product.

EXAMPLE 21

Preparation of trans-4-(trans-4-(4-(3,5-difluoro-4-trifluoromethoxyphenyl)butyl)cyclohexyl)-1-pentyl-1-silacyclohexane 33.1 g (0.1 mol) of trans-4-(4-bromocyclohexyl)-1-pentyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 38 g (0.1 mol) of 4-(4-iodobutyl)-2,6-difluoro-1-trifluoromethoxybenzene. The resultant product was subjected to ordinary aftertreatments to obtain trans-4-(trans-4-(4-(3,5-difluoro-4-trifluoromethoxyphenyl)butyl)cyclohexyl)-1-pentyl-1-silacyclohexane. After ordinary aftertreatments, the product was purified through chromatography to obtain 19.8 g (yield: 39%) of the trans isomer product.

EXAMPLE 22

Preparation of trans-4-(trans-4-(4-(4-trifluoromethoxyphenyl)butyl)cyclohexyl)-1-propyl-1-silacyclohexane 30.3 g (0.1 mol) of trans-4-(4-bromocyclohexyl)-1-propyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 29.7 g (0.1 mol) of 4-(4-bromobutyl)-1-trifluoromethoxybenzene. The resultant product was subjected to ordinary aftertreatments to obtain trans-4-(trans-4-(4-(4-trifluoromethoxyphenyl)butyl) cyclohexyl)-1-propyl-1-silacyclohexane. After ordinary aftertreatments, the product was purified through chromatography to obtain 16.7 g (yield: 38%) of the trans isomer product.

EXAMPLE 23

Preparation of trans-4-(trans-4-(4-(3,5-difluoro-4-trifluoromethylphenyl)butyl)-1-silacyclohexyl)-1-propylcyclohexane 30.3 g (0.1 mol) of trans-4-(4-bromo-1-silacyclohexyl)-1-propylcyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 31.7 g (0.1 mol) of 4-(4-bromobutyl)-2,6-difluoro-1-trifluoromethylbenzene. The resultant product was subjected to ordinary aftertreatments to obtain trans-4-(trans-4-(4-(3,5-difluoro-4-trifluoromethylphenyl)butyl)-1-silacyclohexyl)-1-propylcyclohexane. After ordinary aftertreatments, the product was purified through chromatography to obtain 15.9 g (yield: 35%) of the trans isomer product.

EXAMPLE 24

Preparation of trans-4-(trans-4-(3-fluoro-4-difluoromethoxyphenyl)butyl)-1-butyl-1-silacyclohexane 23.5 g (0.1 mol) of 1-bromo-4-butyl-4-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 29.7 g (0.1 mol) of 4-(4-bromobutyl)-2-fluoro-1-difluoromethoxybenzene. The resultant product was subjected to ordinary aftertreatments to obtain trans-4-(trans-4-(3-fluoro-4-difluoromethoxyphenyl)butyl)-1-butyl-1-silacyclohexane. After ordinary aftertreatments, the product was purified through chromatography to obtain 14.8 g (yield: 40%) of the trans isomer product.

EXAMPLE 25

Preparation of trans-4-(trans-4-(4-(4-chlorophenyl) butyl)cyclohexyl)-1-pentyl-1-silacyclohexane 24.8 g (0.1 mol) of 4-(4-bromobutyl)-1-chlorobenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 33.1 g (0.1 mol) of trans-4-(4-bromocyclohexyl)

-1-pentyl-1-silacyclohexane. The resultant product was subjected to ordinary aftertreatments to obtain trans-4-(trans-4-(4-(4-chlorophenyl)butyl)cyclohexyl)-1-pentyl-1-silacyclohexane. After ordinary aftertreatments, the product was purified through chromatography to obtain 15.3 g (yield: 37%) of the trans isomer product.

EXAMPLE 26

Preparation of trans-4-(trans-4-(4-(3-fluoro-4-methoxyphenyl)butyl)cyclohexyl)-1-butyl-1-silacyclohexane 26.1 g (0.1 mol) of 4-(4-bromobutyl)-2-fluoroanisole was dropped in a mixture of 2.5 g (0.11 mols) of magnesium and 300 ml of THF to obtain a Grignard reagent. The resultant solution was further dropped in a solution, in 500 ml of THF, of 0.5 g of dilithium tetrachlorocuprate and 39.3 g (0.1 mol) of 4-(trans-4-butyl-4-silacylohexyl)cyclohexyl tosylate. The resultant product was subjected to ordinary aftertreatments to obtain trans-4-(trans-4-(4-(3-fluoro-4-methoxyphenyl) butyl)cyclohexyl)-1-butyl-1-silacyclohexane. After ordinary aftertreatments, the product was purified through chromatography to obtain 15.0 g (yield: 36%) of the trans isomer product.

EXAMPLE 27

Preparation of trans-4-(trans-4-(4-(4-fluorophenyl) butyl)cyclohexyl)-1-pentyl-1-silacyclohexane 23.1 g (0.1 mol) of 4-(4-bromobutyl)-1-fluorobenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 33.1 g (0.1 mol) of trans-4-(4-bromocylohexyl)-1-pentyl-1-silacyclohexane. The resultant product was subjected to ordinary aftertreatments to obtain trans-4-(trans-4-(4-(4-fluorophenyl)butyl)cyclohexyl)-1-pentyl-1-silacyclohexane. After ordinary aftertreatments, the product was purified through chromatography to obtain 14.2 g (yield: 35%) of the trans isomer product.

EXAMPLE 28

Preparation of trans-4-(trans-4-(4-(3-fluoro-4-ethoxyphenyl)butyl)cyclohexyl)-1-pentyl-1-silacyclohexane 27.5 g (0.1 mol) of 4-(4-bromobutyl)-2-fluorophenetole was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 33.1 g (0.1 mol) of trans-4-(4-bromocylohexyl)-1-pentyl-1-silacyclohexane. The resultant product was subjected to ordinary aftertreatments to obtain trans-4-(trans-4-(4-(3-fluoro-4-ethoxyphenyl)butyl)cyclohexyl)-1-pentyl-1-silacyclohexane. After ordinary aftertreatments, the product was purified through chromatography to obtain 14.6 g (yield: 33%) of the trans isomer product.

EXAMPLE 29

Preparation of trans-4-(trans-4-(4-(3,4,5-trifluorophenyl)butyl)cyclohexyl)-1-pentyl-4-silacyclohexane 26.7 g (0.1 mol) of 5-(4-bromobutyl)-1,2,3-trifluorobenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 33.1 g (0.1 mol) of trans-4-(4-bromocylohexyl)-1-pentyl-1-silacyclohexane. The resultant product was subjected to ordinary aftertreatments to obtain trans-4-(trans-4-(4-(3,4,5-trifluorophenyl)butyl) cyclohexyl)- 1-pentyl-4-silacyclohexane. After ordinary aftertreatments, the product was purified through chromatography to obtain 14.7 g (yield: 34%) of the trans isomer product.

EXAMPLE 30

Preparation of trans-4-(4-(3,4-difluorophenyl)butyl)-1-pentyl-4-silacyclohexane 24.9 g (0.1 mol) of 4-(4-bromobutyl)-1,2-difluorobenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 24.9 g (0.1 mol) of 4-bromo-1-pentyl-1-silacyclohexane. The resultant product was subjected to ordinary aftertreatments to obtain trans-4-(4-(3,4-difluorophenyl)butyl)-1-pentyl-4-silacyclohexane. After ordinary aftertreatments, the product was purified through chromatography to obtain 13.5 g (yield: 40%) of the trans isomer product.

EXAMPLE 31

Preparation of trans-4-(trans-4-(4-(4-chlorofluoromethylphenyl)butyl)cyclohexyl)-1-pentyl-1-silacyclohexane 34.5 g (0.1 mol) of trans-4-(trans-4-bromomethylcyclohexyl)-1-pentyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 26.6 g (0.1 mol) of 4-(3-bromopropyl)-1-chlorofluoromethylbenzene. The resultant product was subjected to ordinary aftertreatments to obtain trans-4-(trans-4-(4-(4-chlorofluoromethylphenyl)butyl)cyclohexyl)-1-pentyl-1-silacyclohexane. After ordinary aftertreatments, the product was purified through chromatography to obtain 35.6 g (yield: 79%) of the trans isomer product.

EXAMPLE 32

Preparation of trans-4-(trans-4-(4-(3-fluoro-4-chlorodifluoromethylphenyl)butyl)cyclohexyl)-1-pentyl-1-silacyclohexane 34.5 g (0.1 mol) of trans-4-(trans-4-bromomethylcyclohexyl)-1-pentyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 30.1 g (0.1 mol) of 4-(3-bromopropyl)-2-fluoro-1-chlorodifluoromethylbenzene. The resultant product was subjected to ordinary aftertreatments to obtain trans-4-(trans-4-(4-(3-fluoro-4-chlorodifluoromethylphenyl)butyl) cyclohexyl)-1-pentyl-1-silacyclohexane. After ordinary aftertreatments, the product was purified through chromatography to obtain 38.0 g (yield: 78%) of the trans isomer product.

EXAMPLE 33

Preparation of trans-4-(trans-4-(4-(3,5-difluoro-4-trifluoromethylphenyl)butyl)cyclohexyl)-1-pentyl-1-silacyclohexane 34.5 g (0.1 mol) of trans-4-(trans-4-bromomethylcyclohexyl)-1-pentyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 30.3 g (0.1 mol) of 4-(3-bromopropyl)-2,6-difluoro-1-trifluoromethylbenzene. The resultant product was subjected to ordinary aftertreatments to obtain trans-4-(trans-4-(4-(3,5-difluoro-4-trifluoromethylphenyl)butyl)cyclohexyl)-1-pentyl-1-silacyclohexane. After ordinary aftertreatments, the product was purified through chromatography to obtain 40.9 g (yield: 84%) of the trans isomer product.

EXAMPLE 34

Preparation of trans-4-(trans-4-(4-(4-difluoromethoxyphenyl)butyl)cyclohexyl)-1-pentyl-1-silacyclohexane 34.5 g (0.1 mol) of trans-4-(trans-4-bromomethylcyclohexyl)-1-pentyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 26.5 g (0.1 mol) of 4-(3-bromopropyl)-1-difluoromethoxybenzene. The resultant product was subjected to ordinary aftertreatments to obtain trans-4-(trans-4-(4-(4-difluoromethoxyphenyl)butyl)cyclohexyl)-1-pentyl-1-silacyclohexane. After ordinary aftertreatments, the product was purified through chromatography to obtain 38.0 g (yield: 84%) of the trans isomer product.

EXAMPLE 35

Preparation of trans-4-(trans-4-(4-(3,5-difluoro-4-difluoromethylphenyl)butyl)cyclohexyl)-1-pentyl-1-silacyclohexane 34.5 g (0.1 mol) of trans-4-(trans-4-bromomethylcyclohexyl)-1-pentyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 30.1 g (0.1 mol) of 4-(3-bromopropyl)-2,6-difluoro-1-difluoromethoxybenzene. The resultant product was subjected to ordinary aftertreatments to obtain trans-4-(trans-4-(4-(3,5-difluoro-4-difluoromethylphenyl)butyl)cyclohexyl)-1-pentyl-1-silacyclohexane. After ordinary aftertreatments, the product was purified through chromatography to obtain 40.8 g (yield: 84%) of the trans isomer product.

EXAMPLE 36

Preparation of trans-4-hexyl-1-(4-(4-cyanophenyl)butyl)-1-silacyclohexane 23.3 g (0.1 mol) of trans-4-hexyl-1-chloromethyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 22.4 g (0.1 mol) of 4-(3-bromopropyl)benzonitrile. The resultant product was subjected to ordinary aftertreatments to obtain trans-4-hexyl-1-(4-(4-cyanophenyl)butyl)-1-silacyclohexane. After ordinary aftertreatments, the product was purified through chromatography to obtain 29.0 g (yield: 85%) of the trans isomer product.

EXAMPLE 37

Preparation of trans-4-(trans-4-(4-(4-ethylphenyl)butyl)cyclohexyl)-1-propyl-1-silacyclohexane 22.7 g (0.1 mol) of 4-(3-bromopropyl)-1-ethylbenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 31.7 g (0.1 mol) of trans-4-(trans-4-bromomethylcyclohexyl)-1-propyl-1-silacyclohexane. The resultant product was subjected to ordinary aftertreatments to obtain trans-4-(trans-4-(4-(4-ethylphenyl)butyl)cyclohexyl)-1-propyl-1-silacyclohexane. After ordinary aftertreatments, the product was purified through chromatography to obtain 31.7 g (yield: 82%) of the trans isomer product.

EXAMPLE 38

Preparation of trans-4-(trans-4-(4-(4-chloro-3,5-difluorophenyl)butyl)cyclohexyl)-1-propyl-1-silacyclohexane 27.0 g (0.1 mol) of 4-(3-bromopropyl)-2,6-difluoro-1-chlorobenzene was dropped in a mixture of 2.5 g (0.11 mols) of magnesium and 300 ml of THF to obtain a Grignard reagent. The resultant solution was further dropped in a solution, in 500 ml of THF, of 0.5 g of dilithium tetrachlorocuprate and 39.3 g (0.1 mol) of trans-4-(trans-4-propyl-4-silacyclohexyl)cyclohexyl tosylate. The resultant product was subjected to ordinary aftertreatments to obtain trans-4-(trans-4-(4-(4-chloro-3,5-difluorophenyl)butyl)cyclohexyl)-1-propyl-1-silacyclohexane. After ordinary aftertreatments, the product was purified through chromatography to obtain 35.9 g (yield: 84%) of the trans isomer product.

EXAMPLE 39

Preparation of trans-4-(trans-4-(4-(4-ethylphenyl)butyl)cyclohexyl)-1-pentyl-1-silacyclohexane 22.7 g (0.1 mol) of 4-(3-bromopropyl)-1-ethylbenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 34.5 g (0.1 mol) of trans-4-(trans-4-bromomethylcyclohexyl)-1-pentyl-1-silacyclohexane. The resultant product was subjected to ordinary aftertreatments to obtain trans-4-(trans-4-(4-(4-ethylphenyl)butyl)cyclohexyl)-1-pentyl-1-silacyclohexane. After ordinary aftertreatments, the product was purified through chromatography to obtain 32.6 g (yield: 79%) of the trans isomer product.

EXAMPLE 40

Preparation of trans-4-(trans-4-(4-(4-chloro-3,5-difluorphenyl)butyl)cyclohexyl)-1-silacyclohexane 27.0 g (0.1 mol) of 4-(3-bromopropyl)-2,6-difluoro-1-chlorobenzene was dropped in a mixture of 2.5 g (0.11 mols)

of magnesium and 300 ml of THF to obtain a Grignard reagent. The resultant solution was further dropped in a solution, in 500 ml of THF, of 0.5 g of triethyl phosphate, 0.1 g of copper (I) iodide and 33.1 g (0.1 mol) of trans-4-(trans-4-bromomethylcyclohexyl)-1-butyl-1-silacyclohexane. The resultant product was subjected to ordinary aftertreatments to obtain trans-4-(trans-4-(4-(4-chloro-3,5-difluorophenyl) butyl)cyclohexyl)-1-butyl-1-silacyclohexane. After ordinary aftertreatments, the product was purified through chromatography to obtain 37.4 g (yield: 85%) of the trans isomer product.

EXAMPLE 41

Preparation of trans-4-(trans-4-(4-(4-ethoxy-2,3-difluorophenyl)butyl)cyclohexyl)-1-butyl-1-silacyclohexane 27.9 g (0.1 mol) of 4-(3-bromopropyl)-2,3-difluorophenetole was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 33.1 g (0.1 mol) of trans-4-(trans-4-bromomethylcyclohexyl)-1-butyl-1-silacyclohexane. The resultant product was subjected to ordinary aftertreatments to obtain trans-4-(trans-4-(4-(4-ethoxy-2,3-difluorophenyl) butyl)cyclohexyl)-1-butyl-1-silacyclohexane. After ordinary aftertreatments, the product was purified through chromatography to obtain 35.5 g (yield: 79%) of the trans isomer product.

EXAMPLE 42

Preparation of trans-4-(4-(4-fluorophenyl)butyl)-1-heptyl-1-silacyclohexane 21.7 g (0.1 mol) of 4-(3-bromopropyl)-1-fluorobenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 29.1 g (0.1 mol) of trans-4-bromomethyl-1-heptyl-1-silacyclohexane. The resultant product was subjected to ordinary aftertreatments to obtain trans-4-(4-(4-fluorophenyl)butyl)-1-heptyl-1-silacyclohexane. After ordinary aftertreatments, the product was purified through chromatography to obtain 29.6 g (yield: 85%) of the trans isomer product.

EXAMPLE 43

Preparation of trans-4-(trans-4-(4-(4-trifluoromethoxyphenyl)butyl)cyclohexyl)-1-pentyl-1-silacyclohexane 36.0 g (0.1 mol) of trans-4-(trans-4-(2-bromoethyl) cyclohexyl)-1-pentyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 26.9 g (0.1 mol) of trans-4-(2-bromoethyl)-1-trifluoromethoxybenzene. The resultant product was subjected to ordinary aftertreatments to obtain trans-4-(trans-4-(4-(4-trifluoromethoxyphenyl)butyl)cyclohexyl)-1-pentyl-1-silacyclohexane. After ordinary aftertreatments, the product was purified through chromatography to obtain 36.5 g (yield: 78%) of the trans isomer product.

EXAMPLE 44

Preparation of trans-4-(trans-4-(4-(3-fluoro-4-chlorofluoromethylphenyl)butyl)cyclohexyl)-1-pentyl-1-silacyclohexane 36.0 g (0.1 mol) of trans-4-(trans-4-(2-bromoethyl) silacyclohexyl)-1-pentyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 27.0 g (0.1 mol) of 4-(2-bromoethyl)-2-fluoro-1-chlorofluoromethylbenzene. The resultant product was subjected to ordinary aftertreatments to obtain trans-4-(trans-4-(4-(3-fluoro-4-chlorofluoromethylphenyl)butyl)cyclohexyl)-1-pentyl-1-silacyclohexane. After ordinary aftertreatments, the product was purified through chromatography to obtain 38.8 g (yield: 83%) of the trans isomer product.

EXAMPLE 45

Preparation of trans-4-(trans-4-(4-(3,5-difluoro-4-chlorodifluoromethylphenyl)butyl)cyclohexyl)-1-pentyl-1-silacyclohexane 36.0 g (0.1 mol) of trans-4-(trans-4-(2-bromoethyl) cyclohexyl)-1-pentyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 30.6 g (0.1 mol) of 4-(2-bromoethyl)-2,6-difluoro-1-chlorodifluoromethylbenzene. The resultant product was subjected to ordinary aftertreatments to obtain trans-4-(trans-4-(4-(3,5-difluoro-4-chlorodifluoromethylphenyl) butyl)cyclohexyl)-1-pentyl-1-silacyclohexane. After ordinary aftertreatments, the product was purified through chromatography to obtain 40.3 g (yield: 80%) of the trans isomer product.

EXAMPLE 46

Preparation of trans-4-(trans-4-(4-(3-fluoro-4-cyanophenyl)butyl)cyclohexyl)-1-propyl-1-silacyclohexane 33.1 g (0.1 mol) of trans-4-(trans-4-(2-bromoethyl) cyclohexyl)-1-propyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 22.8 g (0.1 mol) of 4-(2-bromoethyl)-2-fluorobenzonitrile. The resultant product was subjected to ordinary aftertreatments to obtain trans-4-(trans-4-(4-(3-fluoro-4-cyanophenyl)butyl) cyclohexyl)-1-propyl-1-silacyclohexane. After ordinary aftertreatments, the product was purified through chromatography to obtain 32.6 g (yield: 82%) of the trans isomer product.

EXAMPLE 47

Preparation of trans-4-(trans-4-(4-(3,5-difluoro-4-difluoromethoxyphenyl)butyl)cyclohexyl)-1-ethyl-1-silacyclohexane 31.7 g (0.1 mol) of trans-4-(trans-4-(2-bromoethyl) cyclohexyl)-1-ethyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 28.7 g (0.1 mol) of 4-(2-bromoethyl)-2,6-difluoro-1-difluoromethoxybenzene. The resultant product was subjected to ordinary aftertreatments to obtain trans-4-(trans-4-(4-(3,5-difluoro-4-difluoromethoxyphenyl)butyl)cyclohexyl)-1-ethyl-1-silacyclohexane. After ordinary aftertreatments, the product was purified through chromatography to obtain 34.9 g (yield: 79%) of the trans isomer product.

EXAMPLE 48

Preparation of trans-4-(4-(3-fluoro-4-trifluoromethoxyphenyl)butyl)-1-pentyl-1-silacyclohexane 27.7 g (0.1 mol) of trans-4-(2-bromoethyl)-1-pentyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 28.7 g (0.1 mol) of 4-(2-bromoethyl)-2-fluoro-1-trifluoromethoxybenzene. The resultant product was subjected to ordinary aftertreatments to obtain trans-4-(4-(3-fluoro-4-trifluoromethoxyphenyl)butyl)-1-pentyl-1-silacyclohexane. After ordinary aftertreatments, the product was purified through chromatography to obtain 34.3 g (yield: 85%) of the trans isomer product.

EXAMPLE 49

Preparation of trans-4-(trans-4-(4-(4-ethoxyphenyl)butyl)cyclohexyl)-1-pentyl-1-silacyclohexane 22.9 g (0.1 mol) of 4-(2-bromoethyl)phenetole was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 36.0 g (0.1 mol) of trans-4-(trans-4-(2-bromoethyl)cyclohexyl)-1-pentyl-1-silacyclohexane. The resultant product was subjected to ordinary aftertreatments to obtain trans-4-(trans-4-(4-(4-ethoxyphenyl)butyl)cyclohexyl)-1-pentyl-1-silacyclohexane. After ordinary aftertreatments, the product was purified through chromatography to obtain 33.8 g (yield: 79%) of the trans isomer product.

EXAMPLE 50

Preparation of trans-4-(trans-4-(4-(3,4,5-trifluorophenyl)butyl)cyclohexyl)-1-(3-methoxypropyl)-1-silacyclohexane 23.9 g (0.1 mol) of 5-(2-bromoethyl)-1,2,3-trifluorobenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 36.1 g (0.1 mol) of trans-4-(trans-4-(2-bromoethyl)cyclohexyl)-1-(3-methoxypropyl)-1-silacyclohexane. The resultant product was subjected to ordinary aftertreatments to obtain trans-4-(trans-4-(4-(3,4,5-trifluorophenyl)butyl)cyclohexyl)-1-(3-methoxypropyl)-1-silacyclohexane. After ordinary aftertreatments, the product was purified through chromatography to obtain 36.7 g (yield: 83%) of the trans isomer product.

EXAMPLE 51

Preparation of trans-4-(trans-4-(4-(4-ethoxyphenyl)butyl)cyclohexyl)-1-propyl-1-silacyclohexane 22.9 g (0.1 mol) of 4-(2-bromoethyl)-1-phenetole was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 33.1 g (0.1 mol) of trans-4-(trans-4-(2-bromoethyl)cyclohexyl)-1-propyl-1-silacyclohexane. The resultant product was subjected to ordinary aftertreatments to obtain trans-4-(trans-4-(4-(4-ethoxyphenyl)butyl)cyclohexyl)-1-propyl-1-silacyclohexane. After ordinary aftertreatments, the product was purified through chromatography to obtain 31.1 g (yield: 78%) of the trans isomer product.

EXAMPLE 52

Preparation of trans-4-(trans-4-(4-(2,3-difluoro-4-ethoxyphenyl)butyl)cyclohexyl)-1-propyl-1-silacyclohexane 26.5 g (0.1 mol) of 4-(2-bromoethyl)-2,3-difluorophenetole was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 33.1 g (0.1 mol) of trans-4-(trans-4-(2-bromoethyl)cyclohexyl)-1-propyl-1-silacyclohexane. The resultant product was subjected to ordinary aftertreatments to obtain trans-4-(trans-4-(4-(2,3-difluoro-4-ethoxyphenyl)butyl)cyclohexyl)-1-propyl-1-silacyclohexane. After ordinary aftertreatments, the product was purified through chromatography to obtain 37.0 g (yield: 85%) of the trans isomer product.

EXAMPLE 53

Preparation of trans-4-(trans-4-(4-(3,4-difluorophenyl)butyl)cyclohexyl)-1-(4-fluorobutyl)-1-silacyclohexane 22.1 g (0.1 mol) of 4-(2-bromoethyl)-1,2-difluorophenetole was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I)iodide and 36.3 g (0.1 mol) of trans-4-(trans-4-(2-bromoethyl)cyclohexyl)-1-(4-fluorobutyl)-1-silacyclohexane. The resultant product was subjected to ordinary aftertreatments to obtain trans-4-(trans-4-(4-(3,4-difluorophenyl)butyl)cyclohexyl)- 1-(4-fluorobutyl)-1-silacyclohexane. After ordinary aftertreatments, the product was purified through chromatography to obtain 36.0 g (yield: 85%) of the trans isomer product.

EXAMPLE 54

Preparation of trans-4-(4-(3,4,5-trifluorophenyl)butyl)-1-pentyl-1-silacyclohexane 23.9 g (0.1 mol) of 5-(2-bromoethyl)-1,2,3-trifluorobenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 27.7 g (0.1 mol) of trans-4-(2-bromoethyl)-1-pentyl-1-silacyclohexane. The resultant product was subjected to ordinary aftertreatments to obtain trans-4-(4-(3,4,5-trifluorophenyl)butyl)-1-pentyl-1-silacyclohexane. After ordinary aftertreatments, the product was purified through chromatography to obtain 28.3 g (yield: 79%) of the trans isomer product.

EXAMPLE 55

Preparation of trans-4-(trans-4-(4-(4-chlorodifluoromethoxyphenyl)butyl)cyclohexyl)-1-propyl-1-silacyclohexane 34.5 g (0.1 mol) of trans-4-(trans-4-(3-bromopropyl)cyclohexyl)-1-propyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper(I)iodide and 27.2 g (0.1 mol) of 4-bromomethyl-1-difluorochloromethoxybenzene. After ordinary aftertreatments, the resultant product was pitied through chromatography to obtain 41.0 g (yield: 90%) of trans-4-(trans-4-(4-(4-chlorodifluoromethoxyphenyl)butyl)cyclohexyl)-1-propyl-1-silacyclohexane.

EXAMPLE 56

Preparation of trans-4-(trans-4-(4-(3-fluoro-4-trifluoromethoxyphenyl)butyl)cyclohexyl)-1-propyl-1-silacyclohexane 34.5 g (0.1 mol) of trans-4-(trans-4-(3-bromopropyl)cyclohexyl)-1-propyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I)iodide and 27.3 g (0.1 mol) of 4-bromomethyl-2-fluoro-1-trichloromethoxybenzene. The resultant product was subjected to ordinary aftertreatments, followed by purification through chromatography to obtain 39.2 g (yield: 85%) of trans-4-(trans-4-(4-(3-fluoro -4-trifluoromethoxyphenyl)butyl)cyclohexyl)-1-propyl-1-silacyclohexane.

EXAMPLE 57

Preparation of trans-4-(trans-4-(4-(3,5-difluoro-4-trifluoromethoxyphenyl)butyl)cyclohexyl)-1-propyl-1-silacyclohexane 34.5 g (0.1 mol) of trans-4-(trans-4-(3-bromopropyl)cyclohexyl)-1-propyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 29.1 g (0.1 mol) of 4-bromomethyl-2,6-difluoro-1-trichloromethoxybenzene. The resultant product was subjected to ordinary aftertreatments, followed by purification through chromatography to obtain 39.1 g (yield: 82%) of trans-4-(trans-4-(4-(3,5-difluoro-4-trifluoromethoxyphenyl)butyl)cyclohexyl)-1-propyl-1-silacyclohexane.

EXAMPLE 58

Preparation of trans-4-(trans-4-(4-(3-fluoro-4-trifluoromethoxyphenyl)butyl)cyclohexyl)-1-pentyl-1-silacyclohexane 37.4 g (0.1 mol) of trans-4-(trans-4-(3-bromopropyl)cyclohexyl)-1-pentyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 27.3 g (0.1 mol) of 4-bromomethyl-2-fluoro-1-trichloromethoxybenzene. The resultant product was subjected to ordinary aftertreatments, followed by purification through chromatography to obtain 41.8 g (yield: 86%) of trans-4-(trans-4-(4-(3-fluoro -4-trifluoromethoxyphenyl)butyl)cyclohexyl)-1-pentyl-1-silacyclohexane.

EXAMPLE 59

Preparation of trans-4-(trans-4-(4-(3-fluoro-4-difluoromethoxyphenyl)-1-silacyclohexyl)butyl)-1-pentyl-1-silacyclohexane 39.0 g (0.1 mol) of trans-4-(trans-4-(3-bromopropyl)-1-silacylohexyl)-1-pentyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 25.5 g (0.1 mol) of 4-bromomethyl-2-fluoro-1-dichloromethoxybenzene. The resultant product was subjected to ordinary aftertreatments, followed by purification through chromatography to obtain 38.0 g (yield: 81%) of trans-4-(trans-4-(4-(3-fluoro -4-difluoromethoxyphenyl)-1-silacyclohexyl)butyl)-1-pentyl-1 -silacyclohexane.

EXAMPLE 60

Preparation of trans-4-(trans-4-(4-methoxyphenyl)butyl)-1-pentyl-1-silacyclohexane 29.1 g (0.1 mol) of trans-4-(trans-4-(3-bromopropyl)-1-pentyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 20.1 g (0.1 mol) of 4-bromomethylanisole. The resultant product was subjected to ordinary aftertreatments, followed by purification through chromatography to obtain 27.0 g (yield: 81%) of trans-4-(trans-4-(4-methoxyphenyl)butyl)-1-pentyl-1-silacyclohexane.

EXAMPLE 61

Preparation of trans-4-(trans-4-(4-(3,4-difluorophenyl)butyl)cyclohexyl)-1-pentyl-4-methyl-4-silacyclohexane 20.7 g (0.1 mol) of4-bromomethyl-1,2-difluorobenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 38.8 g (0.1 mol) of trans-4-(trans-4-(3-bromopropyl)cyclohexyl)-1-pentyl-4-methyl-4-silacyclohexane. The resultant product was subjected to ordinary aftertreatments, followed by purification through chromatography to obtain 33.7 g (yield: 78%) of trans-4-(trans-4-(4-(3,4-difluorophenyl)butyl)cyclohexyl)-1-pentyl-4-methyl-4-silacyclohexane.

EXAMPLE 62

Preparation of trans-4-(trans-4-(4-(2,3-difluoro-4-ethoxyphenyl)cyclohexyl)butyl)-1-pentyl-1-silacyclohexane 25.1 g (0.1 mol) of 4-bromomethyl-2,3-difluorophenetole was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 37.4 g (0.1 mol) of trans-4-(trans-4-(3-bromopropyl)cyclohexyl)-1-pentyl-1-silacyclohexane. The resultant product was subjected to ordinary aftertreatments, followed by purification through chromatography to obtain 34.2 g (yield: 74%) of trans-4-(trans-4-(4-(2,3-difluoro-4-ethoxyphenyl)cyclohexyl)butyl)-1-pentyl-1-silacyclohexane.

EXAMPLE 63

Preparation of trans-4-(trans-4-(4-(3,4-difluorophenyl)butyl)cyclohexyl)-1-propyl-1-silacyclohexane 20.7 g (0.1 mol) of 4-bromomethyl-1,2-difluorobenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 34.5 g (0.1 mol) of trans-4-(trans-4-(3-bromopropyl)cyclohexyl)-1-pentyl-1-silacyclohexane. The resultant product was subjected to ordinary aftertreatments, followed by purification through chromatography to obtain 30.2 g (yield: 77%) of trans-4-(trans-4-(4-(3,4-difluorophenyl)butyl)cyclohexyl)-1-propyl-1-silacyclohexane.

EXAMPLE 64

Preparation of trans-4-(trans-4-(4-(2,3-difluoro-4-ethylphenyl)butyl)cyclohexyl)-1-pentyl-1-silacyclohexane 23.5 g (0.1 mol) of 4-bromomethyl-2,3-difluoro-1-ethylbenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 37.4 g (0.1 mol) of trans-4-(trans-4-(3-bromopropyl)cyclohexyl)-1-pentyl-1-silacyclohexane. The resultant product was subjected to ordinary aftertreatments, followed by purification through chromatography to obtain 35.1 g (yield: 78%) of trans-4-(trans-4-(4-(2,3-difluoro-4-ethylphenyl)butyl)cyclohexyl)-1-pentyl-1-silacyclohexane.

EXAMPLE 65

Preparation of trans-4-(trans-4-(4-(3,4-difluorophenyl)butyl)cyclohexyl)-1-butyl-1-silacyclohexane 20.7 g (0.1 mol) of 4-bromomethyl-1,2-difluorobenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 36.0 g (0.1 mol) of trans-4-(trans-4-(3-bromopropyl)cyclohexyl)-1-butyl-1-silacyclohexane. The resultant product was subjected to ordinary aftertreatments, followed by purification through chromatography to obtain 28.9 g (yield: 71%) of trans-4-(trans-4-(4-(3,4-difluorophenyl)butyl)cyclohexyl)-1-butyl-1-silacyclohexane.

EXAMPLE 66

Preparation of trans-4-(trans-4-(2,3-difluoro-4-ethoxyphenyl)butyl)-1-pentyl-1-silacyclohexane 25.1 g (0.1 mol) of 4-bromomethyl-2,3-difluorophenetole was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 29.1 g (0.1 mol) of trans-4-(3-bromopropyl)-1-pentyl-1-silacyclohexane. The resultant product was subjected to ordinary aftertreatments, followed by purification through chromatography to obtain 29.8 g (yield: 78%) of trans -4-(trans-4-(2,3-difluoro-4-ethoxyphenyl)butyl)-1-pentyl-1-silacyclohexane.

EXAMPLE 67

Preparation of trans-4-(trans-4-(4-(4-chlorofluoromethoxyphenyl)butyl)cyclohexyl)-1-propyl-1-silacyclohexane 36.0 g (0.1 mol) of trans-4-(trans-4-(4-bromobutyl)cyclohexyl)-1-propyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of tetrakistriphenylphosphine palladium and 24.0 g (0.1 mol) of 1-bromo-4-chlorofluoromethoxybenzene. The resultant product was subjected to ordinary aftertreatments, followed by purification through chromatography to obtain 35.7 g (yield: 81%) of trans-4-(trans-4-(4-(4-chlorofluoromethoxyphenyl)butyl)cyclohexyl)-1-propyl-1-silacyclohexane.

EXAMPLE 68

Preparation of trans-4-(trans-4-(4-(3-fluoro-4-chlorodifluoromethoxyphenyl)butyl)cyclohexyl)-1-propyl-1-silacyclohexane 36.0 g (0.1 mol) of trans-4-(trans-4-(4-bromobutyl)cyclohexyl)-1-propyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of tetrakistriphenylphosphine palladium and 27.6 g (0.1 mol) of 1-bromo-4-chlorodifluoromethoxy-3-fluorobenzene. The resultant product was subjected to ordinary aftertreatments, followed by purification through chromatography to obtain 40.7 g (yield: 86%) of trans-4-(trans-4-(4-(3-fluoro-4-chlorodifluoromethoxyphenyl)butyl)cyclohexyl)-1-propyl-1 -silacyclohexane.

EXAMPLE 69

Preparation of trans-4-(trans-4-(4-(3,5-difluoro-4-difluoromethoxyphenyl)butyl)cyclohexyl)-1-propyl-1-silacyclohexane 36.0 g (0.1 mol) of trans-4-(trans-4-(4-bromobutyl)cyclohexyl)-1-propyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of tetrakistriphenylphosphine palladium and 25.9 g (0.1 mol) of 1-bromo-4-difluoroethoxy-3,5-difluorobenzene. The resultant product was subjected to ordinary aftertreatments, followed by purification through chromatography to obtain 40.6 g (yield: 89%) of trans-4-(trans-4-(4-(3,5-difluoro-4-difluoromethoxyphenyl)butyl)cyclohexyl)-1-propyl-1-silacyclohexane.

EXAMPLE 70

Preparation of trans-4-(trans-4-(4-(3-fluoro-4-difluoromethoxyphenyl)butyl)cyclohexyl)-1-propyl-1-silacyclohexane 36.0 g (0.1 mol) of trans-4-(trans-4-(4-bromobutyl)cyclohexyl)-1-propyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of tetrakistriphenylphosphine palladium and 24.1 g (0.1 mol) of 1-bromo-4-difluoromethoxy-3-fluorobenzene. The resultant product was subjected to ordinary aftertreatments, followed by purification through chromatography to obtain 38.6 g (yield: 89%) of trans-4-(trans-4-(4-(3-fluoro-4-difluoromethoxyphenyl)butyl)cyclohexyl)-1-propyl-1-silacyclohexane.

EXAMPLE 71

Preparation of trans-4-(trans-4-(4-(4-trifluoromethoxyphenyl)butyl)cyclohexyl)-1-ethyl-1-silacyclohexane 34.5 g (0.1 mol) of trans-4-(trans-4-(4-bromobutyl)cyclohexyl)-1-ethyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of tetrakistriphenylphosphine palladium and 24.1 g (0.1 mol) of 1-bromo-4-trifluoromethoxybenzene. The resultant product was subjected to ordinary aftertreatments, followed by purification through chromatography to obtain 33.7 g (yield: 79%) of trans-4-(trans-4-(4-(4-trifluoromethoxyphenyl)butyl)cyclohexyl)-1-ethyl-1-silacyclohexane.

EXAMPLE 72

Preparation of trans-4-(4-(4-propylphenyl)butyl)-1-pentyl-1-silacyclohexane 30.5 g (0.1 mol) of trans-4-(4-bromobutyl)-1-pentyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of tetrakistriphenylphosphine palladium and 24.6 g (0.1 mol) of 4-propyliodobenzene. The resultant product was subjected to ordinary aftertreatments, followed by purification through chromatography to obtain 28.3 g (yield: 82%) of trans-4-(4-(4-propylphenyl)butyl)-1-pentyl-1-silacyclohexane.

EXAMPLE 73

Preparation of trans-4-(trans-4-(4-(4-chloro-3-fluorophenyl)butyl)cyclohexyl)-1-propyl-1-silacyclohexane 20.9 g (0.1 mol) of 1-bromo-3-fluoro-4-chlorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide, and 36.0 g (0.1 mol) of trans-4-(trans-4-(4-bromobutyl)cyclohexyl)-1-propyl-1-silacyclohexane. The resultant product was subjected to ordinary aftertreatments, followed by purification through chromatography to obtain 36.0 g (yield: 88%) of trans-4-(trans-4-(4-(4-chloro-3-fluorophenyl)butyl) cyclohexyl)-1-propyl-1-silacyclohexane.

EXAMPLE 74

Preparation of trans-4-(trans-4-(4-(2,3-difluoro-4-propylphenyl)butyl)cyclohexyl)-1-propyl-1-silacyclohexane 23.5 g (0.1 mol) of 1-bromo-2,3-difluoro-4-propylbenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide, and 36.0 g (0.1 mol) of trans-4-(trans-4-(4-bromobutyl)cyclohexyl)-1-propyl-1-silacyclohexane. The resultant product was subjected to ordinary aftertreatments, followed by purification through chromatography to obtain 34.9 g (yield: 80%) of trans-4-(trans-4-(4-(2,3-difluoro-4-propylphenyl)butyl)cyclohexyl)-1-propyl-1-silacyclohexane.

EXAMPLE 75

Preparation of trans-4-(trans-4-(4-(4-chloro-3-fluorophenyl)butyl)cyclohexyl)-1-pentyl-1-silacyclohexane 20.9 g (0.1 mol) of 1-bromo-3-fluoro-4-chlorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide, and 38.8 g (0.1 mol) of trans-4-(trans-4-(4-bromobutyl)cyclohexyl)-1-pentyl-1-silacyclohexane. The resultant product was subjected to ordinary aftertreatments, followed by purification through chromatography to obtain 33.3 g (yield: 76%) of trans-4-(trans-4-(4-(4-chloro-3-fluorophenyl)butyl)cyclohexyl)-1-pentyl-1-silacyclohexane.

EXAMPLE 76

Preparation of trans-4-(trans-4-(4-(3,4-difluorophenyl)butyl)cyclohexyl)-1-pentyl-1-silacyclohexane 19.3 g (0.1 mol) of 1-bromo-3,4-difluorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide, and 38.8 g (0.1 mol) of trans-4-(trans-4-(4-bromobutyl)cyclohexyl)-1-pentyl-1-silacyclohexane. The resultant product was subjected to ordinary aftertreatments, followed by purification through chromatography to obtain 36.6 g (yield: 87%) of trans-4-(trans-4-(4-(3,4-difluorophenyl)butyl)cyclohexyl)-1-pentyl-1-silacyclohexane.

EXAMPLE 77

Preparation of trans-4-(trans-4-(4-(3,4,5-trifluorophenyl)-1-silacylohexyl)butyl)-1-pentyl-1-silacyclohexane 21.1 g (0.1 mol) of 1-bromo-3,4,5-trifluorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide, and 40.4 g (0.1 mol) of trans-4-(trans-4-(4-bromobutyl)-1-silacylohexyl)-1-pentyl-1-silacyclohexane. The resultant product was subjected to ordinary aftertreatments, followed by purification through chromatography to obtain 39.6 g (yield: 87%) of trans-4-(trans-4-(4-(3,4,5-trifluorophenyl)-1-silacylohexyl)butyl)-1-pentyl-1-silacyclohexane.

EXAMPLE 78

Preparation of trans-4-(trans-4-(4-chloro-3-fluorophenyl)butyl)-1-pentyl-1-silacyclohexane 20.9 g (0.1 mol) of 1-bromo-3-fluoro-4-chlorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide, and 30.5 g (0.1 mol) of trans-4-(4-bromobutyl)-1-pentyl-1-silacyclohexane. The resultant product was subjected to ordinary aftertreatments, followed by purification through chromatography to obtain 31.1 g (yield: 88%) of trans -4- (trans-4-(4-chloro-3-fluorophenyl)butyl)-1-pentyl-1-silacyclohexane.

EXAMPLE 79

Preparation of trans-4-(trans-4-(4-(4-(2-fluoroethoxy)phenyl)butyl)cyclohexyl)-1-propyl-1-silacyclohexane The general procedure of Example 67 was repeated using 1-bromo-4-(2-fluoroethoxy)benzene, thereby obtaining the intended product.

EXAMPLE 80

Preparation of trans-4-(trans-4-(4-(4-(2,2-difluoroethoxy)phenyl)butyl)cyclohexyl)-1-propyl-1-silacyclohexane The general procedure of Example 67 was repeated using 1-bromo-4-(2,2-difluoroethoxy)benzene, thereby obtaining the intended product.

EXAMPLE 81

Preparation of trans-4-(trans-4-(4-(4-(2,2,2-trifluoroethoxy)phenyl)butyl)cyclohexyl)-1-propyl-1-silacyclohexane The general procedure of Example 67 was repeated using 1-bromo-4-(2,2,2-trifluoroethoxy)benzene, thereby obtaining the intended product.

EXAMPLE 82

Preparation of trans-4-(trans-4-(4-(4-(3-chloropropoxy)phenyl)butyl)cyclohexyl)-1-propyl-1-silacyclohexane The general procedure of Example 67 was repeated using 1-bromo-4-(3-chloropropoxy)benzene, thereby obtaining the intended product.

EXAMPLE 83

Preparation of trans-4-(trans-4-(4-(4-(3,3,3-trifluoropropoxy)phenyl)butyl)cyclohexyl)-1-propyl-1-silacyclohexane The general procedure of Example 67 was repeated using 1-bromo-4-(3,3,3-trifluoropropoxy)benzene, thereby obtaining the intended product.

EXAMPLE 84

Preparation of trans-4-(trans-4-(4-(4-(2,2,3,3,-tetrafluoropropoxy)phenyl)butyl)cyclohexyl)-1-propyl-1-silacyclohexane The general procedure of Example 67 was repeated using 1-bromo-4-(2,2,3,3-tetrafluoropropoxy)benzene, thereby obtaining the intended product.

EXAMPLE 85

Preparation of trans-4-(trans-4-(4-(4-(2,2,3,3,3-pentafluoropropoxy)phenyl)butyl)cyclohexyl)-1-propyl-1-silacyclohexane The general procedure of Example 67 was repeated using 1-bromo-4-(2,2,3,3,3-pentafluoropropoxy)benzene, thereby obtaining the intended product.

EXAMPLE 86

Preparation of trans-4-(trans-4-(4-(3-fluoro-4-(2-fluoroethoxy)phenyl)butyl)cyclohexyl)-1-pentyl-1-silacyclohexane The general procedure of Example 67 was repeated using 1-bromo-3-fluoro-4-(2-fluoroethoxy)benzene and trans-4-(trans-4-(bromobutyl)cyclohexyl-1-pentyl-1-silacyclohexane, thereby obtaining the intended product.

EXAMPLE 87

Preparation of trans-4-(trans-4-(4-(3-fluoro-4-(2,2-difluoroethoxy)phenyl)butyl)cyclohexyl)-1-pentyl-1-silacyclohexane The general procedure of Example 67 was repeated using 1-bromo-3-fluoro-4-(2,2-difluoroethoxy)benzene and trans-4-(trans-4-(bromobutyl)cyclohexyl-1-pentyl-1-silacyclohexane, thereby obtaining the intended product.

EXAMPLE 88

Preparation of trans-4-(trans-4-(4-(3-fluoro-4-(2,2,2-trifluoroethoxy)phenyl)butyl)cyclohexyl)-1-pentyl-1-silacyclohexane The general procedure of Example 67 was repeated using 1-bromo-3-fluoro-4-(2,2,2-trifluoroethoxy)benzene and trans-4-(trans-4-(bromobutyl)cyclohexyl-1-pentyl-1-silacyclohexane, thereby obtaining the intended product

EXAMPLE 89

Preparation of trans-4-(trans-4-(4-(3-fluoro-4-(3-chloropropoxy)phenyl)butyl)cyclohexyl)-1-pentyl-1-silacyclohexane The general procedure of Example 67 was repeated using 1-bromo-3-fluoro-4-(3-chloropropoxy)benzene and trans-4-(trans-4-(bromobutyl)cyclohexyl-1-pentyl-1-silacyclohexane, thereby obtaining the intended product.

EXAMPLE 90

Preparation of trans-4-(trans-4-(4-(3-fluoro-4-(3,3,-trifluoropropoxy)phenyl)butyl)cyclohexyl)-1-pentyl-1-silacyclohexane The general procedure of Example 67 was repeated using 1-bromo-3-fluoro-4-(3,3,3-trifluoropropoxy)benzene and trans-4-(trans-4 -(bromobutyl)cyclohexyl-1-pentyl-1-silacyclohexane, thereby obtaining the intended product.

EXAMPLE 91

Preparation of trans-4-(trans-4-(4-(3-fluoro-4-(2,2,3,3-tetrafluoropropoxy)phenyl)butyl)cyclohexyl)-1-pentyl-1-silacyclohexane The general procedure of Example 67 was repeated using 1-bromo-3-fluoro-4-(2,2,3,3-tetrafluoropropoxy)benzene and trans-4-(trans-4-(bromobutyl)cyclohexyl-1-pentyl-1-silacyclohexane, thereby obtaining the intended product.

EXAMPLE 92

Preparation of trans-4-(trans-4-(4-(3-fluoro-4-(2,2,3,3,3,-pentafluoropropoxy)phenyl)cyclohexyl)-1-pentyl-1-silacyclohexane The general procedure of Example 67 was repeated using 1-bromo-3-fluoro-4-(2,2,3,3,3-tetrafluoropropoxy)benzene

EXAMPLE 93

Preparation of trans-4-(trans-4-(4-(3,5-difluoro-4-(2-fluoroethoxy)phenyl)butyl)cyclohexyl)-1-pentyl-1-silacyclohexane The general procedure of Example 67 was repeated using 1-bromo-3,5-difluoro-4-(2-fluoroethoxy)benzene and trans-4-(trans-4-(bromobutyl)cyclohexyl-1-pentyl-1-silacyclohexane, thereby obtaining the intended product.

EXAMPLE 94

Preparation of trans-4-(trans-4-(4-(3,5-difluoro-4-(2,2-difluoroethoxy)phenyl)butyl)cyclohexyl)-1-pentyl-1-silacyclohexane The general procedure of Example 67 was repeated using 1-bromo-3,5-difluoro-4-(2,2-difluoroethoxy)benzene and trans-4-(trans-4-(bromobutyl)cyclohexyl-1-pentyl-1-silacyclohexane, thereby obtaining the intended product.

EXAMPLE 95

Preparation of trans-4-(trans-4-(4-(3,5-difluoro-4-(2,2,2-trifluoroethoxy)phenyl)butyl)cyclohexyl)-1-pentyl-1-silacyclohexane The general procedure of Example 67 was repeated using 1-bromo-3,5-difluoro-4-(2,2,2-trifluoroethoxy)benzene and trans-4-(trans-4-(bromobutyl)cyclohexyl-1-pentyl-1-silacyclohexane, thereby obtaining the intended product.

EXAMPLE 96

Preparation of trans-4-(trans-4-(4-(3,5-difluoro-4-(3-chloropropoxy)phenyl)butyl)cyclohexyl)-1-pentyl-1-silacyclohexane The general procedure of Example 67 was repeated using 1-bromo-3,5-difluoro-4-(3-chloropropoxy)benzene and trans-4-(trans-4-(bromobutyl)cyclohexyl-1-pentyl-1-silacyclohexane, thereby obtaining the intended product.

EXAMPLE 97

Preparation of trans-4-(trans-4-(4-(3,5-difluoro-4-(3,3,3-trifluoropropoxy)phenyl)butyl)cyclohexyl)-1-pentyl-1-silacyclohexane The general procedure of Example 67 was repeated using 1-bromo-3,5-difluoro-4-(3,3,3-trifluoropropoxy)benzene and trans-4-(trans-4-(bromobutyl)cyclohexyl-1-pentyl-1-silacyclohexane, thereby obtaining the intended product.

EXAMPLE 98

Preparation of trans-4-(trans-4-(4-(3,5-difluoro-4-(2,2,3,3-tetrafluoropropoxy)phenyl)butyl)cyclohexyl)-1-pentyl-1-silacyclohexane The general procedure of Example 67 was repeated using 1-bromo-3,5-difluoro-4-(2,2,3,3-tetrafluoropropoxy)benzene and trans-4-(trans-4-(bromobutyl) cyclohexyl-1-pentyl-1- silacyclohexane, thereby obtaining the intended product.

EXAMPLE 99

Preparation of trans-4-(trans-4-(4-(3,5-difluoro-4-(2,2,3,3,3-pentafluoropropoxy)phenyl)butyl)cyclohexyl)-1-pentyl-1-silacyclohexane The general procedure of Example 67 was repeated using 1-bromo-3,5-difluoro-4-(2,2,3,3,3-pentafluoropropoxy) benzene and trans-4-(trans-4-(bromobutyl)cyclohexyl-1-pentyl-1-silacyclohexane, thereby obtaining the intended product.

EXAMPLE 100

Preparation of trans-4-(trans-4-(4-(4-(2,2-difluorovinyl)phenyl)butyl)cyclohexyl)-1-pentyl-1-silacyclohexane The general procedure of Example 67 was repeated using 1-bromo-4-(2,2-difluorovinyl)benzene and trans-4-(trans-4-(bromobutyl)cyclohexyl-1-pentyl-1-silacyclohexane, thereby obtaining the intended product.

EXAMPLE 101

Preparation of trans-4-(trans-4-(4-(4-(2,2-difluorovinyloxy)phenyl)butyl)cyclohexyl)-1-pentyl-1-silacyclohexane The general procedure of Example 67 was repeated using 1-bromo-4-(2,2-difluorovinyloxy)benzene and trans-4-(trans-4-(bromobutyl)cyclohexyl -1-pentyl-1-silacyclohexane, thereby obtaining the intended product.

EXAMPLE 102

Preparation of trans-4-(trans-4-(4-(4-(1,2-difluorovinyl)phenyl)butyl)cyclohexyl)-1 -pentyl-1-silacyclohexane The general procedure of Example 67 was repeated using 1-bromo-4 -(1,2-difluorovinyl)benzene and trans-4-(trans-4-(bromobutyl)cyclohexyl-1-pentyl-1-silacyclohexane, thereby obtaining the intended product.

EXAMPLE 103

Preparation of trans-4-(trans-4-(4-(4-(1,2,2-trifluorovinyl)phenyl)butyl)cyclohexyl)-1-pentyl-1-silacyclohexane The general procedure of Example 67 was repeated using 1-bromo-4-(1,2,2-trifluorovinyl)benzene and trans-4-(trans-4-(bromobutyl)cyclohexyl -1-pentyl-1-silacyclohexane, thereby obtaining the intended product.

EXAMPLE 104

Preparation of trans-4-(trans-4-(4-(4-(1,2,2-trifluorovinyloxy)phenyl)butyl)cyclohexyl)-1-pentyl-1-silacyclohexane The general procedure of Example 67 was repeated using 1-bromo-4-(1,2,2-trifluorovinyloxy)benzene and trans-4-(trans-4-(bromobutyl)cyclohexyl-1-pentyl-1-silacyclohexane, thereby obtaining the intended product.

EXAMPLE 105

Preparation of trans-4-(trans-4-(4-(4-(2-chloro-1-fluorovinyl)phenyl)butyl)cyclohexyl)-1-pentyl-1-silacyclohexane The general procedure of Example 67 was repeated using 1-bromo-4-(2-chloro-1-fluorovinyl)benzene and trans-4-(trans-4-(bromobutyl)cyclohexyl-1-pentyl-1-silacyclohexane, thereby obtaining the intended product.

EXAMPLE 106

Preparation of trans-4-(trans-4-(4-(4-(1,2-dichlorovinyl)phenyl)butyl)cyclohexyl)-1-pentyl-1-silacyclohexane The general procedure of Example 67 was repeated using 1-bromo-4-(1,2-dichlorovinyl)benzene and trans-4-(trans-4-

(bromobutyl)cyclohexyl-1-pentyl-1-silacyclohexane, thereby obtaining the intended product.

EXAMPLE 107

Preparation of trans-4-(trans-4-(4-(4-(2,2-dichlorovinyl)phenyl)butyl)cyclohexyl)-1-pentyl-1-silacyclohexane The general procedure of Example 67 was repeated using 1-bromo-4-(2,2-dichlorovinyl)benzene and trans-4-(trans-4-(bromobutyl)cyclohexyl-1-pentyl-1-silacyclohexane, thereby obtaining the intended product.

EXAMPLE 108

Preparation of trans-4-(trans-4-(4-(3-fluoro-4-(2,2-difluorovinyloxy)phenyl)butyl)cyclohexyl)-1-pentyl-1-silacyclohexane The general procedure of Example 67 was repeated using 1-bromo-3-fluoro-4-(2,2-difluorovinyloxy)benzene and trans-4-(trans-4-(bromobutyl)cyclohexyl-1-pentyl-1-silacyclohexane, thereby obtaining the intended product.

EXAMPLE 109

Preparation of trans-4-(trans-4-(4-(3-fluoro-4-(1,2-difluorovinyl)phenyl)butyl)cyclohexyl)-1-pentyl-1-silacyclohexane The general procedure of Example 67 was repeated using 1-bromo-3-fluoro-4-(1,2-difluorovinyl)benzene and trans-4-(trans-4-(bromobutyl)cyclohexyl-1-pentyl-1-silacyclohexane, thereby obtaining the intended product.

EXAMPLE 110

Preparation of trans-4-(trans-4-(4-(3-fluoro-4-(1,2,2-trifluorovinyloxy)phenyl)butyl)cyclohexyl)-1-pentyl-1-silacyclohexane The general procedure of Example 67 was repeated using 1-bromo-3-fluoro-4-(1,2,2-trifluorovinyloxy)benzene and trans-4-(trans-4-(bromobutyl)cyclohexyl-1-pentyl-1-silacyclohexane, thereby obtaining the intended product.

EXAMPLE 111

Preparation of trans-4-(trans-4-(4-(3-fluoro-4-(2-chloro-1-fluorovinyl)phenyl)butyl)cyclohexyl)-1-pentyl-1-silacyclohexane The general procedure of Example 67 was repeated using 1-bromo-3-fluoro-4-(2-chloro-1-fluorovinyl)benzene and trans-4-(trans-4-(bromobutyl) cyclohexyl-1-pentyl-1-silacyclohexane, thereby obtaining the intended product.

EXAMPLE 112

Preparation of trans-4-(trans-4-(4-(3,5-difluoro-4-(2,2-difluorovinyloxy)phenyl)butyl)cyclohexyl)-1-pentyl-1-silacyclohexane The general procedure of Example 67 was repeated using 1-bromo-3,5-difluoro-4-(2,2-difluorovinyloxy)benzene and trans-4-(trans-4-(bromobutyl)cyclohexyl-1-pentyl-1-silacyclohexane, thereby obtaining the intended product.

EXAMPLE 113

Preparation of trans-4-(trans-4-(4-(3,5-difluoro-4-(1,2-difluorovinyl)phenyl)butyl)cyclohexyl)-1-pentyl-1-silacyclohexane The general procedure of Example 67 was repeated using 1-bromo-3,5-difluoro-4-(1,2-difluorovinyl)benzene and trans-4-(trans-4-(bromobutyl)cyclohexyl-1-pentyl-1-silacyclohexane, thereby obtaining the intended product.

EXAMPLE 114

Preparation of trans-4-(trans-4-(4-(3,5-difluoro-4-(1,2,2-trifluorovinyl)phenyl)butyl)cyclohexyl)-1-pentyl-1-silacyclohexane The general procedure of Example 67 was repeated using 1-bromo-3,5-difluoro-4-(1,2,2-trifluorovinyl)benzene and trans-4-(trans-4-(bromobutyl)cyclohexyl-1-pentyl-1-silacyclohexane, thereby obtaining the intended product.

EXAMPLE 115

Preparation of trans-4-(trans-4-(4-(3,5-difluoro-4-(1,2,2-trifluorovinyloxy)phenyl)butyl)cyclohexyl)-1-pentyl-1-silacyclohexane The general procedure of Example 67 was repeated using 1-bromo-3,5-difluoro-4-(1,2,2-trifluorovinyloxy)benzene and trans-4-(trans-4-(bromobutyl)cyclohexyl-1-pentyl-1-silacyclohexane, thereby obtaining the intended product.

EXAMPLE 116

Preparation of trans-4-(trans-4-(4-(3,5-difluoro-4-(2-chloro-1-fluorovinyl)phenyl)butyl)cyclohexyl)-1-pentyl-1-silacyclohexane The general procedure of Example 67 was repeated using 1-bromo-3,5-difluoro-4-(2-chloro-1-fluorovinyl)benzene and trans-4-(trans-4-(bromobutyl)cyclohexyl-1-pentyl-1-silacyclohexane, thereby obtaining the intended product.

EXAMPLE 117

Preparation of trans-4-(trans-4-(4-(3,5-difluoro-4-(2,2-dichloro-1-fluorovinyl)phenyl)butyl)cyclohexyl)-1-pentyl-1-silacyclohexane The general procedure of Example 67 was repeated using 1-bromo-3,5-difluoro-4-(2,2-dichloro-1-fluorovinyl)benzene and trans-4-(trans-4-(bromobutyl)cyclohexyl-1-pentyl-1-silacyclohexane, thereby obtaining the intended product.

EXAMPLE 118

Preparation of trans-4-(4-(4-trans-4-(4-cyanophenyl)cyclohexyl)butyl)-1-n-propyl-1-silacyclohexane 50 ml (0.13 moles) of a THF solution of 2.5M of n-propylmagnesium chloride was dropped in a mixed solution of 37.4 g (0.1 mol) of 1-chloro-4-(4-(trans-4-(4-cyanophenyl)cyclohexyl)butyl)-1-silacyclohexane and 300 ml of THF. The resultant product was found to be a mixture of trans and cis isomers with respect to the silacyclohexane ring. The product was subjected to ordinary aftertreatments such as removal of the solvent and salts, followed by isolation through chromatography to obtain 38.2 g (yield: 88%) of the intended trans isomer product.

EXAMPLE 119

Preparation of trans-4-(4-(trans-4-(4-difluoromethoxyphenyl)cyclohexyl)butyl)-1-n-butyl-1-silacyclohexane 50 ml (0.13 moles) of a THF solution of 2.5M of n-butylmagnesium chloride was dropped in a mixed solution of 41.5 g (0.1 mol) of 1-chloro-4-(4-(trans-4-(4-difluoromethoxyphenyl)cyclohexyl)butyl)-1-silacyclohexane and 30 ml of THF. The resultant product was found to be a mixture of trans and cis isomers with respect to the silacyclohexane ring. The product was subjected to ordinary aftertreatments, followed by isolation through chromatography to obtain 43.7 g (yield: 90%) of the intended trans isomer product.

EXAMPLE 120

Preparation of trans-4-(4-(trans-4-(3-fluoro-4-difluoromethoxyphenyl)cyclohexyl)butyl)-1-ethyl-1-silacyclohexane 130 ml (0.13 moles) of a THF solution of 1M of ethylmagnesium bromide was dropped in a mixed solution of 43.3 g (10 mmols) of 1-chloro-4-(4-(trans-4-(3-fluoro-4-difluoromethoxyphenyl)cyclohexyl)butyl)-1-silacyclohexane and 30 ml of THF. The resultant product was found to be a mixture of trans and cis isomers with respect to the silacyclohexane ring. The product was subjected to ordinary aftertreatments, followed by isolation through chromatography to obtain 42.7 g (yield: 87%) of the intended trans isomer product.

EXAMPLE 121

Preparation of trans-4-(4-(trans-4-(4-cyanophenyl)cyclohexyl)butyl)-1-(4-pentenyl)-1-silacyclohexane 130 ml (0.13 mols) of a THF solution of 1M of 4-pentenylmagnesium bromide was dropped in a solution of 200 ml of THF and 14.0 g of zinc chloride to obtain an organozinc reagent. The resultant mixture was added to a solution of 41.0 g (0.1 mol) of 1-chloro-4-(4-(trans-4-(4-cyanophenyl)cyclohexyl)butyl)-1-silacyclohexane in 300 ml of THF. The resultant product was found to be a mixture of trans and cis isomers with respect to the silacyclohexane ring. The product was subjected to ordinary aftertreatments, followed by isolation through chromatography to obtain 40.8 g (yield: 95%) of the intended trans isomer product.

EXAMPLE 122

Preparation of trans-4-(4-trans-4-(3,5-difluoro-4-cyanophenyl)cyclohexyl)butyl)-1-pentyl-1-silacyclohexane 50 ml (0.13 mols) of a THF solution of 2.5M of n-pentylmagnesium chloride was dropped in a mixed solution of 41.0 g (0.1 mol) of 1-chloro-4-(4-(trans-4-(3,5-difluoro-4-cyanophenyl)cyclohexyl)butyl)-1-silacyclohexane and 300 ml of THF. The resultant product was found to be a mixture of trans and cis isomers with respect to the silacyclohexane ring. The product was subjected to ordinary aftertreatments, followed by isolation through chromatography to obtain 44.6 g (yield: 87%) of the intended trans isomer product.

EXAMPLE 123

Preparation of trans-4-(4-(trans-4-(4-trifluoromethylphenyl)cyclohexyl)butyl)-1-n-propyl-1-silacyclohexane 22.1 g (0.1 mol) of 1-bromo-4-n-propyl-4-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 36.3 g (0.1 mol) of 4-(trans-4-(4-bromobutyl)cyclohexyl)-1-trifluoromethylbenzene. The resultant product was subjected to ordinary aftertreatments to obtain trans-4-(4-(trans-4-(4-trifluoromethylphenyl)cyclohexyl)butyl)-1-n-propyl-1-silacyclohexane, followed by isolation through chromatography to obtain 42.5 g (yield: 75%) of the intended trans isomer product.

EXAMPLE 124

Preparation of trans-4-(4-(trans-4-(3-fluoro-4-cyanophenyl)cyclohexyl)butyl)-1-ethyl-1-silacyclohexane 20.7 g (0.1 mol) of 1-bromo-4-ethyl-4-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 33.8 g (0.1 mol) of 4-(trans-4-(4-bromobutyl)cyclohexyl)-2-fluorobenzonitrile. The resultant product was subjected to ordinary aftertreatments to obtain trans-4-(4-(trans -4-(3-fluoro-4-cyanophenyl)cyclohexyl)butyl)-1-ethyl-1-silacyclohexane, followed by isolation through chromatography to obtain 27.9 g (yield: 72%) of the intended trans isomer product.

EXAMPLE 125

Preparation of trans-4-(4-(trans-4-(3,5-difluoro-4-(2-fluoroethoxy)phenyl)cyclohexyl)butyl)-1-n-propyl-1-silacyclohexane 22.1 g (0.1 mol) of 1-bromo-4-n-propyl-4-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 39.1 g (0.1 mol) of 4-(trans-4-(4-bromobutyl)cyclohexyl)-2,6-difluoro-1-(2-fluoroethoxy)benzene. The resultant product was subjected to ordinary aftertreatments to obtain trans-4-(4-(trans-4-(3,5-difluoro-4-(2-fluoroethoxy)phenyl)cyclohexyl)butyl)-1-n-propyl-1-silacyclohexane, followed by isolation through chromatography to obtain 36.6 g (yield: 81%) of the intended trans isomer product.

EXAMPLE 126

Preparation of trans-4-(4-(trans-4-(4-trifluoromethylphenyl)cyclohexyl)butyl)-1-(3-methylbutyl)-1-silacyclohexane 24.9 g (0.1 mol) of 1-bromo-4-(3-methylbutyl)-4-silacyclohexane was dropped in a mixture of 2.5 g (0.11 mols) of magnesium and 300 ml of THF to obtain a Grignard reagent. The resultant solution was then dropped in a solution, in 500 ml of THF, of 1 g of dilithium tetrachlorocuprate ($Li_2CuCl_4$) and 43.9 g (0.1 mol) of 4-(trans-4-(4-trifluoromethylphenyl)cyclohexyl)butyl tosylate. The resultant product was subjected to ordinary aftertreatments to obtain trans-4-(4-(trans-4-(4-trifluoromethylphenyl)cyclohexyl)butyl)-1-(3-methylbutyl)-1-silacyclohexane, followed by isolation through chromatography to obtain 37.3 g (yield: 82%) of the intended trans isomer product.

EXAMPLE 127

Preparation of trans-4-(4-(trans-4-(3,5-difluoro-4-trifluoromethoxyphenyl)cyclohexyl)butyl)-1-(4-fluorobutyl)-1-silacyclohexane 25.3 g (0.1 mol) of 1-bromo-4-(4-fluorobutyl)-4-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 41.5 g (0.1 mol) of 4-(trans-4-(4-bromobutyl)cyclohexyl)-2,6-difluoro-1-trifluoromethoxybenzene. The resultant product was subjected to ordinary aftertreatments to obtain trans-4-(4-(trans-4-(3,5-difluoro-4-trifluoromethoxyphenyl)cyclohexyl)butyl)-1-(4-fluorobutyl)-1-silacyclohexane, followed by isolation through chromatography to obtain 37.3 g (yield: 82%) of the intended trans isomer product.

EXAMPLE 128

Preparation of trans-4-(4-(trans-4-(4-fluorophenyl)cyclohexyl)butyl)-1-n-propyl-1-silacyclohexane 31.3 g (0.1 mol) of 4-(trans-4-(4-bromobutyl)cyclohexyl)-1-fluorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 22.1 g (0.1 mol) of 1-bromo-4-n-propyl-4-silacyclohexane. The resultant product was subjected to ordinary aftertreatments to obtain trans-4-(4-(trans-4-(4-fluorophenyl)cyclohexyl)butyl)-1-n-propyl-1-silacyclohexane, followed by isolation through chromatography to obtain 19.6 g (yield: 52%) of the intended trans isomer product.

EXAMPLE 129

Preparation of trans-4-(4-(trans-4-(3-fluoro-4-n-propylphenyl)-1-silacyclohexyl)butyl)-1-ethylcyclohexane 37.1 g (0.1 mol) of 4-(trans-4-(4-bromobutyl)-4-silacyclohexyl)-2-fluoro-1-propylbenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 20.7 g (0.1 mol) of 1-bromo-4-ethylcyclohexane. The resultant product was subjected to ordinary aftertreatments to obtain trans-4-(4-(trans-4-(3-fluoro-4-n-propylphenyl)-1-silacyclohexyl)butyl)-1-ethylcyclohexane, followed by isolation through chromatography to obtain 20.3 g (yield: 50%) of the intended trans isomer product.

EXAMPLE 130

Preparation of trans-4-(4-(trans-4-(4-chlorophenyl)cyclohexyl)butyl)-1-n-propyl-1-silacyclohexane 33.0 g (0.1 mol) of 4-(trans-4-(4-bromobutyl)cyclohexyl)-1-chlorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 22.1 g (0.1 mol) of 1-bromo-4-n-propyl-4-silacyclohexane. The resultant product was subjected to ordinary aftertreatments to obtain trans-4-(4-(trans-4-(4-chlorophenyl)cyclohexyl)butyl)-1-n-propyl-1-silacyclohexane, followed by isolation through chromatography to obtain 20.0 g (yield: 51%) of the intended trans isomer product.

EXAMPLE 131

Preparation of trans-4-(4-(trans-4-(3-fluoro-4-n-propylphenyl)cyclohexyl)butyl)-1-n-butyl-1-silacyclohexane 35.5 g (0.1 mol) of 4-(trans-4-(4-bromobutyl)cyclohexyl)-2-fluoro-1-propylbenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 23.5 g (0.1 mol) of 1-bromo-4-n-butyl-4-silacyclohexane. The resultant product was subjected to ordinary aftertreatments to obtain trans-4-(4-(trans-4-(3-fluoro-4-n -propylphenyl)cyclohexyl)butyl)-1-n-butyl-1-silacyclohexane, followed by isolation through chromatography to obtain 19.8 g (yield: 46%) of the intended trans isomer product.

EXAMPLE 132

Preparation of trans-4-(4-(trans-4-(3,4,5-trifluorophenyl)cyclohexyl)butyl)-1-ethyl-1-silacyclohexane 34.9 g (0.1 mol) of 1-(trans-4-(4-bromobutyl)cyclohexyl)-3,4,5-trifluorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 20.7 g (0.1 mol) of 1-bromo-4-ethyl-4-silacyclohexane. The resultant product was subjected to ordinary aftertreatments to obtain trans-4-(4-(trans-4-(3,4,5-trifluorophenyl)cyclohexyl)butyl)-1-ethyl-1-silacyclohexane, followed by isolation through chromatography to obtain 19.7 g (yield: 50%) of the intended trans isomer product.

EXAMPLE 133

Preparation of trans-4-(4-(trans-4-(4-chlorodifluoromethylphenyl)cyclohexyl)butyl)-1-n-pentyl-1-silacyclohexane 26.3 g (0.1 mol) of trans-4-bromomethyl-1-n-pentyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 36.6 g (0.1 mol) of 4-(trans-4-(3-bromopropyl)cyclohexyl)-1-chlorodifluoromethylbenzene. The resultant product was subjected to ordinary aftertreatments to obtain trans-4-(4-(trans-4-(4-chlorodifluoromethylphenyl)cyclohexyl)butyl)-1-n-pentyl-1-silacyclohexane, followed by isolation through chromatography to obtain 38.3 g (yield: 82%) of the intended trans isomer product.

EXAMPLE 134

Preparation of trans-4-(4-(trans-4-(3-fluoro-4-trifluoromethylphenyl)cyclohexyl)butyl)-1-n-pentyl-1-silacyclohexane 26.3 g (0.1 mol) of trans-4-bromomethyl-1-n-pentyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of dilithium tetrachlorocuprate and 44.3 g (0.1 mol) of 3-(trans-4-(3-fluoro-4-trifluoromethylphenyl)cyclohexyl)propyl tosylate. The resultant product was subjected to ordinary aftertreatments to obtain trans-4-(4-(trans-4-(3-fluoro-4-trifluoromethylphenyl)cyclohexyl)butyl)-1-n-pentyl-1-silacyclohexane, followed by isolation through chromatography to obtain 38.0 g (yield: 81%) of the intended trans isomer product.

EXAMPLE 135

Preparation of trans-4-(4-(trans-4-(3,5-difluoro-4-(2,2-difluoroethoxy)phenyl)cyclohexyl)butyl)-1-n-pentyl-1-silacyclohexane 26.3 g (0.1 mol) of trans-4-bromomethyl-1-n-pentyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 44.8 g (0.1 mol) of 4-(trans-4-(3-iodopropyl)cyclohexyl)-2,6 -difluoro-1-(2,2-difluoroethoxy)benzene. The resultant product was subjected to ordinary aftertreatments to obtain trans-4-(4-(trans-4-(3,5-difluoro-4-(2,2-difluoroethoxy)phenyl)cyclohexyl) butyl)-1-n-pentyl-1-silacyclohexane, followed by isolation through chromatography to obtain 41.7 g (yield: 83%) of the intended trans isomer product.

EXAMPLE 136

Preparation of trans-4-(4-(trans-4-(4-trifluoromethoxyphenyl)cyclohexyl)butyl)-1-n-propyl-1-silacyclohexane 23.5 g (0.1 mol) of trans-4-bromomethyl-1-n-propyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 36.5 g (0.1 mol) of 4-(trans-4-(3-bromopropyl)cyclohexyl)-1-trifluoromethoxybenzene. The resultant product was subjected to ordinary aftertreatments to obtain trans-4-(4-(trans-4-(4-trifluoromethoxyphenyl)cyclohexyl)butyl)-1-n-propyl-1-silacyclohexane, followed by isolation through chromatography to obtain 36.9 g (yield: 84%) of the intended trans isomer product.

EXAMPLE 137

Preparation of trans-4-(4-(trans-4-(3,5-difluoro-4-trifluoromethylphenyl)-1-silacyclohexyl)butyl)-1-n-propylcyclohexane 21.9 g (0.1 mol) of trans-4-bromomethyl-1-n-propyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 40.1 g (0.1 mol) of 4-(trans-4-(3-bromopropyl)-4-silacyclohexyl) -2,6-difluoro-1-trifluormethylbenzene. The resultant product was subjected to ordinary aftertreatments to obtain trans-4-(4-(trans-4-(3,5-difluoro-4-trifluoromethylphenyl)-1-silacyclohexyl)butyl)-1 -n-propylcyclohexane, followed by isolation through chromatography to obtain 37.2 g (yield: 81%) of the intended trans isomer product.

EXAMPLE 138

Preparation of trans-4-(4-(trans-4-(4-(2-fluoroethoxy)phenyl)cyclohexyl)butyl)-1-n-pentyl-1-silacyclohexane 34.3 g (0.1 mol) of 4-(trans-4-(3-bromopropyl) cyclohexyl)-1-(2-fluoroethoxy)benzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 26.3 g (0.1 mol) of trans-4-bromomethyl-1-n-pentyl-1-silacyclohexane. The resultant product was subjected to ordinary aftertreatments to obtain trans-4-(4-(trans-4-(4-(2-fluoroethoxy) phenyl)cyclohexyl)butyl)-1-n-pentyl-1-silacyclohexane, followed by isolation through chromatography to Obtain 36.5 g (yield: 82%) of the intended trans isomer product.

EXAMPLE 139

Preparation of trans-4-(4-(trans-4-(3-fluoro-4-(2,2-difluorovinyloxy)phenyl)cyclohexyl)butyl)-1-n-butyl-1-silacyclohexane 37.7 g (0.1 mol) of 4-(trans-4-(3-bromopropyl) cyclohexyl)-2-fluoro-1-(2,2-difluorovinyloxy)benzene was dropped in a mixture of 2.5 g (0.11 mols) of magnesium and 300 ml of THF to obtain a Grignard reagent. The resultant solution was then dropped in a solution, in 500 ml of THF, of 0.5 g of dilithium tetrachlorocuprate and 32.5 g (0.1 mol) of trans-4-n-butyl-4-silacyclohexyl methyltosylate. The resultant product was subjected to ordinary aftertreatments to obtain trans-4-(4-(trans-4-(3-fluoro-4-(2,2-difluorovinyloxy)phenyl)cyclohexyl)butyl)-1-n-butyl-1-silacyclohexane, followed by isolation through chromatography to obtain 37.1 g (yield: 79%) of the intended trans isomer product.

EXAMPLE 140

Preparation of trans-4-(4-(trans-4-(4-(2,2-difluorovinyl)phenyl)cyclohexyl)butyl)-1-n-pentyl-1-silacyclohexane 34.3 g (0.1 mol) of 4-(trans-4-(3-bromopropyl) cyclohexyl)-1-(2,2-difluorovinyl)benzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I)iodide and 26.3 g (0.1 mol) of trans-4-bromomethyl-1-n-pentyl-1-silacyclohexane. The resultant product was subjected to ordinary aftertreatments to obtain trans-4-(4-(trans-4-(4-(2,2-difluorovinyl) phenyl)cyclohexyl)butyl)-1-n-pentyl-1-silacyclohexane, followed by isolation through chromatography to obtain 31.6 g (yield: 71%) of the intended trans isomer product.

EXAMPLE 141

Preparation of trans-4-(4-(trans-4-(3-fluoro-4-ethoxyphenyl)cyclohexyl)butyl)-1-n-pentyl-1-silacyclohexane 34.3 g (0.1 mol) of 4-(trans-4-(3-bromopropyl) cyclohexyl)-2-fluorophenetole was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 26.3 g (0.1 mol) of trans-4-bromomethyl-1-n -pentyl-1-silacyclohexane. The resultant product was subjected to ordinary aftertreatments to obtain trans-4-(4-(trans-4-(3-fluoro-4-ethoxyphenyl) cyclohexyl)butyl)-1-n-pentyl-1-silacyclohexane, followed by isolation through chromatography to obtain 36.0 g (yield: 81%) of the intended trans isomer product.

EXAMPLE 142

Preparation of trans-4-(4-(trans-4-(3,4,5-trifluorophenyl)cyclohexyl)butyl) -1-n-pentyl-1-silacyclohexane 33.5 g (0.1 mol) of 1-(trans-4-(3-bromopropyl) cyclohexyl)-3,4,5-trifluorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 21.9 g (0.1 mol) of trans-4-n-pentyl-1-chloromethyl-1-silacyclohexane. The resultant product was subjected to ordinary aftertreatments to obtain trans-4-(4-(trans-4-(3,4,5-trifluorophenyl)cyclohexyl)butyl)-1-n-pentyl-1-silacyclohexane, followed by isolation through chromatography to obtain 34.7 g (yield: 79%) of the intended trans isomer product.

EXAMPLE 143

Preparation of trans-4-(4-(trans-4-(4-chlorofluoromethylphenyl)cyclohexyl)butyl)-1-n-pentyl-1-silacyclohexane 27.7 g (0.1 mol) of trans-4-(2-bromoethyl)-1-n-pentyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 33.4 g (0.1 mol) of 4-(trans-4-(2-bromoethyl)cyclohexyl)-1-fluorochloromethylbenzene. The resultant product was subjected to ordinary aftertreatments to obtain trans-4-(4-(trans-4-(4-chlorofluoromethylphenyl)cyclohexyl)butyl)-1-n-pentyl-1-silacyclohexane, followed by isolation through chromatography to obtain 39.3 g (yield: 87%) of the intended trans isomer product.

EXAMPLE 144

Preparation of trans-4-(4-(trans-4-(3-fluoro-4-chlorodifluoromethylphenyl)cyclohexyl)butyl)-1-n-pentyl-1-silacyclohexane 27.7 g (0.1 mol) of trans-4-(2-bromoethyl)-1-n-pentyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 37.0 g (0.1 mol) of 4-(trans-4-(2-bromoethyl)cyclohexyl)-2-fluoro-1-difluorochloromethylbenzene. The resultant product was subjected to ordinary aftertreatments to obtain trans-4-(4-(trans-4-(3-fluoro-4-chlorodifluoromethylphenyl)cyclohexyl)butyl)-1-n-pentyl-1-silacyclohexane, followed by isolation through chromatography to obtain 43.2 g (yield: 89%) of the intended trans isomer product.

EXAMPLE 145

Preparation of trans-4-(4-(trans-4-(3,5-difluoro-4-trifluoromethylphenyl)cyclohexyl)butyl)-1-n-pentyl-1-silacyclohexane 27.7 g (0.1 mol) of trans-4-(2-bromoethyl)-1-n-pentyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 37.1 g (0.1 mol) of 4-(trans-4-(2-bromoethyl)cyclohexyl)-2,6-difluoro-1-trifluorochloromethylbenzene. The resultant product was subjected to ordinary aftertreatments to obtain trans-4-(4-(trans-4-(3,5-difluoro-4-trifluoromethylphenyl)cyclohexyl)butyl)-1-n-pentyl-1-silacyclohexane, followed by isolation through chromatography to obtain 39.0 g (yield: 80%) of the intended trans isomer product.

EXAMPLE 146

Preparation of trans-4-(4-(trans-4-(4-(2,2-difluoroethoxy)phenyl)cyclohexyl)butyl)-1-n-pentyl-1-silacyclohexane 27.7 g (0.1 mol) of trans-4-(2-bromoethyl)-1-n-pentyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 34.7 g (0.1 mol) of 4-(trans-4-(2-bromoethyl)cyclohexyl)-1-(2,2-difluoroethoxy)benzene. The resultant product was subjected to ordinary aftertreatments to obtain trans-4-(4-(trans-4-(4-(2,2-difluoroethoxy)phenyl)cyclohexyl)butyl)-1-n-pentyl-1-silacyclohexane, followed by isolation through chromatography to obtain 33.9 g (yield: 73%) of the intended trans isomer product.

EXAMPLE 147

Preparation of trans-4-(4-(trans-4-(3,5-difluoro-4-difluoromethoxyphenyl)cyclohexyl)butyl)-1-n-pentyl-1-silacyclohexane 27.7 g (0.1 mol) of trans-4-(2-bromoethyl)-1-n-pentyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 36.9 g (0.1 mol) of 4-(trans-4-(2-bromoethyl)cyclohexyl)-2,6-difluoro-1-difluoromethoxybenzene. The resultant product was subjected to ordinary aftertreatments to obtain trans-4-(4-(trans-4-(3,5-difluoro-4-difluoromethoxyphenyl)cyclohexyl)butyl)-1-n-pentyl-1-silacyclohexane, followed by isolation through chromatography to obtain 44.2 g (yield: 91%) of the intended trans isomer product.

EXAMPLE 148

Preparation of trans-4-(4-(trans-4-(4-ethylphenyl)cyclohexyl)butyl)-1-n-propyl-1-silacyclohexane 29.5 g (0.1 mol) of 4-(trans-4-(2-bromoethyl)cyclohexyl)ethylbenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 24.9 g (0.1 mol) of trans-4-(2-bromoethyl)-1-n-propyl-1-silacyclohexane. The resultant product was subjected to ordinary aftertreatments to obtain trans-4-(4-(trans-4-(4-ethylphenyl)cyclohexyl)butyl)-1-n-propyl-1-silacyclohexane, followed by isolation through chromatography to obtain 31.4 g (yield: 82%) of the intended trans isomer product.

EXAMPLE 149

Preparation of trans-4-(4-(trans-4-(4-chloro-3,5-difluorophenyl)cyclohexyl)butyl)-1-n-propyl-1-silacyclohexane 33.8 g (0.1 mol) of 4-(trans-4-(2-bromoethyl)cyclohexyl)-2,6-difluoro-1-chlorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of dilithium tetrachlorocuprate and 32.5 g (0.1 mol) of trans-4-n-propyl-4-silacyclohexyl ethyltosylate. The resultant product was subjected to ordinary aftertreatments to obtain trans-4-(4-(trans-4-(4-chloro-3,5-difluorophenyl)cyclohexyl)butyl)-1-n-propyl-1-silacyclohexane, followed by isolation through chromatography to obtain 34.4 g (yield: 81%) of the intended trans isomer product.

EXAMPLE 150

Preparation of trans-4-(4-(trans-4-(4-(2,2-difluorovinyloxy)phenyl)cyclohexyl)butyl) -1-n-pentyl-1-silacyclohexane 34.5 g (0.1 mol) of 4-(trans-4-(2-bromoethyl)cyclohexyl)-1-(2,2-difluorovinyloxy)benzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 27.7 g (0.1 mol) of trans-4-(2-bromoethyl)-1-n-pentyl-1-silacyclohexane. The resultant product was subjected to ordinary aftertreatments to obtain trans-4-(4-(trans-4-(4-(2,2-difluorovinyloxy)phenyl)cyclohexyl)butyl)-1 -n-pentyl-1 -silacyclohexane, followed by isolation through chromatography to obtain 36.8 g (yield: 80%) of the intended trans isomer product.

EXAMPLE 151

Preparation of trans-4-(4-(trans-4-(4-(2,2-difluorovinyloxy)-3,5-difluorophenyl)cyclohexyl)butyl)-1-n-butyl-1-silacyclohexane 38.1 g (0.1 mol) of 4-(trans-4-(2-bromoethyl)cyclohexyl)-2,6-difluoro-1-(2,2-difluorovinyloxy)benzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 26.3 g (0.1 mol) of trans-4-(2-bromoethyl)-1-n-butyl-1-silacyclohexane. The resultant product was subjected to ordinary aftertreatments to obtain trans-4-(4-(trans-4-(4-(2,2-difluorovinyloxy)-3,5-difluorophenyl)cyclohexyl)butyl)-1-n-butyl-1-silacyclohexane, followed by isolation through chromatography to obtain 41.2 g (yield: 85%) of the intended trans isomer product.

EXAMPLE 152

Preparation of trans-4-(4-(trans-4-(4-(1,2-difluorovinyl)-2,6-difluorophenyl)cyclohexyl)butyl) -1 -n-butyl-1-silacyclohexane 36.5 g (0.1 mol) of 4-(trans-4-(2-bromoethyl)cyclohexyl)-2,6-difluoro-1-(1,2-difluorovinyl)benzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 26.3 g (0.1 mol) of trans-4-(2-bromoethyl)-1-n-butyl-1-silacyclohexane. The resultant product was subjected to ordinary aftertreatments to obtain trans-4-(4-(trans-4-(4-(1,2-difluorovinyl )-2,6- difluorophenyl ) cyclohexyl)butyl) -1 -n-butyl-1 -silacyclohexane, followed by isolation through chromatography to obtain 35.4 g (yield: 76%) of the intended trans isomer product.

EXAMPLE 153

Preparation of trans-4-(4-(trans-4-(4-(2,2,2-trifluoroethoxy)phenyl)cyclohexyl)butyl)-1-n-pentyl-1-silacyclohexane 29.1 g (0.1 mol) of trans-4-(3-bromopropyl)-1-n-pentyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 35.1 g (0.1 mol) of 4-(trans-4-bromomethylcyclohexyl)-1-(2,2,2-trifluoroethoxy)benzene. The resultant product was subjected to ordinary aftertreatments to obtain trans-4-(4-(trans-4-(4-(2,2,2-trifluoroethoxy)phenyl)cyclohexyl)butyl)-1-n-pentyl-1-silacyclohexane, followed by isolation through chromatography to obtain 38.0 g (yield: 79%) of the intended trans isomer product.

EXAMPLE 154

Preparation of trans-4-(4-(trans-4-(3-fluoro-4-chlorofluoromethylphenyl)cyclohexyl)butyl)-1-n-pentyl-1-silacyclohexane 29.1 g (0.1 mol) of trans-4-(3-bromopropyl)-1-n-pentyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 33.8 g (0.1 mol) of 4-(trans-4-5 bromomethylcyclohexyl)-2-fluoro-1-chlorofluoromethylbenzene. The resultant product was subjected to ordinary aftertreatments to obtain trans-4-(4-(trans-4-(3-fluoro-4-chlorofluoromethylphenyl)cyclohexyl)butyl)-1-n-pentyl-1-silacyclohexane, followed by isolation through chromatography to obtain 40.7 g (yield: 87%) of the intended trans isomer product.

EXAMPLE 155

Preparation of trans-4-(4-(trans-4-(3,5-difluoro-4-chlorodifluoromethylphenyl)cyclohexyl)butyl)-1-n-pentyl-1-silacyclohexane 29.1 g (0.1 mol) of trans-4-(3-bromopropyl)-1-n-pentyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 37.4 g (0.1 mol) of 4-(trans-4-bromomethylcyclohexyl)-2,6-difluoro-1-chorodifluoromethylbenzene. The resultant product was subjected to ordinary aftertreatments to obtain trans-4-(4-(trans-4-(3,5-difluoro-4-chlorodifluoromethylphenyl)cyclohexyl)butyl)-1-n-pentyl-1-silacyclohexane, followed by isolation through chromatography to obtain 38.7 g (yield: 77%) of the intended trans isomer product.

EXAMPLE 156

Preparation of trans-4-(4-(trans-4-(3-fluoro-4-(2,2-difluoroethoxy)phenyl)cyclohexyl)butyl)-1-n-propyl-1-silacyclohexane 29.1 g (0.1 mol) of trans-4-(3-bromopropyl)-1-n-propyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 35.1 g (0.1 mol) of 4-(trans-4-bromomethylcyclohexyl)-2-fluoro-1-(2,2-difluoroethoxy) benzene. The resultant product was subjected to ordinary aftertreatments to obtain trans-4-(4-(trans-4-(3-fluoro-4-(2,2-difluoroethoxy)phenyl)cyclohexyl)butyl)-1-n-propyl-1-silacyclohexane, followed by isolation through chromatography to obtain 37.1 g (yield: 82%) of the intended trans isomer product.

EXAMPLE 157

Preparation of trans-4-(4-(trans-4-(3,5-difluoro-4-(2,2,3,3-tetrafluoropropoxy)phenyl)cyclohexyl)butyl)-1-ethyl-1-silacyclohexane 29.1 g (0.1 mol) of trans-4-(3-bromopropyl)-1-ethyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 41.9 g (0.1 mol) of 4-(trans-4-bromomethylcyclohexyl)-2,6-difluoro-1-(2,2,3,3-tetrafluoropropoxy)benzene. The resultant product was subjected to ordinary aftertreatments to obtain trans-4-(4-(trans-4-(3,5-difluoro-4-(2,2,3,3-tetrafluoropropoxy)phenyl)cyclohexyl)butyl)-1-ethyl-1-silacyclohexane, followed by isolation through chromatography to obtain 42.6 g (yield: 84%) of the intended trans isomer product.

EXAMPLE 158

Preparation of trans-4-(4-(trans-4-(4-ethoxyphenyl)cyclohexyl)butyl)-1-n-pentyl-1-silacyclohexane 29.7 g (0.1 mol) of 4-(trans-4-bromomethylcyclohexyl)phenetole was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 29.1 g (0.1 mol) of trans-4-(3-bromopropyl)-1-n-pentyl-1-silacyclohexane. The resultant product was subjected to ordinary aftertreatments to obtain trans-4-(4-(trans-4-(4-ethoxyphenyl)cyclohexyl)butyl)-1-n-pentyl-1-silacyclohexane, followed by isolation through chromatography to obtain 33.2 g (yield: 78%) of the intended trans isomer product.

EXAMPLE 159

Preparation of trans-4-(4-(trans-4-(3,4,5-trifluorophenyl)cyclohexyl)butyl)-1-(3-methoxypropyl)-1-silacyclohexane 30.7 g (0.1 mol) of 1-(trans-4-bromomethylcyclohexyl)-3,4,5-trifluorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 29.3 g (0.1 mol) of trans-4-(3-bromopropyl)-1-(3-methoxypropyl)-1-silacyclohexane. The resultant product was subjected to ordinary aftertreatments to obtain trans-4-(4-(trans-4-(3,4,5-trifluorophenyl)cyclohexyl)butyl)-1-(3-methoxypropyl)-1-silacyclohexane, followed by isolation through chromatography to obtain 31.4 g (yield: 71%) of the intended trans isomer product.

EXAMPLE 160

Preparation of trans-4-(4-(trans-4-(4-(1,2-difluorovinyl)phenyl)cyclohexyl)butyl)-1-n-propyl-1-silacyclohexane 31.5 g (0.1 mol) of 4-(trans-4-bromomethylcyclohexyl)-1-(1,2-difluorovinyl)benzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 26.3 g (0.1 mol) of trans-4-(3-bromopropyl)-1-n-propyl-1-silacyclohexane. The resultant product was subjected to ordinary aftertreatments to obtain trans-4-(4-(trans-4-(4-(1,2-difluorovinyl)phenyl)cyclohexyl)butyl)-1-n-propyl-1-silacyclohexane, followed by isolation through chromatography to obtain 36.5 g (yield: 87%) of the intended trans isomer product.

EXAMPLE 161

Preparation of trans-4-(4-(trans-4-(2,3-difluoro-4-ethoxyphenyl)cyclohexyl)butyl)-1-n-propyl-1-silacyclohexane 33.3 g (0.1 mol) of 4-(trans-4-bromomethylcyclohexyl)-2,3-difluorophenetole was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 26.3 g (0.1 mol) of trans-4-(3-bromopropyl)-1-n-propyl-1-silacyclohexane. The resultant product was subjected to ordinary aftertreatments to obtain trans-4-(4-(trans-4-(2,3-difluoro-4-ethoxyphenyl)cyclohexyl)butyl)-1-n-propyl-1-silacyclohexane, followed by isolation through chromatography to obtain 37.6 g (yield: 86%) of the intended trans isomer product.

EXAMPLE 162

Preparation of trans-4-(4-(trans-4-(3,4-difluorophenyl)cyclohexyl)butyl)-1-(3-fluoropropyl)-1-silacyclohexane 28.9 g (0.1 mol) of 1-(trans-4-bromomethylcyclohexyl)-3,4-difluorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 28.1 g (0.1 mol) of trans-4-(3-bromopropyl)-1-(3-fluoropropyl)-1-silacyclohexane. The resultant product was subjected to ordinary aftertreatments to obtain trans-4-(4-(trans-4-(3,4-difluorophenyl)cyclohexyl)butyl)-1-(3-fluoropropyl)-1-silacyclohexane, followed by isolation through chromatography to obtain 33.7 g (yield: 82%) of the intended trans isomer product.

EXAMPLE 163

Preparation of trans-4-(4-(trans-4-(4-chlorodifluoromethoxyphenyl)cyclohexyl)butyl)-1-n-propyl-1-silacyclohexane 27.7 g (0.1 mol) of trans-4-(4-bromobutyl)-1-n-propyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 34.0 g (0.1 mol) of 4-(4-bromocyclohexyl)-1-difluorochloromethoxybenzene. The resultant product consisted of a mixture of trans and cis isomers with respect to the cyclohexane ring. The product was subjected to ordinary aftertreatments to obtain trans-4-(4-(trans-4-(4-chlorodifluoromethoxyphenyl)cyclohexyl)butyl)-1-n-propyl-1-silacyclohexane, followed by isolation through chromatography to obtain 17.9 g (yield: 39%) of the intended trans isomer product.

EXAMPLE 164

Preparation of trans-4-(4-(trans-4-(3-fluoro-4-trifluoromethoxyphenyl)cyclohexyl)butyl)-1-n-propyl-1-silacyclohexane 27.7 g (0.1 mol) of trans-4-(4-bromobutyl)-1-n-propyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 34.1 g (0.1 mol) of 4-(4-bromocyclohexyl)-2-fluoro-1-trifluoromethoxybenzene. The resultant product consisted of a mixture of trans and cis isomers with respect to the cyclohexane ring. The product was subjected to ordinary aftertreatments to obtain trans-4-(4-(trans-4-(3-fluoro-4-trifluoromethoxyphenyl)cyclohexyl)butyl)-1-n-propyl-1-silacyclohexane, followed by isolation through chromatography to obtain 20.4 g (yield: 45%) of the intended trans isomer product.

EXAMPLE 165

Preparation of trans-4-(4-(trans-4-(3,5-difluoro-4-(2, 2,3,3,3-pentafluoropropoxy)phenyl)cyclohexyl) butyl)-1-n-propyl-1-silacyclohexane 27.7 g (0.1 mol) of trans-4-(4-bromobutyl)-1-n-propyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 42.3 g (0.1 mol) of 4-(4-bromocyclohexyl)-2,6-difluoro-1-(2,2,3,3,3-pentafluoropropoxy)benzene. The resultant product consisted of a mixture of trans and cis isomers with respect to the cyclohexane ring. The product was subjected to ordinary aftertreatments to obtain trans-4-(4-(trans-4-(3,5-difluoro-4-(2,2,3,3,3-pentafluoropropoxy)phenyl)cyclohexyl)butyl)-1-n-propyl-1-silacyclohexane, followed by isolation through chromatography to obtain 19.0 g (yield: 35%) of the intended trans isomer product.

EXAMPLE 166

Preparation of trans-4-(4-(trans-4-(3-fluoro-4-(2,2,2-trifluoroethoxy)phenyl)cyclohexyl)butyl)-1-n-pentyl-1-silacyclohexane 30.5 g (0.1 mol) of trans-4-(4-bromobutyl)-1-n-pentyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 35.5 g (0.1 mol) of 4-(4-bromocyclohexyl)-2-fluoro-1-(2,2,2-5 trifluoroethoxy) benzene. The resultant product consisted of a mixture of trans and cis isomers with respect to the cyclohexane ring. The product was subjected to ordinary aftertreatments to obtain trans-4-(4-(trans-4-(3-fluoro-4-(2,2,2-trifluoroethoxy)phenyl)cyclohexyl)butyl)-1-n-pentyl-1-silacyclohexane, followed by isolation through chromatography to obtain 19.4 g (yield: 40%) of the intended trans isomer product.

EXAMPLE 167

Preparation of trans-4-(4-(trans-4-(3-fluoro-4-difluoromethoxyphenyl)-1-silacylohexyl)butyl)-1-n-pentylcyclohexane 28.9 g (0.1 mol) of trans-4-(4-bromobutyl)-1-n-pentylcyclohexane was dropped in a mixture of 2.5 g (0.11 mols) of magnesium and 300 ml of THF to obtain a Grignard reagent. The resultant solution was then dropped in a solution, in 500 ml of THF, of 29.5 g (0.1 mol) of 4-(trans-4-chloro-4-silacyclohexyl)-2-fluoro-1-difluoromethoxybenzene. The resultant product consisted of a mixture of trans and cis isomers with respect to the cyclohexane ring. The product was subjected to ordinary aftertreatments to obtain trans-4-(4-(trans-4-(3-fluoro-4-difluoromethoxyphenyl)-1-silacyclohexyl)butyl)-1-n-pentylcyclohexane, followed by isolation through chromatography to obtain 41.8 g (yield: 89%) of the intended trans isomer product.

EXAMPLE 168

Preparation of trans-4-(4-(trans-4-(3,4-difluorophenyl)cyclohexyl)butyl)-1-n-pentyl-4-methyl-4-silacyclohexane 34.1 g (0.1 mol) of 4-(4-bromocyclohexyl)-1,2-difluorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of Copper (I) iodide and 31.9 g (0.1 mol) of 4-(4-bromobutyl)-1-n-pentyl-4-methyl-4-silacyclohexane. The resultant product consisted of a mixture of trans and cis isomers with respect to the cyclohexane ring. The product was subjected to ordinary aftertreatments to obtain trans-4-(4-(trans-4-(3,4-difluorophenyl)cyclohexyl)butyl)-1-n-pentyl-4-methyl-4-silacyclohexane, followed by isolation through chromatography to obtain 16.7 g (yield: 38%) of the intended trans isomer product.

EXAMPLE 169

Preparation of trans-4-(4-(trans-4-(2,3-difluoro-4-ethoxyphenyl)-1-silacyclohexyl)butyl)-1- n-pentyl cyclohexane 31.9 g (0.1 mol) of 4-(4-bromocyclohexyl)-2,3-difluorophentole was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 30.5 g (0.1 mol) of trans-4-(4-bromobutyl)-1-n-pentyl-1-silacyclohexane. The resultant product consisted of a mixture of trans and cis isomers with respect to the cyclohexane ring. The product was subjected to ordinary aftertreatments to obtain trans-4-(4-(trans-4-(2, 3-difluoro-4-ethoxyphenyl)-1-silacyclohexyl)butyl)-1-n-pentylcyclohexane, followed by isolation through chromatography to obtain 18.0 g (yield: 39%) of the intended trans isomer product.

EXAMPLE 170

Preparation of trans-4-(4-(trans-4-(3-fluoro-4-(1,2-difluorovinyl)phenyl)cyclohexyl)butyl)-1-n-propylcyclohexane 31.9 g (0.1 mol) of 4-(4-bromocyclohexyl)-2-fluoro-1-(1, 2-difluorovinyl)benzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 27.7 g (0.1 mol) of trans-4-(4-bromobutyl)-1-n-propyl-1-silacyclohexane. The resultant product consisted of a mixture of tram and cis isomers with respect to the cyclohexane ring. The product was subjected to ordinary aftertreatments to obtain trans-4-(4-(trans-4-(3-fluoro-4-(1,2-difluorovinyl)phenyl)cyclohexyl)butyl)-1-n-propylcyclohexane, followed by isolation through chromatography to obtain 16.6 g (yield: 38%) of the intended trans isomer product.

EXAMPLE 171

Preparation of trans-4-(4-(trans-4-(2,3-difluoro-4-ethylphenyl)cyclohexyl)butyl)-1-n-pentyl-1-silacyclohexane 30.3 g (0.1 mol) of 4-(4-bromocyclohexyl)-2,3-difluoro-1-ethylbenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 30.5 g (0.1 mol) of trans-4-(4-bromobutyl)-1-n-pentyl-1-silacyclohexane. The resultant product consisted of a mixture of trans and cis isomers with respect to the cyclohexane ring. The product was subjected to ordinary aftertreatments to obtain trans-4-(4-(trans-4-(2,3-difluoro-4-ethylphenyl)cyclohexyl)butyl)-1-n-pentyl-1-silacyclohexane, followed by isolation through chromatography to obtain 16.9 g (yield: 38%) of the intended trans isomer product.

EXAMPLE 172

Preparation of trans-4-(4-(trans-4-(1,2,2-trifluorovinyloxy)phenyl)cyclohexyl)butyl)-1-n-butyl-1-silacyclohexane 33.5 g (0.1 mol) of 4-(4-bromocyclohexyl)-1-(1,2,2-trifluorovinyloxy)benzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 29.1 g (0.1 mol) of trans-4-(4-bromobutyl)-1-n-butyl-1-silacyclohexane. The resultant product consisted of a mixture of tram and cis isomers with respect to the cyclohexane ring. The product was subjected to ordinary aftertreatments to obtain trans-4-(4-(trans-4-(1,2,2-trifluorovinyloxy)phenyl)cyclohexyl)butyl)-1-n-butyl-1-silacyclohexane, followed by isolation through chromatography to obtain 17.1 g (yield: 37%) of the intended trans isomer product.

EXAMPLE 173

Preparation of trans-4-(4-(trans-4-(4-chlorofluoromethoxyphenyl)cyclohexyl)butyl)-1-n-propyl-1-silacyclohexane 36.0 g (0.1 tool) of trans-4-(4-(4-bromocyclohexyl)butyl)-1-n-propyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of tetrakistriphenylphosphine palladium and 24.0 g (0.1 mol) of 1-bromo-4-chlorofluoromethoxybenzene. The resultant product consisted of a mixture of trans and cis isomers with respect to the cyclohexane ring. The product was subjected to ordinary aftertreatments and isolated through chromatography to obtain 15.2 g (yield: 35%) of trans-4-(4-(trans-4-(4-chlorofluoromethoxyphenyl)cyclohexyl)butyl)-1-n-propyl-1-silacyclohexane.

EXAMPLE 174

Preparation of trans-4-(4-(trans-4-(3-fluoro-4-chlorodifluoromethoxyphenyl)cyclohexyl)butyl)-1-n-propyl-1-silacyclohexane 36.0 g (0.1 mol) of trans-4-(4-(4-bromocyclohexyl)butyl)-1-n-propyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of tetrakistriphenylphosphine palladium and 27.6 g (0.1 mol) of 1-bromo-4-chlorodifluoromethoxy-3-fluorobenzene. The resultant product consisted of a mixture of trans and cis isomers with respect to the cyclohexane ring. The product was subjected to ordinary aftertreatments and isolated through chromatography to obtain 11.9 g (yield: 25%) of trans-4-(4-(trans-4-(3-fluoro -4-chloro difluoromethoxyphenyl)cyclohexyl)butyl)-1-n-propyl-1-silacyclohexane.

EXAMPLE 175

Preparation of trans-4-(4-(trans-4-(3-fluoro-4-(3,3,3-trifluoropropoxy)phenyl)cyclohexyl)butyl)-1-n-propyl-1-silacyclohexane 36.0 g (0.1 mol) of trans-4-(4-(4-bromocyclohexyl)butyl)-1-n-propyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of tetrakistriphenylphosphine palladium and 28.7 g (0.1 mol) of 1-bromo-4-(3,3,3-trifluoropropoxy)-3-fluorobenzene. The resultant product consisted of a mixture of trans and cis isomers with respect to the cyclohexane ring. After ordinary aftertreatments, the product was subjected to isolation through chromatography to obtain 15.3 g (yield: 32%) of trans-4-(4-(trans-4-(3-fluoro-4-(3,3,3-trifluoropropoxy) phenyl)cyclohexyl)butyl)-1-n-propyl-1 -silacyclohexane.

EXAMPLE 176

Preparation of trans-4-(4-(trans-4-(3-fluoro-4-(3-chloropropoxy)phenyl)cyclohexyl)butyl)-1-n-propyl-1-silacyclohexane 36.0 g (0.1 mol) of trans-4-(4-(4-bromocyclohexyl)butyl)-1-n-propyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of tetrakistriphenylphosphine palladium and 26.8 g (0.1 mol) of 1-bromo-4-(3-chloropropoxy)-3-fluorobenzene. The resultant product consisted of a mixture of trans and cis isomers with respect to the cyclohexane ring. After ordinary treatments, the product was subjected to isolation through chromatography to obtain 14.7 g (yield: 32%) of trans-4-(4-(trans-4-(3-fluoro -4-(chloropropoxy)phenyl)cyclohexyl)butyl)-1-n-propyl-1-silacyclohexane.

EXAMPLE 177

Preparation of trans-4-(4-(trans-4-(4-trifluoromethoxyphenyl)cyclohexyl)butyl)-1-ethyl-1-silacyclohexane 34.5 g (0.1 mol) of trans-4-(4-(4-bromocyclohexyl)butyl)-1-ethyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of tetrakistriphenylphosphine palladium and 24.1 g (0.1 mol) of 1-bromo-4-trifluoromethoxybenzene. The resultant product consisted of a mixture of trans and cis isomers with respect to the cyclohexane ring. After ordinary treatments, the product was subjected to isolation through chromatography to obtain 13.4 g (yield: 31%) of trans-4-(4-(trans-4-(4- trifluoromethoxyphenyl)cyclohexyl)butyl)-1- ethyl-1-silacyclohexane.

EXAMPLE 178

Preparation of trans-4-(4-(trans-4-(4-chloro-3-fluorophenyl)cyclohexyl)butyl)-1-n-propyl-1-silacyclohexane 20.9 g (0.1 mol) of 1-bromo-3-fluoro-4-chlorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 36.0 g (0.1 mol) of trans-4-(4-(4-bromocyclohexyl)butyl)-1-n-propyl-1-silacyclohexane. The resultant product consisted of a mixture of trans and cis isomers with respect to the cyclohexane ring. After ordinary treatments, the product was subjected to isolation through chromatography to obtain 13.2 g (yield: 32%) of trans-4-(4-(trans-4-(4-chloro-3-fluorophenyl)cyclohexyl)butyl)-1-n-propyl-1-silacyclohexane.

EXAMPLE 179

Preparation of trans-4-(4-(trans-4-(2,3-difluoro-4-n-propylphenyl)cyclohexyl)butyl)-1-n-propyl-1-silacyclohexane 23.5 g (0.1 mob of 1-bromo-2,3-difluoro-4-propylbenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 36.0 g (0.1 mol) of trans-4-(4-(4-bromocyclohexyl)butyl)-1-n-propyl-1-silacyclohexane. The resultant product consisted of a mixture of trans and cis isomers with respect to the cyclohexane ring. After ordinary treatments, the product was subjected to isolation through chromatography to obtain 14.9 g (yield: 34%) of trans-4-(4-(trans-4-(2,3-difluoro-4-n-propylphenyl)cyclohexyl)butyl)-1-n-propyl-1-silacyclohexane.

EXAMPLE 180

Preparation of trans-4-(4-(trans-4-(4-(1,2,2-trifluorovinyl)-3,5-difluorophenyl)cyclohexyl)butyl)-1-n-pentyl-1-silacyclohexane 27.3 g (0.1 mol) of 1-bromo-3,5-difluoro-4-(1,2,2-trifluorovinyl)benzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 38.8 g (0.1 mol) of trans-4-(4-(4-bromocyclohexyl)butyl)-1-n-pentyl-1-silacyclohexane. The resultant product consisted of a mixture of trans and cis isomers with respect to the cyclohexane ring. After ordinary treatments, the product was subjected to isolation through chromatography to obtain 19.1 g (yield: 38%) of trans-4-(4-(trans-4-(4-(1,2,2-trifluorovinyl)-3,5-difluorophenyl)cyclohexyl)butyl)-1-n-pentyl-1-silacyclohexane.

EXAMPLE 181

Preparation of trans-4-(4-(trans-4-(3,4-difluorophenyl)cyclohexyl)butyl)-1-n-pentyl-1-silacyclohexane 19.3 g (0.1 mol) of 1-bromo-3,4-difluorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 38.8 g (0.1 mol) of trans-4-(4-(4-bromocyclohexyl)butyl)-1-n-pentyl-1-silacyclohexane. The resultant product consisted of a mixture of trans and cis isomers with respect to the cyclohexane ring. After ordinary treatments, the product was subjected to isolation through chromatography to obtain 13.8 g (yield: 33%) of trans-4-(4-(trans-4-(3,4-difluorophenyl)cyclohexyl)butyl)-1-n-pentyl-1-silacyclohexane. Crystal-nematic phase transition temperature: 28° C. Nematic phase-isotropic phase transition temperature: 52° C. IR (liquid film) spectra, $v_{max}$: 2922, 2850, 2098, 1608, 1518, 1290, 1209, 1115, 976, 887, 816 cm$^{-1}$

EXAMPLE 182

Preparation of trans-4-(4-(trans-4- (3,4,5-trifluorophenyl)-1 -5 silacyclohexyl)butyl)-1-n-pentyl-1-silacyclohexane 21.1 g (0.1 mol) of 1-bromo-3,4,5-trifluorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 40.4 g (0.1 mol) of trans-4-(4-(4-bromo-1-silacyclohexyl)butyl)-1-n-pentyl-1-silacyclohexane. The resultant product consisted of a mixture of trans and cis isomers with respect to the cyclohexane ring. After ordinary treatments, the product was subjected to isolation through chromatography to obtain 13.1 g (yield: 29%) of trans-4-(4-(trans-4-(3,4,5-trifluorophenyl)-1-silacyclohexyl)butyl)-1-n-pentyl-1-silacyclohexane.

EXAMPLE 183

Preparation of trans-4-(4-(3,5-difluoro-4-difluoromethoxyphenyl)butyl)-1-propyl-1-silacyclohexane 50 ml (0.13 mols) of a THF solution of 2.5M of propylmagnesium bromide was dropped in a mixed solution of 44.5 g (0.1 mol) of 1-chloro-1-phenyl-4-(4-(3,5-difluoro-4-difluoromethoxyphenyl)butyl)-1-silacyclohexane and 300 ml of THF. After ordinary after-treatments, 4-(4-(3,5-difluoro-4-difluoromethoxyphenyl)butyl)-1-phenyl-1-propyl-1-silacyclohexane was obtained.

300 ml of a carbon tetrachloride solution of 1.0 mole of iodine monochloride was added to the product at room temperature, followed by agitation for 30 minutes and concentration. The resultant residue was dissolved in 200 ml of tetrahydrofuran and dropped in a mixture of 4.0 g of lithium aluminium hydride and 50 ml of tetrahydrofuran at 0° C. The reaction mixture was agitated for 1 hour, after which it was poured into 200 ml of 5% hydrochloric acid, followed by extraction with ethyl acetate. The resultant extract was subjected to ordinary washing with brine, drying and concentration, followed by purification through silica gel chromatography to obtain 30.5 g (yield: 81%) of the captioned product.

EXAMPLE 184

Preparation of trans-4-(trans-4-(4-(3,5-difluoro-4-trifluoromethoxyphenyl)butyl)cyclohexyl)-1-pentyl-1-silacyclohexane 40.5 g (0.1 mol) of trans-4-(4-bromocyclohexyl)-1-pentyl-1-phenyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 38 g (0.1 mol) of 4-(4-iodobutyl)-2,6-difluoro-1-trifluoromethoxybenzene, followed by ordinary after-treatments to obtain 4-(trans-4-(4-(3,5-difluoro-4-trifluoromethoxyphenyl)butyl)cyclohexyl)-1-pentyl-1-phenyl-1-silacyclohexane.

300 ml of a carbon tetrachloride solution of 1.0 mole of iodine monochloride was added to the product at room temperature, followed by agitation for 30 minutes and concentration. The resultant residue was dissolved in 200 ml of tetrahydrofuran and dropped in a mixture of 4.0 g of lithium aluminium hydride and 50 ml of tetrahydrofuran at 0° C. The reaction mixture was agitated for 1 hour, after which it was poured into 200 ml of 5% hydrochloric acid, followed by extraction with ethyl acetate. The resultant extract was subjected to ordinary washing with brine, drying and concentration, followed by purification through silica gel chromatography to obtain 30.5 g (yield: 81%) of the captioned compound.

EXAMPLE 185

Preparation of trans-4-(trans-4-(4-(3,4,5-trifluorophenyl)butyl)cyclohexyl)-1-pentyl-1-silacyclohexane 26.7 g (0.1 tool) of 5-(4-bromobutyl)-1,2,3-trifluorobenzene was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 33.1 g (0.1 mol) of trans-4-(4-bromocylohexyl)-1-pentyl-1-phenyl-1-silacyclohexane. After ordinary aftertreatments, 4-(trans-4-(4-(3,4,5-trifluorophenyl)butyl)cyclohexyl)-1-pentyl-4-phenyl-1-silacyclohexane was obtained.

300 ml of a carbon tetrachloride solution of 1.0 mole of iodine monochloride was added to the product at room temperature, followed by agitation for 30 minutes and concentration. The resultant residue was dissolved in 200 ml of tetrahydrofuran and dropped in a mixture of 4.0 g of lithium aluminium hydride and 50 ml of tetrahydrofuran at 0° C. The reaction mixture was agitated for I hour, after which it was poured into 200 ml of 5% hydrochloric acid, followed by extraction with ethyl acetate. The resultant extract was subjected to ordinary washing with brine, drying and concentration, followed by purification through silica gel chromatography to obtain 19.1 g (yield: 44.2%) of the captioned compound.

EXAMPLE 186

Preparation of trans-4-(trans-4-(4-(4-ethoxy-2,3-difluorophenyl)butyl)cyclohexyl)-1-butyl-1-silacyclohexane 27.9 g (0.1 mol) of 4-(3-bromopropyl)-2,3-difluorophenetole was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 40.5 g (0.1 mol) of trans-4-(trans-4-bromomethylcyclohexyl)-1-butyl-1-phenyl-1-silacyclohexane. After ordinary aftertreatments, 4-(trans-4-(4-(4-ethoxy-2,3-difluorophenyl)butyl)cyclohexyl)-2-butyl-1-phenyl-1-silacyclohexane was obtained. 300 ml of a carbon tetrachloride solution of 1.0 mole of iodine monochloride was added to the product at room temperature, followed by agitation for 30 minutes and concentration. The resultant residue was dissolved in 200 ml of tetrahydrofuran and dropped in a mixture of 4.0 g of lithium aluminium hydride and 50 ml of tetrahydrofuran at 0° C. The reaction mixture was agitated for 1 hour, after which it was poured into 200 ml of 5% hydrochloric acid, followed by extraction with ethyl acetate. The resultant extract was subjected to ordinary washing with brine, drying and concentration, followed by purification through silica gel chromatography to obtain 34.5 g (yield: 76.8%) of the captioned compound.

EXAMPLE 187

Preparation of trans-4-(trans-4-(4-(3-fluoro-4-trifluoromethoxyphenyl)butyl)cyclohexyl)-1-propyl-1-silacyclohexane 42.0 g (0.1 mol) of trans-4-(trans-4-(3-bromopropyl)cyclohexyl)-1-propyl-1-phenyl-1-silacyclohexane was dropped in a mixture of 2.5 g (0.11 mols) of magnesium and 300 ml of THF to obtain a Grignard reagent. The resultant solution was further dropped in a solution, in 500 ml of THF, of 0.5 g of triethyl phosphate, 0.1 g of copper (I) iodide and 27.3 g (0.1 mol) of 4-bromomethyl-2-fluoro-1-trichloromethoxybenzene. After ordinary aftertreatments, 4-(trans-4-(4-(3-fluoro-4-trifluoromethoxyphenyl)-butyl) cyclohexyl)-1-propyl-1-phenyl-1-silacyclohexane was obtained.

300 ml of a carbon tetrachloride solution of 1.0 mole of iodine monochloride was added to the product at room temperature, followed by agitation for 30 minutes and concentration. The resultant residue was dissolved in 200 ml of tetrahydrofuran and dropped in a mixture of 4.0 g of lithium aluminium hydride and 50 ml of tetrahydrofuran at 0° C. The reaction mixture was agitated for 1 hour, after which it was poured into 200 ml of 5% hydrochloric acid, followed by extraction with ethyl acetate. The resultant extract was subjected to ordinary washing with brine, drying and concentration, followed by purification through silica gel chromatography to obtain 39.5 g (yield: 86%) of the captioned compound.

EXAMPLE 188

Preparation of trans-4-(4-(trans-4-(3,5-difluoro-4-difluoromethoxyphenyl)cyclohexyl)butyl)-1-n-pentyl-1-silacyclohexane 35.1 g (0.1 mol) of trans-4-(2-bromoethyl)-1-n-pentyl-1-phenyl-1-silacyclohexane was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 36.9 g (0.1 mol) of 4-(trans-4-(2-bromoethyl)cyclohexyl)-2,6-difluoro-1-difluoromethoxybenzene. After ordinary after-treatments, there was obtained 4-(4-(trans-4-(3,5-difluoro-4-difluoromethoxyphenyl)cyclohexyl)butyl)-1-n-pentyl-1-phenyl-1-silacyclohexane 300 ml of a carbon tetrachloride solution of 1.0 mole of iodine monochloride was added to the product at room temperature, followed by agitation for 30 minutes and concentration. The resultant residue was dissolved in 200 ml of tetrahydrofuran and dropped in a mixture of 4.0 g of lithium aluminium hydride and 50 ml of tetrahydrofuran at 0° C. The reaction mixture was agitated for 1 hour, after which it was poured into 200 ml of 5% hydrochloric acid, followed by extraction with ethyl acetate. The resultant extract was subjected to ordinary washing with brine, drying and concentration, followed by purification through silica gel chromatography to obtain 43.8 g (yield: 90%) of the captioned compound.

EXAMPLE 189

Preparation of trans-4-(4-(trans-4-(3,4,5-trifluorophenyl)cyclohexyl)butyl)-1-propyl-1-silacyclohexane 30.7 g (0.1 mol) of 1-(trans-4-bromomethylcyclohexyl)-3,4,5-trifluorobenzene was dropped in a mixture of 2.5 g (0.11 mols) of magnesium and 300 ml of THF to obtain a Grignard reagent. The resultant solution was then dropped in a solution, in 500 ml of THF, of 0.5 g of triethyl phosphate, 0.1 g of copper (I) iodide and 38.1 g (0.1 mol) of trans-4-(3-bromopropyl)-1-propyl-1-tolyl-1-silacyclohexane. After ordinary after-treatments, there was obtained 4-(4-(trans-4-(3,4,5-trifluorophenyl)cyclohexyl)butyl-1-propyl-1-tolyl-1-silacyclohexane 300 ml of a carbon tetrachloride solution of 1.0 mole of iodine monochloride was added to the product at room temperature, followed by agitation for 30 minutes and concentration. The resultant residue was dissolved in 200 ml of tetrahydrofuran and dropped in a mixture of 4.0 g of lithium aluminium hydride and 50 ml of tetrahydrofuran at 0° C. The reaction mixture was agitated for 1 hour, after which it was poured into 200 ml of 5% hydrochloric acid, followed by extraction with ethyl acetate. The resultant extract was subjected to ordinary washing with brine, drying and concentration, followed by purification through silica gel chromatography to obtain 30.6 g (yield: 69.2%) of the captioned compound.

What is claimed is:

1. A silacyclohexane compound selected from the group consisting of compounds of the following formulas (I) and (II)

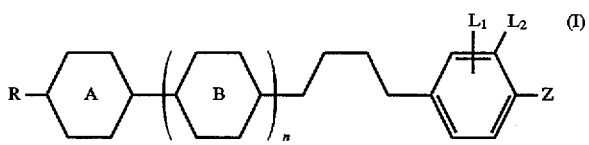

wherein R represents a linear alkyl group having from 1 to 10 carbon atoms, a mono or difluoroalkyl group having from 1 to 10 carbon atoms, a branched alkyl group having from 3 to 8 carbon atoms, an alkoxyalkyl group having from 2 to 7 carbon atoms, or an alkenyl group having from 2 to 8 carbon atoms; one of

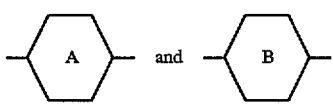

represents a trans-1-sila-1,4-cyclohexylene group or trans-4-sila-1,4-cyclohexylene group in which the silicon atom at the 1 or 4 position has a substituent of H, F, Cl or $CH_3$, and the other represents a trans-1,4-cyclohexylene group, or such a trans-1-sila-1,4-cyclohexylene group or trans-4-sila-1,4-cyclohexylene group as defined above, n is 0 or 1, $L_1$ represents H or F, $L_2$ represents H, F or Cl, and Z represents CN, F, Cl, $CF_3$, $CClF_2$, $CHClF$, $OCF_3$, $OClCF_2$, $OCHF_2$, $OCHClF$, $(O)_mCY=CX_1X_2$ wherein m is 0 or 1, Y and $X_1$ independently represent H, F or Cl, $X_2$ represents F or Cl, $O(CH_2)_r(CF_2)_sX_3$ wherein r and s are respectively, 0, 1 or 2 provided that r+s is 2, 3 or 4, and $X_3$ represents H, F or Cl, or R or OR wherein R is as defined above, and

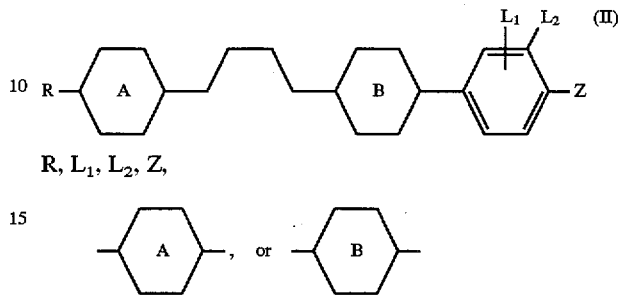

are, respectively, as defined in the formula (I).

2. A silacyclohexane compound according to claim 1, wherein said silacyclohexane compound is of the formula (I).

3. A silacyclohexane compound according to claim 2, wherein said silacyclohexane compound is of the following formula (Ia)

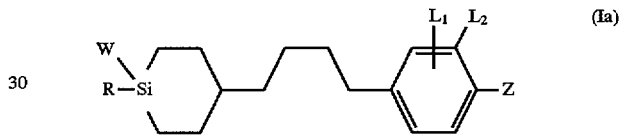

wherein W is H, F, Cl or $CH_3$.

4. A silacyclohexane compound according to claim 2, wherein said silacyclohexane compound is of the following formula (Ic)

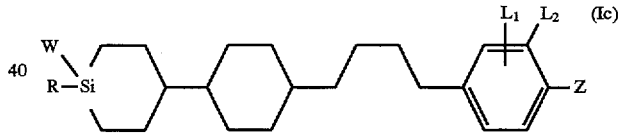

wherein W is H, F, Cl or $CH_3$.

5. A silacyclohexane compound according to claim 2, wherein said silacyclohexane compound is of the following formula (Ie)

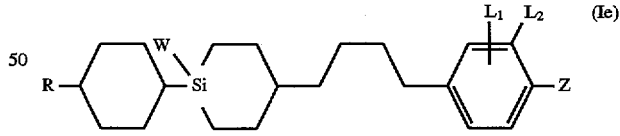

wherein W is H, F, Cl or $CH_3$.

6. A silacyclohexane compound according to claim 2, wherein said silacyclohexane compound is of the following formula (Ig)

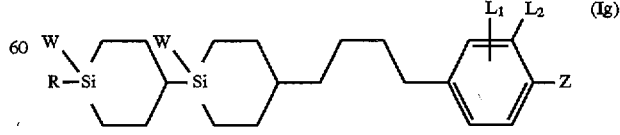

wherein W is H, F, Cl or $CH_3$.

7. A silacyclohexane compound according to claim 1, wherein said silacyclohexane compound is of the formula (II).

8. A silacyclohexane compound according to claim 7, wherein said silacyclohexane compound is of the following general formula (IIa)

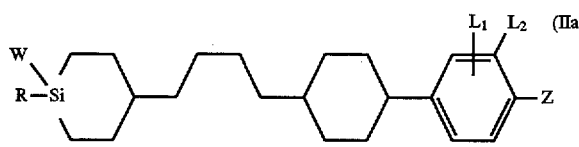

wherein W is H, F, Cl or $CH_3$.

9. A silacyclohexane compound according to claim 7, wherein said silacyclohexane compound is of the following general formula (IIa)

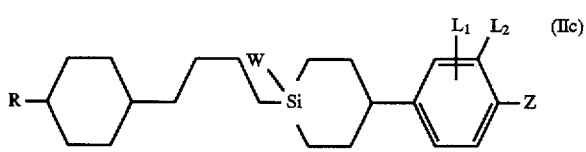

wherein W is H, F, Cl or $CH_3$.

10. A silacyclohexane compound according to claim 7, wherein said silacyclohexane compound is of fie following general formula (IIe)

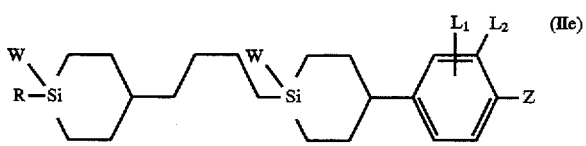

wherein W is H, F, Cl or $CH_3$.

11. A silacyclohexane compound of selected from the group consisting of compounds of the following formulas (III) and (IV)

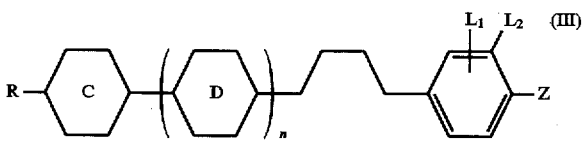

wherein R represents a linear alkyl group having from 1 to 10 carbon atoms, a mono or difluoroalkyl group having from 1 to 10 carbon atoms, a branched alkyl group having from 3 to 8 carbon atoms, an alkoxyalkyl group having from 2 to 7 carbon atoms, or an alkenyl group having from 2 to 8 carbon atoms; n is 0 or 1, $L_1$ represents H or F, $L_2$ represents H, F or Cl and Z represents CN, F, Cl, $CF_3$, $CClF_2$, $CHClF$, $OCF_3OCClF_2$, $OCHF_2$, $OCHClF$, $(O)_mCY=CX_1X_2$ wherein m is 0 or 1, Y and $X_1$ independently represent H, F or Cl, $X_2$ represents F or Cl, $O(CH_2)_r(CF_2)_sX_3$ wherein r and s are respectively, 0, 1 or 2 provided that r+s is 2, 3 or 4, and $X_3$ represents H, F, Cl, R or OR wherein R is as defined above; and one of

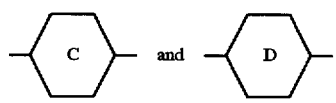

represents a trans-1-sila-1,4-cyclohexylene group or trans-4-sila-1,4-cyclohexylene group in which the silicon atom at the 1 or 4 position has a substituent of phenyl or tolyl, and the other represents a trans-1,4-cyclohexylene group, or such a trans-1-sila-1,4-cyclohexylene group or trans-4-sila-1,4-cyclohexylene group as having phenyl or tolyl, and

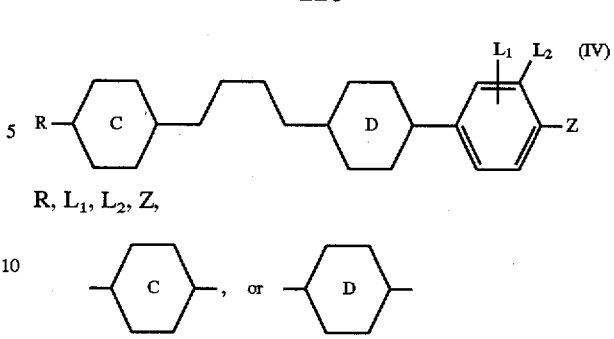

R, $L_1$, $L_2$, Z, are, respectively, as defined above.

12. A silacyclohexane compound according to claim 11, wherein said compound is of the formula (III).

13. A silacyclohexane compound according to claim 11, wherein said compound is of the formula (IV).

14. A process for preparing a silacyclohexane compound of the following general formula (I)

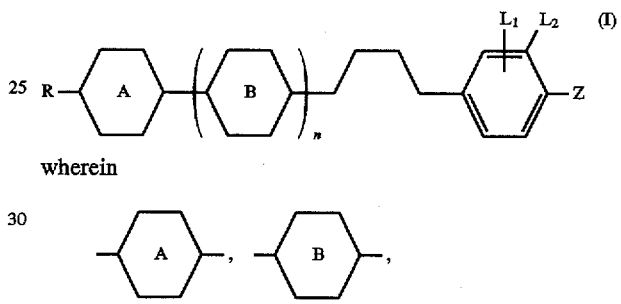

wherein

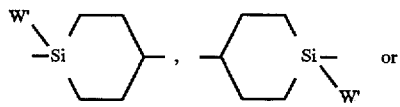

R, $L_1$, $L_2$, Z and n are, respectively, as defined in claim 1, the process comprising:

reacting an organometallic compound of the general formula, R-M, wherein R is as defined in the formula (I) and M represents Li, MgP or ZnP wherein P is a halogen atom, with a compound of the following general formula (1)

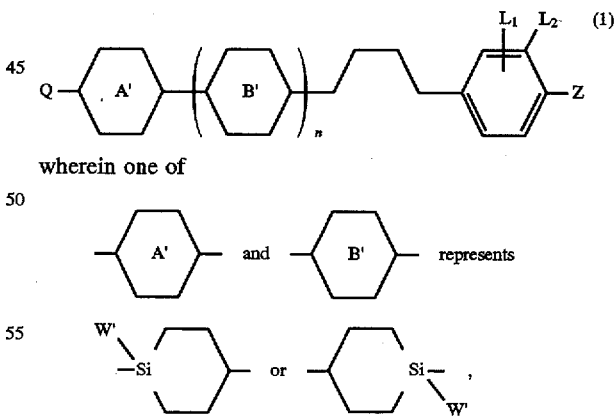

wherein one of in which W' represents H, methyl, phenyl or tolyl, and, if present, the other represents

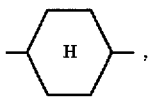

$L_1$, $L_2$ and n are, respectively, as defined in the formula (I), and Q represents a halogen atom, an alkoxy group, a methanesulfonyloxy group, a benzenesulfonyloxy group, a p-toluenesulfonyloxy group or a trifluoromethanesulfonyloxy group, whereby R in the organometallic compound is bonded to the carbon or silicon atom of the compound of the formula (1) to obtain the compound of the general formula (I) provided that when W' is phenyl or tolyl, the phenyl or tolyl is further converted to Cl, F, H or methyl.

15. A process for preparing a silacyclohexane compound of the following general formula (I)

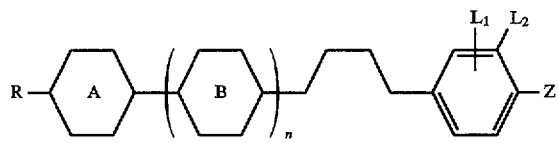

the process comprising:

reacting an organometallic compound of the following formula

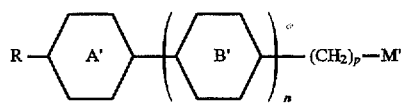

wherein

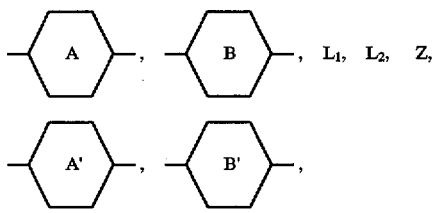

R and n are, respectively, as defined in claim 14, and M' represents MgP or ZnP, in which P represents a halogen, or B(OY$_1$)$_2$ in which Y$_1$ represents H or an alkyl group having from 1 to 6 carbon atoms, with a compound of the following general formula (3)

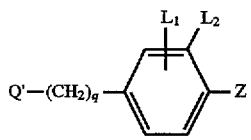

wherein $L_1$, $L_2$ and Z are, respectively, as defined with respect to the formula (I), Q' represents a halogen atom, a methanesulfonyloxy group, a benzenesulfonyloxy group, a p-toluenesulfonyloxy group or a trifluoromethanesulfonyloxy group, p in the formula (2) and q are, respectively, a value of 0, 1, 2, 3 or 4 provided that (p+q) is 4, provided that when W' is phenyl or tolyl, the phenyl or tolyl is further converted to Cl, F, H or methyl.

16. A process for preparing a silacyclohexane compound of the following general formula (I)

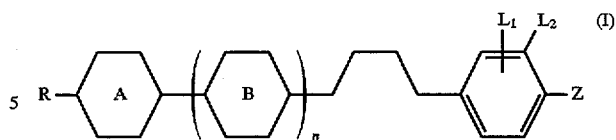

the process comprising:

reacting an organometallic compound of the following formula (4)

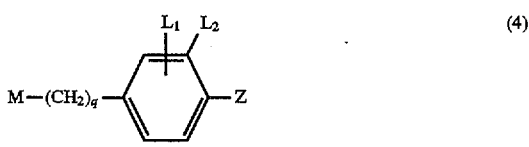

with a compound of the following general formula (5)

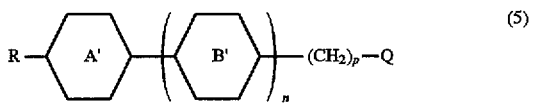

wherein

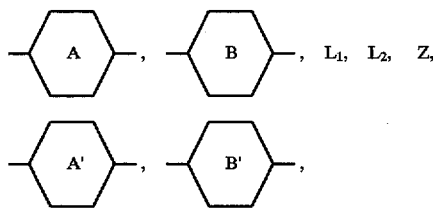

R and n are, respectively, as defined in claim 14, M represents Li, MgP or ZnP, wherein P is halogen and Q represents a halogen atom, an alkoxy group, a methanesulfonyloxy group, a benzenesulfonyloxy group, a p-toluenesulfonyloxy group or a trifluoromethanesulfonyloxy group, and p and q are, respectively, a value of 0, 1, 2, 3, or 4 provided that (p+q) is 4, provided that when W' is phenyl or tolyl, the phenyl or tolyl is further converted to Cl, F, H or methyl.

17. A process for preparing a silacyclohexane compound of the following general formula (I)

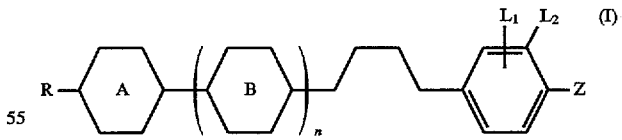

the process comprising:

reacting an organometallic compound of the following general formula (6)

with a compound of the following general formula (7)

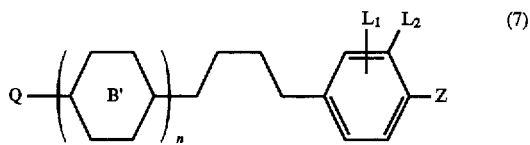

wherein

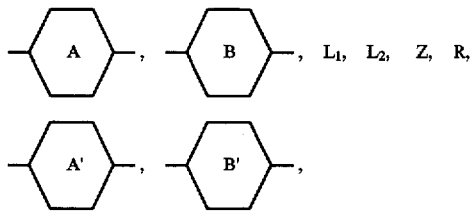

$L_1$, $L_2$, Z and n are, respectively, as defined in claim 14, and M represents Li, MgP or ZnP wherein P is halogen, Q represents a halogen atom, an alkoxy group having from 1 to 4 carbon atoms, a methanesulfonyloxy group, a benzenesulfonyloxy group, a p-toluenesulfonyloxy group or a trifluoromethanesulfonyloxy group, provided that when W' is phenyl or tolyl, the phenyl or tolyl is further converted to Cl, F, H or methyl.

18. A process for preparing a silacyclohexane compound of the following general formula (I)

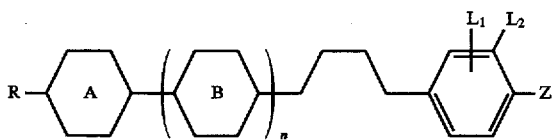

the process comprising:
reacting an organometallic compound of the following general formula (8)

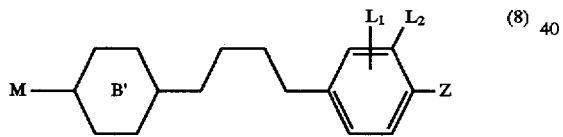

with a compound of the following general formula (9)

wherein

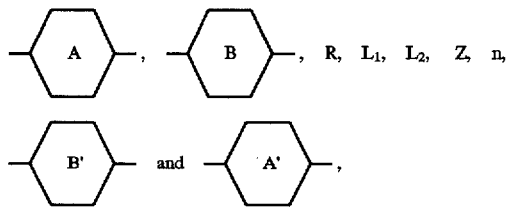

are as defined in claim 14, and Q represents a halogen atom, an alkoxy group, a methanesulfonyloxy group, a benzenesulfonyloxy group, a p-toluenesulfonyloxy group or a trifluoromethanesulfonyloxy group, provided that when W' is phenyl or tolyl, the phenyl or tolyl is further converted to Cl, F, H or methyl.

19. A process for preparing a silacyclohexane compound of the following general formula (II)

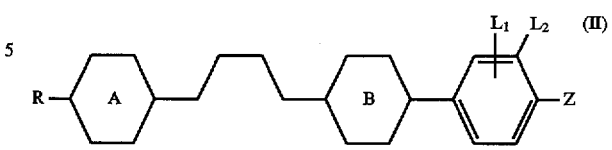

R, $L_1$, $L_2$, Z,

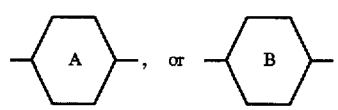

are, respectively, as defined in claim 1, the process comprising:

reacting an organometallic compound of the general formula, R-M, wherein R is as defined in claim 1 and M represents Li, MgP or ZnP wherein P is a halogen atom, with a compound of the following general formula (10)

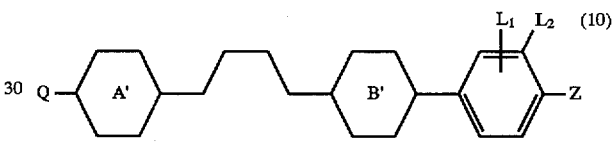

wherein one of

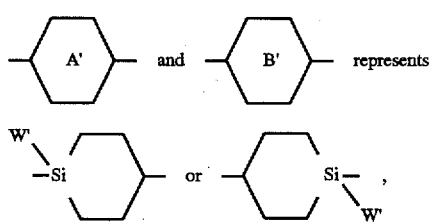

in which W' represents H, methyl, phenyl or tolyl, and the other represents

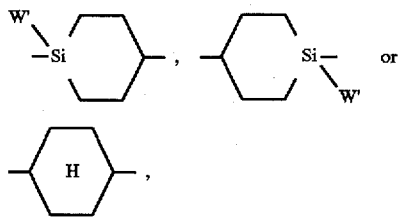

$L_1$, $L_2$ and n are, respectively, as defined in the formula (I), and Q represents a halogen atom, an alkoxy group, a methanesulfonyloxy group, a benzenesulfonyloxy group, a p-toluenesulfonyloxy group or a trifluoromethanesulfonyloxy group, provided that when W' is phenyl or tolyl, the phenyl or tolyl is further converted to Cl, F, H or methyl.

20. A process for preparing a silacyclohexane compound of the following general formula (II)

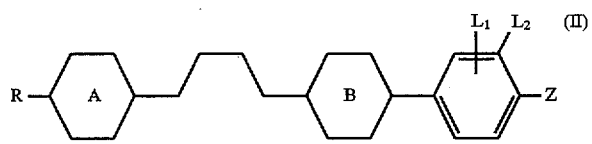

the process comprising:

reacting an organometallic compound of the following formula (11)

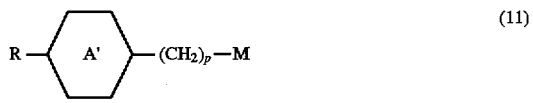

wherein M represents Li, MgP or ZnP in which P represents a halogen, with compound of the following general formula (12)

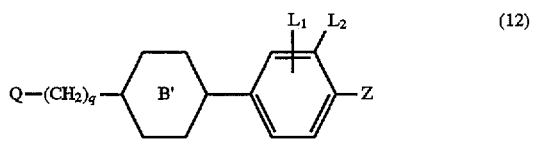

wherein

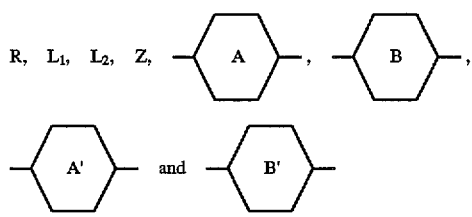

are defined in claim 19, and Q represents a halogen atom, an alkoxy group, a methanesulfonyloxy group, a benzenesulfonyloxy group, a p-toluenesulfonyloxy group or a trifluoromethanesulfonyloxy group, and p and q are, respectively, a value of 0, 1, 2, 3, or 4 provided that (p+q) is 4, provided that when W' is phenyl or tolyl, the phenyl or tolyl is further converted to Cl, F, H or methyl.

21. A process for preparing a silacyclohexane compound of the following general formula (II)

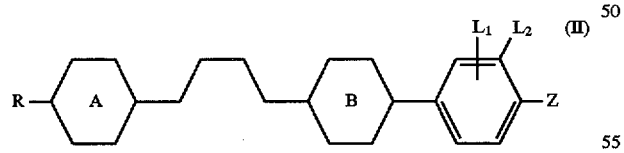

the process comprising:

reacting an organometallic compound of the following formula (13)

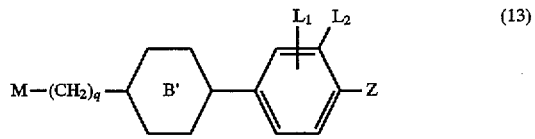

with a compound of the following general formula (14)

wherein

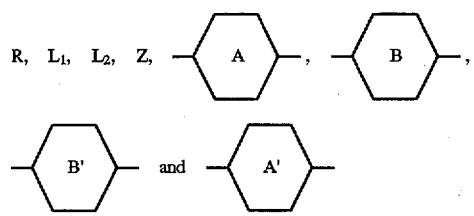

are as defined in claim 19, M represents Li, MgP or ZnP in which P represents halogen and Q represents a halogen atom, an alkoxy group, a methanesulfonyloxy group, a benzenesulfonyloxy group, a p-toluenesulfonyloxy group or a trifluoromethanesulfonyloxy group, and p and q are, respectively, a value of 0, 1, 2, 3 or 4 provided that (p+q) is 4, on the condition that when W' is phenyl or tolyl, the phenyl or tolyl is further converted to Cl, F, H or methyl.

22. A process for preparing a silacyclohexane compound of the following general formula (II)

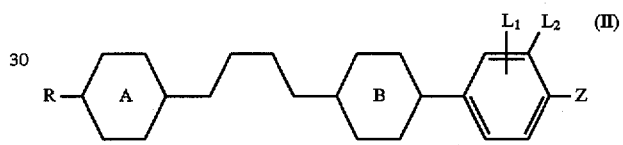

the process comprising:

reacting an organometallic compound of the following formula (15)

with a compound of the following general formula (16)

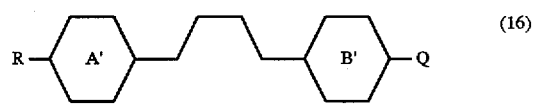

wherein

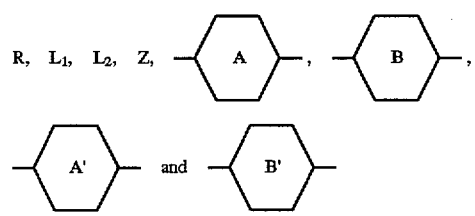

are, respectively, as defined in claim 19, M represents Li, MgP or ZnP in which P represents a halogen, and Q represents a halogen atom, an alkoxy group, a methanesulfonyloxy group, a benzenesulfonyloxy group, a p-toluenesulfonyloxy group or a trifluoromethanesulfonyloxy group, and p and q are, respectively, a value of 0, 1, 2, 3 or 4 provided that (p+q) is 4, on the condition that when W' is phenyl or tolyl, the phenyl or tolyl is further converted to Cl, F, H or methyl.

23. A process for preparing a silacyclohexane compound of the following general formula (II)

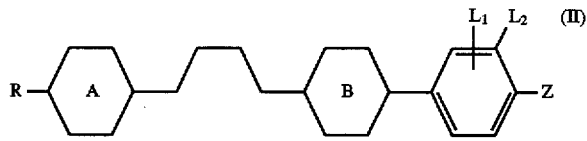

the process comprising:

reacting an organometallic compound of the following formula (17)

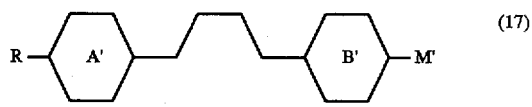

with a compound of the following formula (18)

wherein

R, L₁, L₂, Z,

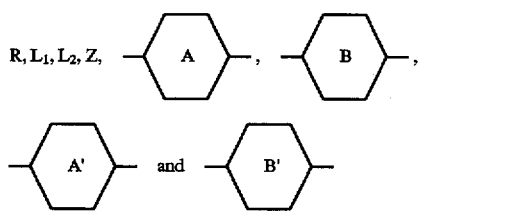

are, respectively, as defined in claim 19 and M' represents MgP or ZnP in which P represents a halogen atom, or B(OY₁)₂ in which Y₁, represents hydrogen or an alkyl group having from 1 to 6 carbon atoms Q' represents a halogen atom, a methanesulfonyloxy group, a benzenesulfonyloxy group, a p-toluenesulfonyloxy group or a trifluoromethanesulfonyloxy group, provided that when W' is phenyl or tolyl, the phenyl or tolyl is further converted to Cl, F, H or methyl.

24. A process for preparing a hydro, fluoro or chlorosilacyclohexane compound from a silacyclohexane compound of the general formula (III) or IV defined in claim 11, wherein at least one of moieties of

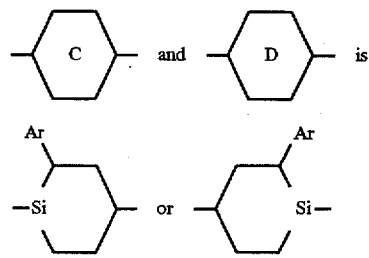

in which Ar is phenyl or tolyl, the process comprising:
subjecting the at least one moiety to de-silylation with an electrophilic reagent to provide a moiety of the formula

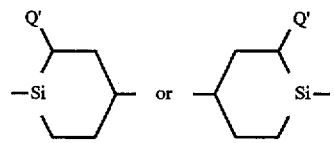

wherein Q' represents Cl, Br or I.

25. A process according to claim 24, further comprising reducing said at least one moiety to convert Q' to hydrogen thereby forming a moiety of the following formula

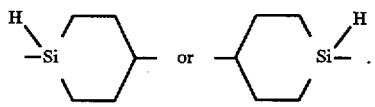

26. A process according to claim 24, further comprising methylating said at least one moiety to convert Q' to methyl thereby forming a moiety of the following formula

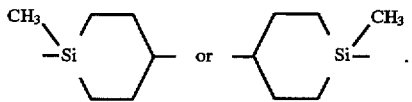

27. A liquid crystal composition comprising at least one silacyclohexane compound selected from the group consisting of compounds of the general formulas (I) and (II) defined in claim 1.

28. A liquid crystal composition according to claim 27, wherein said at least one silacyclohexane compound is present in an mount of from 1 to 50% by mole.

29. A liquid crystal display device comprising the composition defined in claim 27.

* * * * *